(12) United States Patent
Coon et al.

(10) Patent No.: US 9,366,678 B2
(45) Date of Patent: Jun. 14, 2016

(54) NEUTRON ENCODED MASS TAGS FOR ANALYTE QUANTIFICATION

(71) Applicant: Wisconsin Alumni Research Foundation, Madison, WI (US)

(72) Inventors: Joshua J Coon, Middleton, WI (US); Alex Hebert, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 252 days.

(21) Appl. No.: 13/660,677

(22) Filed: Oct. 25, 2012

(65) Prior Publication Data

US 2014/0120565 A1 May 1, 2014

(51) Int. Cl.
*G01N 24/00* (2006.01)
*G01N 33/68* (2006.01)

(52) U.S. Cl.
CPC ........ *G01N 33/6848* (2013.01); *G01N 2458/15* (2013.01); *Y10T 436/24* (2015.01)

(58) Field of Classification Search
None
See application file for complete search history.

(56) References Cited

U.S. PATENT DOCUMENTS

| | | | |
|---|---|---|---|
| 7,939,331 B2 | 5/2011 | Leite et al. | |
| 2005/0147982 A1 | 7/2005 | Pappin et al. | |
| 2005/0147985 A1 | 7/2005 | Pappin et al. | |
| 2005/0148087 A1 | 7/2005 | Pappin et al. | |
| 2006/0105416 A1 | 5/2006 | Pappin et al. | |
| 2006/0172319 A1 | 8/2006 | Yan et al. | |
| 2007/0048752 A1 | 3/2007 | Yan et al. | |
| 2007/0141659 A1 | 6/2007 | Pappin et al. | |
| 2007/0158542 A1 | 7/2007 | Bauer et al. | |
| 2007/0218560 A1 | 9/2007 | Pillai et al. | |
| 2008/0113441 A1 | 5/2008 | Orlando et al. | |
| 2008/0167197 A1 | 7/2008 | Schmidt et al. | |
| 2008/0241955 A1 | 10/2008 | Purkayastha et al. | |
| 2010/0029495 A1 | 2/2010 | Schaefer | |
| 2010/0167267 A1 | 7/2010 | Schulzknappe et al. | |
| 2010/0178710 A1 | 7/2010 | Hamon et al. | |
| 2011/0028685 A1 | 2/2011 | Purkayastha et al. | |
| 2011/0045516 A1 | 2/2011 | Pappin et al. | |
| 2011/0111513 A1 | 5/2011 | Baumann et al. | |
| 2012/0028824 A1 | 2/2012 | Larue et al. | |
| 2012/0071337 A1 | 3/2012 | Lovestone et al. | |

OTHER PUBLICATIONS

Atwood et al. (2008) "Quantitation by Isobaric Labeling: Applications to Glycomics," J. Proteome Res. 7(1):367-374.
Hebert et al. (2013) "Neutron-encoded Mass Signatures for Multiplexed Proteome Quantification," Nat. Methods 10(4):332-334.
Ong et al. (2002) "Stable Isotope Labeling by Amino Acids in Cell Culture, Silac, as a Simple and Accurate Approach to Expression Proteomics," Mol. Cell. Proteomics 1(5):376-386.

(Continued)

*Primary Examiner* — Robert Xu
(74) *Attorney, Agent, or Firm* — Lathrop & Gage LLP

(57) ABSTRACT

The invention provides mass spectrometry methods, compositions and systems which enable a unique platform for analyte quantitation accessing very high degrees of multiplexing and accurate quantification, particularly well-suited for a range of quantitative analysis for proteomics applications. Embodiments of the present methods and systems combine isotopic coding agents characterized by very small differences in molecular mass with mass spectrometry methods providing large resolving power to provide relative or absolute analyte quantification in a large number of samples.

25 Claims, 42 Drawing Sheets

(56) References Cited

OTHER PUBLICATIONS

Treumann et al. (2010) "Isobaric Protein and Peptide Quantification: Perspectives and Issues," *Expert Rev. Proteomics* 7(5):647-653.

International Search Report and Written Opinion, dated May 16, 2014, corresponding to International Application No. PCT/US2013/065311 (filed Oct. 16, 2013), 18pp.

Ashburner et al. (2000) "Gene Ontology: Tool for the Unification of Biology. The Gene Ontology Consortium," *Nat. Genet.* 25(1):25-29.

Ducret et al. (1998) "High Throughput Protein Characterization by Automated Reverse-Phase Chromatography Electrospray Tandem Mass Spectrometry," *Protein Sci.* 7(3):706-719.

Hall et al. (2004) "Isotope-differentiated Binding Energy Shift Tags (IDBEST™) for Improved Targeted Biomarker Discovery and Validation," *Expert Rev. Proteomics* 1(4):421-431.

Link et al. (1999) "Direct Analysis of Protein Complexes Using Mass Spectrometry," *Nat. Biotechnol.* 17(7):676-682.

Liu et al. (2004) "A Model for Random Sampling and Estimation of Relative Protein Abundance in Shotgun Proteomics," *Anal. Chem.* 76(14):4193-4201.

Manning et al. (2002) "The Protein Kinase Complement of the Human Genome," *Science* 298(5600):1912-1934.

McAlister et al. (Published online Aug. 2, 2012) "Increasing the Multiplexing Capacity of TMT Using Reporter Ion Isotopologues with Isobaric Masses," *Analytical Chemistry* 84(17):7469-7478.

Moritz et al. (2010) "Akt-RSK-S6 Kinase Signaling Networks Activated by Oncogenic Receptor Tyrosine Kinases," *Sci. Signal.* 3(136).

Olsen et al. (2010) "Quantitative Phosphoproteomics Reveals Widespread Full Phosphorylation Site Occupancy During Mitosis," *Sci. Signal.* 3(104).

Ong et al. (2003) "Properties of 13C-Substituted Arginine in Stable Isotope by Amino Acids in Cell Culture (SILAC)," *J. Proteome. Res.* 2(2):173-181.

Oppermann et al. (2009) "Large-Scale Proteomics Analysis of the Human Kinome," *Mol. Cell Proteomics* 8(7):1751-1764.

Ross et al. (2004) "Multiplexed Protein Quantification in *Saccharomyces cerevisiae* Using Amine-Reactive Isobaric Tagging Reagents," *Mol. Cell. Proteomics* 3(12):1154-1169.

Sleno. (2012) "The Use of Mass Defect in Modern Mass Spectrometry," *J. Mass. Spectrom.* 47:226-236.

Sohn et al. (Published online Jan. 5, 2012) "Click Chemistry Facilitates Formation of Reporter Ions and Simplified Synthesis of Amine-Reactive Multiplexed Isobaric Tags for Protein Quantification," *J. Am. Chem. Soc.* 134:2672-2680.

Tabb et al. (2010) "Repeatability and Reproducibility in Proteomic Identifications by Liquid Chromatography-Tandem Mass Spectrometry," *J. Proteome. Res.* 9(2):761-776.

Werner et al. (Published online Jul. 30, 2012) "High-Resolution Enabled TMT 8-plexing," *Anal. Chem.* 84(16):7188-7194.

Wisniewski et al. (2009) "Universal Sample Preparation Method for Proteome Analysis," *Nat. Methods* 6(5):359-362.

Wu et al. (2003) "A Method for the Comprehensive Proteomic Analysis of Membrane Proteins," *Nat. Biotechnol.* 21(5):532-538.

NQAAMNPSNTVFDAK

NQAAMNPSNTVFDAK

| Lys ¹³C | ²H | ¹⁵N | ¹⁸O | residue mass (Da) | Δ mass (mDa) |
|---|---|---|---|---|---|
| 0 | 0 | 2 | 0 | 148.0996 | 0.0 |
| 1 | 0 | 1 | 0 | 148.1059 | 6.3 |
| 0 | 1 | 1 | 0 | 148.1088 | 9.2 |
| 0 | 0 | 0 | 1 | 148.1098 | 10.2 |
| 2 | 0 | 0 | 0 | 148.1122 | 12.6 |
| 1 | 1 | 0 | 0 | 148.1152 | 15.6 |
| 0 | 2 | 0 | 0 | 148.1181 | 18.5 |

Figure 9

| residue | Δ mass (mDa) | # of iso-topologues |
|---|---|---|
| Ser | 25.9 | 142 |
| Leu | 35.1 | 334 |
| Tyr | 37.5 | 598 |
| Lys | 44.3 | 544 |
| Met | 46.0 | 478 |
| Arg | 62.8 | 908 |

| # of heavy atoms | Δ in mass (mDa) | # of isotopologues | Plexes at varied spacing (mDa) | | |
|---|---|---|---|---|---|
| | | | 6 | 12 | 18 |
| 4 | 27.8 | 18 | 5 | 3 | 2 |
| 8 | 38.5 | 39 | 7 | 4 | 3 |
| 12 | 35.6 | 35 | 7 | 4 | 3 |
| | | total plexes | 19 | 11 | 8 |

Figure 15

| Element | Symbol | Nominal Mass | Exact Mass | Abundance | X+1 Factor* | X+2 Factor* |
|---|---|---|---|---|---|---|
| Hydrogen | H D or 2H | 1 2 | 1.00783 2.01410 | 99.99 0.01 | | |
| Carbon | 12C 13C | 12 13 | 12.0000 13.0034 | 98.91 1.09 | 1.1n$_C$ | 0.006n$_C^2$ |
| Nitrogen | 14N 15N | 14 15 | 14.0031 15.0001 | 99.6 0.37 | 0.37n$_N$ | |
| Oxygen | 16O 17O 18O | 16 17 18 | 15.9949 16.9991 17.9992 | 99.76 0.037 0.20 | 0.04n$_O$ | 0.2n$_O$ |
| Fluorine | F | 19 | 18.9984 | 100 | | |
| Silicon | 28Si 29Si 30Si | 28 29 30 | 27.9769 28.9765 29.9738 | 92.28 4.70 3.02 | 5.1n$_{Si}$ | 3.3n$_{Si}$ |
| Phosphorus | P | 31 | 30.9738 | 100 | | |
| Sulphur | 32S 33S 34S | 32 33 34 | 31.9721 32.9715 33.9679 | 95.02 0.74 4.22 | 0.78n$_S$ | 4.4n$_S$ |
| Chlorine | 35Cl 37Cl | 35 37 | 34.9689 36.9659 | 75.77 24.23 | | 32.5n$_{Cl}$ |
| Bromine | 79Br 81Br | 79 81 | 78.9183 80.9163 | 50.5 49.5 | | 98.0n$_{Br}$ |
| Iodine | I | 127 | 126.9045 | 100 | | |

Figure 24

Amino Acids

| # | Structure | Composition | Coded Elements |
|---|---|---|---|
| 1 | 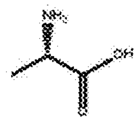 | $C_3H_7NO_2$ | $C_3H_4NO$ |
| 2 | 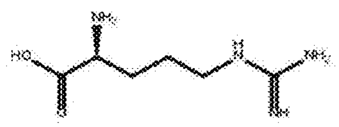 | $C_6H_{14}N_4O_2$ | $C_6H_7N_4O$ |
| 3 | 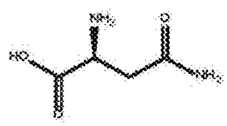 | $C_4H_8N_2O_3$ | $C_4H_3N_2O_2$ |
| 4 | 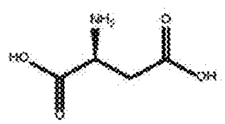 | $C_4H_7NO_4$ | $C_4H_3NO_2$ |
| 5 | 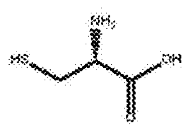 | $C_3H_7NO_2S$ | $C_3H_3NOS$ |
| 6 | 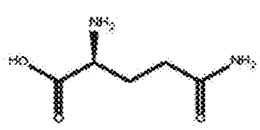 | $C_5H_{10}N_2O_3$ | $C_5H_5N_2O_2$ |
| 7 | 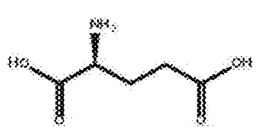 | $C_5H_9NO_4$ | $C_5H_5NO_2$ |

Figure 25

Amino Acids

| aa | Structure | Composition | Coded Elements |
|---|---|---|---|
| 8 | 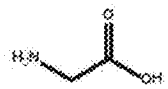 | $C_2H_5NO_2$ | $C_2H_5NO$ |
| 9 | 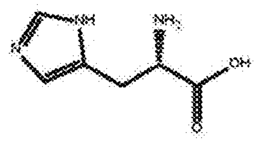 | $C_6H_9N_3O_2$ | $C_6H_9N_3O$ |
| 10 | 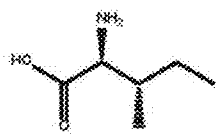 | $C_6H_{13}NO_2$ | $C_6H_{10}NO$ |
| 11 | 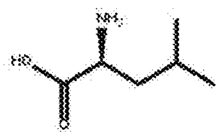 | $C_6H_{13}NO_2$ | $C_6H_{10}NO$ |
| 12 | 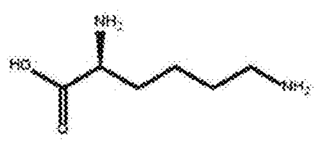 | $C_6H_{14}N_2O_2$ | $C_6H_9N_2O$ |
| 13 | 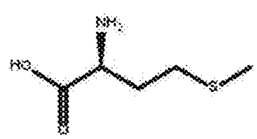 | $C_5H_{11}NO_2S$ | $C_5H_8NOS$ |
| 14 | 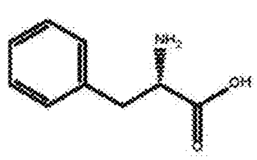 | $C_9H_{11}NO_2$ | $C_9H_8NO$ |

Figure 25 cont.

Amino Acids

| aa | Structure | Composition | Coded Elements |
|---|---|---|---|
| 15 | 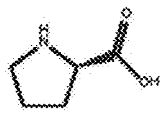 | $C_5H_9NO_2$ | $C_5H_7NO$ |
| 16 | 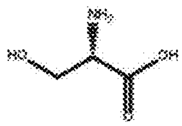 | $C_3H_7NO_3$ | $C_3H_5NO$ |
| 17 | 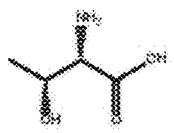 | $C_4H_9NO_3$ | $C_4H_7NO$ |
| 18 | 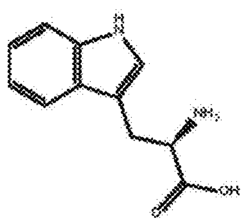 | $C_{11}H_{12}N_2O_2$ | $C_{11}H_{10}N_2O$ |
| 19 | 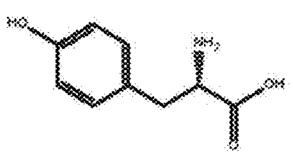 | $C_9H_{11}NO_3$ | $C_9H_9NO$ |
| 20 | 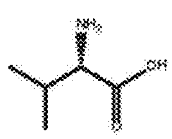 | $C_5H_{11}NO_2$ | $C_5H_9NO$ |

Figure 25 cont.

Peptide label synthesis Reagents

| # | Structure | Composition | Coded Elements |
|---|---|---|---|
| 1 | 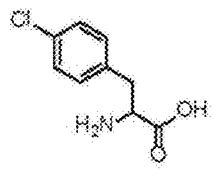 | $C_9H_{10}ClNO_2$ | $C_9H_7ClNO$ |
| 2 | 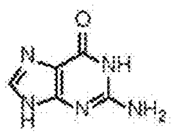 | $C_5H_5N_5O$ | $C_5H_3N_5O$ |
| 3 | 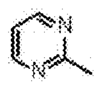 | $C_5H_6N_2$ | $C_5H_4N_2$ |
| 4 | 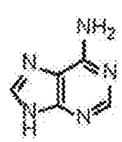 | $C_5H_5N_5$ | $C_5H_2N_5$ |
| 5 | 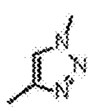 | $C_4H_7N_3$ | $C_4H_5N_3$ |
| 6 | 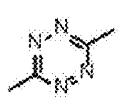 | $C_4H_6N_4$ | $C_4H_6N_4$ |
| 7 | 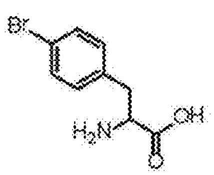 | $C_9H_{10}BrNO_2$ | $C_9H_7BrNO$ |

Peptide label synthesis Reagents

| # | Structure | Composition | Coded Elements |
|---|---|---|---|
| 8 | 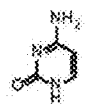 | $C_4H_5N_3O$ | $C_4H_2N_3O$ |
| 9 | 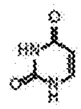 | $C_4H_4N_2O_2$ | $C_4H_2N_2O_2$ |
| 10 | 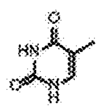 | $C_5H_6N_2O_2$ | $C_5H_4N_2O_2$ |
| 11 | 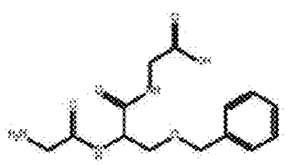 | $C_{14}H_{16}N_3O_4$ | $C_{14}H_{14}N_3O_4$ |
| 12 | 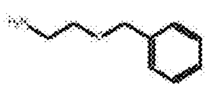 | $C_9H_{13}NO$ | $C_9H_{11}NO$ |
| 13 | 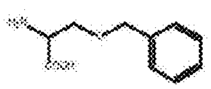 | $C_{10}H_{13}NO_3$ | $C_{10}H_{10}NO_2$ |
| 14 | 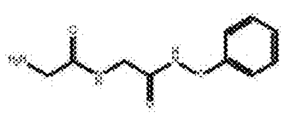 | $C_{10}H_{13}N_3O_3$ | $C_9H_7N_3O_3$ |
| 15 | 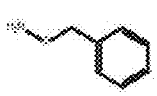 | $C_7H_9NO$ | $C_7H_7NO$ |
| 16 | 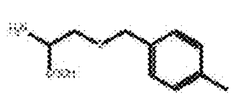 | $C_{11}H_{15}NO_2S$ | $C_{11}H_{12}NOS$ |

Figure 26 cont.

Peptide label synthesis Reagents

| # | Structure | Composition | Coded Elements |
|---|-----------|-------------|----------------|
| 17 | 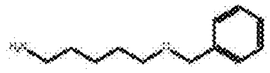 | $C_{12}H_{15}NO$ | $C_{12}H_{17}NO$ |
| 18 | 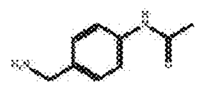 | $C_9H_{12}N_2O$ | $C_9H_9N_2O$ |
| 19 | 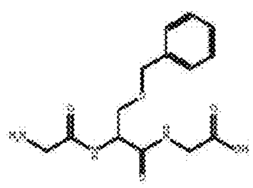 | $C_{14}H_{19}N_3O_5$ | $C_{14}H_{14}N_3O_4$ |
| 20 | 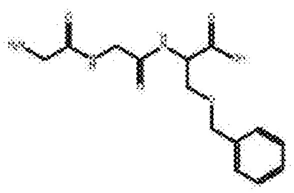 | $C_{14}H_{19}N_3O_5$ | $C_{14}H_{14}N_3O_4$ |
| 21 | 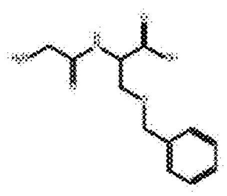 | $C_{17}H_{16}N_2O_4$ | $C_{17}H_{13}N_2O_3$ |
| 22 | 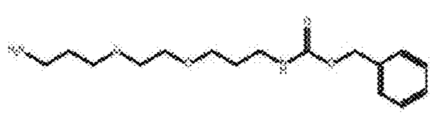 | $C_{16}H_{26}N_2O_4$ | $C_{16}H_{23}N_2O_4$ |
| 23 | 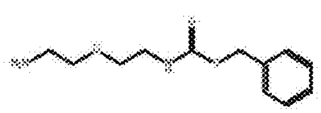 | $C_{17}H_{18}N_2O_3$ | $C_{17}H_{15}N_2O_3$ |
| 24 | 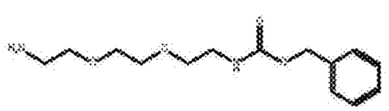 | $C_{14}H_{22}N_2O_4$ | $C_{14}H_{19}N_2O_4$ |

Figure 26 cont.

Peptide label synthesis Reagents

| # | Structure | Composition | Coded Elements |
|---|---|---|---|
| 25 | 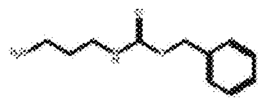 | $C_{17}H_{16}N_2O_2$ | $C_{17}H_{18}N_2O_2$ |
| 26 | 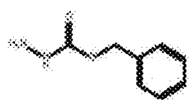 | $C_9H_{10}N_2O_2$ | $C_9H_{10}N_2O_2$ |
| 27 | 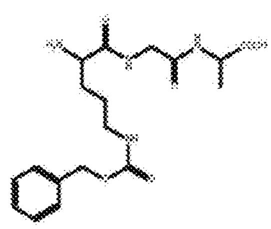 | $C_{18}H_{26}N_4O_6$ | $C_{18}H_{22}N_4O_5$ |
| 28 | 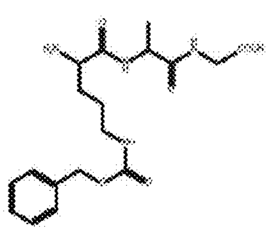 | $C_{18}H_{26}N_4O_5$ | $C_{18}H_{22}N_4O_5$ |

Peptide labels

| # | Structure | Composition | Coded Elements |
|---|---|---|---|
| 29 | 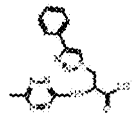 | $C_{14}H_{13}N_3O$ | $C_{14}H_{12}N_3O$ |
| 30 | 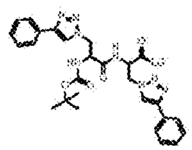 | $C_{27}H_{29}N_5O_4$ | $C_{27}H_{27}N_5O_4$ |
| 31 | 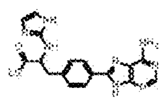 | $C_{17}H_{15}N_5O$ | $C_{17}H_{10}N_5O$ |
| 32 | 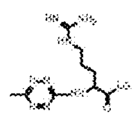 | $C_9H_{15}N_5O$ | $C_9H_{10}N_5O$ |
| 33 | 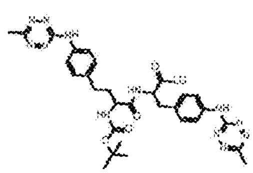 | $C_{30}H_{35}N_{12}O_4$ | $C_{30}H_{31}N_{12}O_4$ |
| 34 | 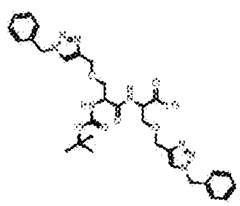 | $C_{31}H_{37}N_8O_6$ | $C_{31}H_{35}N_8O_6$ |
| 35 | 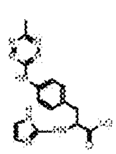 | $C_{15}H_{15}N_3O$ | $C_{15}H_{12}N_3O$ |

Figure 27

Peptide labels

| # | Structure | Composition | Coded Elements |
|---|---|---|---|
| 36 | 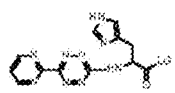 | $C_{12}H_{10}N_3O$ | $C_{12}H_8N_3O$ |
| 37 | 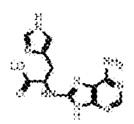 | $C_{11}H_{11}N_8O$ | $C_{11}H_8N_8O$ |
| 38 | 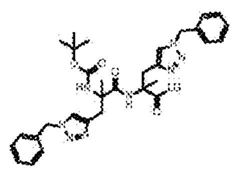 | $C_{31}H_{37}N_8O_4$ | $C_{31}H_{35}N_8O_4$ |
| 39 | 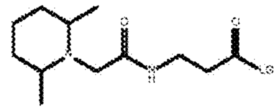 | $C_{17}H_{31}N_2O_2$ | $C_{17}H_{29}N_2O_2$ |
| 40 | 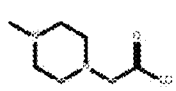 | $C_7H_{13}N_2O$ | $C_7H_{13}N_2O$ |
| 41 | 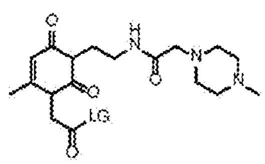 | $C_{18}H_{26}N_3O_4$ | $C_{18}H_{25}N_3O_3$ |

Small molecules label

| # | Structure | Composition | Coded Elements |
|---|---|---|---|
| 1 | 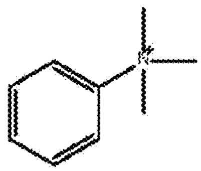 | $C_9H_{13}N$ | $C_9H_{13}N$ |
| 2 | 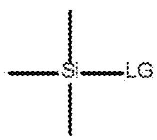 | $C_3H_9Si$ | $C_3H_9Si$ |
| 3 | 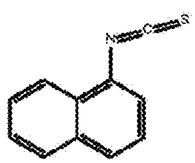 | $C_{11}H_7NS$ | $C_{11}H_7NS$ |
| 4 | 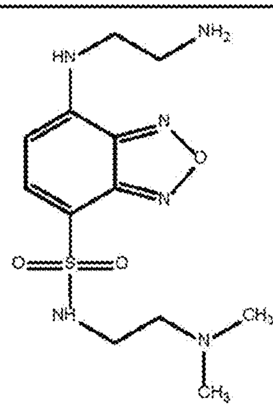 | $C_{17}H_{26}N_6O_3S$ | $C_{17}H_{15}N_6O_3S$ |
| 5 | 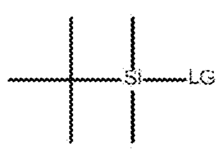 | $C_6H_{15}Si$ | $C_6H_{15}Si$ |
| 6 | 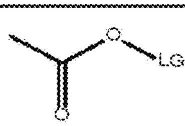 | $C_2H_3O_2$ | $C_2H_3O_2$ |

Figure 28

Small molecules label

| # | Structure | Composition | Coded Elements |
|---|---|---|---|
| 7 | 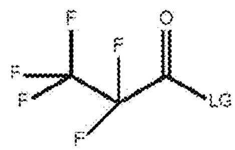 | $C_3F_5O$ | $C_3O$ |
| 8 | 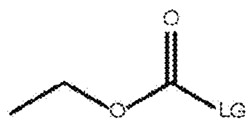 | $C_3H_5O_2$ | $C_3H_5O_2$ |
| 9 | 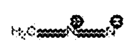 | $CH_2N_2$ | $CH_2N_2$ |
| 10 | 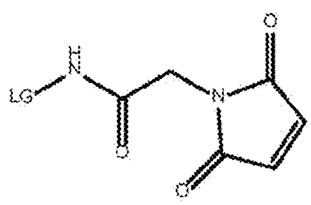 | $C_6H_5N_2O_3$ | $C_6H_4N_2O_2$ |
| 11 | 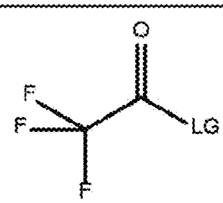 | $C_2F_3O$ | $C_2O$ |
| 12 | 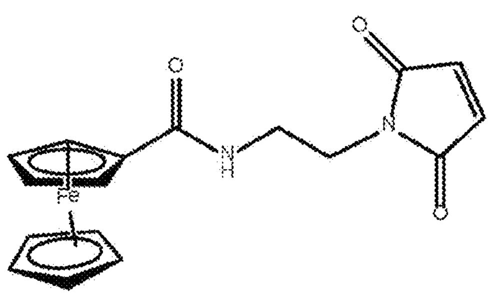 | $C_{17}H_{15}N_2O_3$ | $C_{17}H_{15}N_2O_3$ |

Small molecules label

| # | Structure | Composition | Coded Elements |
|---|---|---|---|
| 13 | 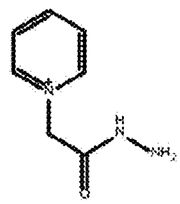 | $C_7H_{11}N_3O$ | $C_7H_7N_3O$ |
| 14 | 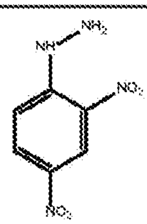 | $C_6H_7N_4O_4$ | $C_6H_3N_4O_4$ |
| 15 | 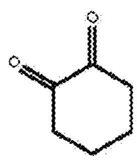 | $C_6H_8O_2$ | $C_6HO_2$ |
| 16 | 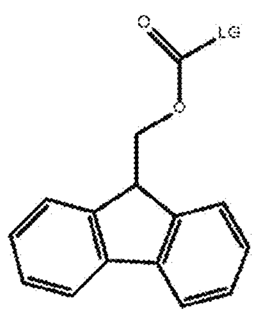 | $C_{15}H_{11}O_2$ | $C_{15}H_{11}O_2$ |
| 17 | 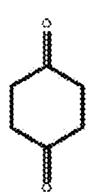 | $C_6H_8O_2$ | $C_6H_8O_2$ |

Small molecules label

| # | Structure | Composition | Coded Elements |
|---|---|---|---|
| 18 | 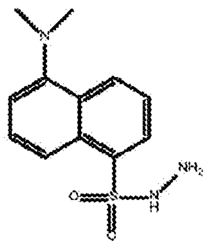 | $C_{12}H_{15}N_3O_2S$ | $C_{12}H_{15}N_3O_2S$ |
| 19 | 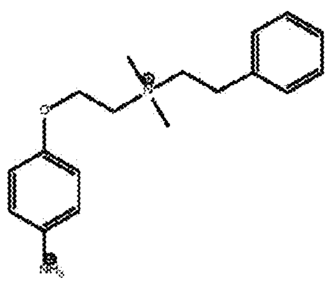 | $C_{18}H_{25}N_2O$ | $C_{18}H_{25}N_2O$ |
| 20 | 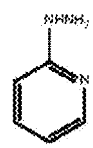 | $C_5H_7N_3$ | $C_5H_7N_3$ |
| 21 | 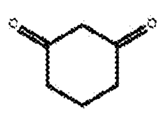 | $C_6H_8O_2$ | $C_6H_8O_2$ |
| 22 | 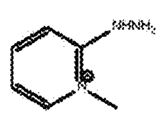 | $C_6H_{10}N_3$ | $C_6H_{10}N_3$ |
| 23 | 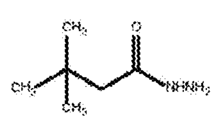 | $C_6H_{14}N_2O$ | $C_6H_{14}N_2O$ |

Figure 28 cont.

Small molecules label

| # | Structure | Composition | Coded Elements |
|---|---|---|---|
| 24 | 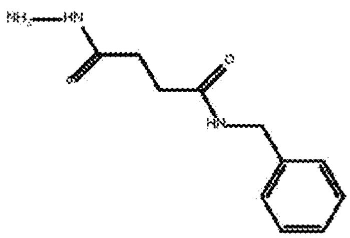 | C₁₁H₁₅N₃O | C₁₁H₁₁N₃O |
| 25 | 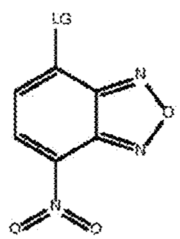 | C₆H₂N₃O₃ | C₆H₂N₃O₃ |
| 26 | 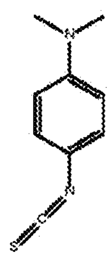 | C₉H₁₀N₂S | C₆H₆N₂S |
| 27 | 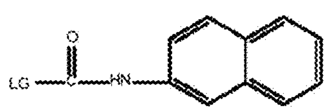 | C₁₅H₁₂N₂O₄ | C₁₁H₇NO |
| 28 | 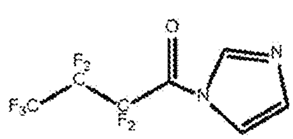 | C₇H₃F₇N₂O | C₂O |

Small molecules label

| # | Structure | Composition | Coded Elements |
|---|---|---|---|
| 29 | 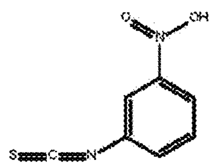 | $C_7H_5N_2O_3S$ | $C_7H_4N_2O_3S$ |
| 30 | 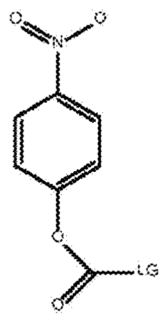 | $C_7H_4NO_4Cl$ | $C_7H_4NO_4$ |
| 31 | 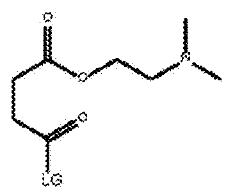 | $C_{11}H_{17}N_1O_3$ | $C_8H_{14}N_1O_3$ |
| 32 | 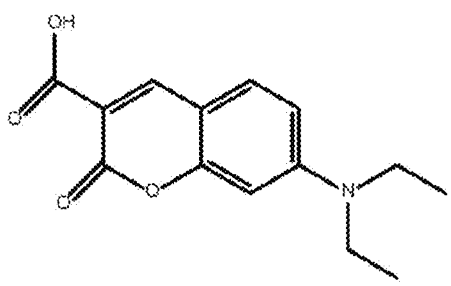 | $C_{14}H_{15}NO_4$ | $C_{14}H_{14}NO_4$ |
| 33 | 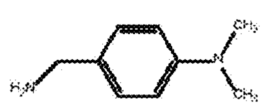 | $C_9H_{14}N_2$ | $C_9H_{12}N_2$ |

Figure 28 cont.

Small molecules label

| # | Structure | Composition | Coded Elements |
|---|-----------|-------------|----------------|
| 34 | 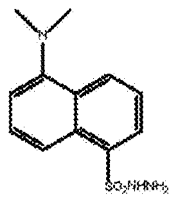 | $C_{12}H_{15}N_3O_2S$ | $C_{12}H_{15}N_3O_2S$ |
| 35 | 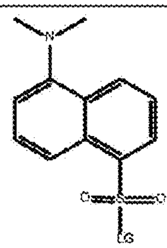 | $C_{12}H_{12}NSO_2$ | $C_{12}H_{12}NSO_2$ |
| 36 | 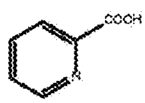 | $C_6H_5NO_2$ | $C_6H_5NO_2$ |
| 37 | 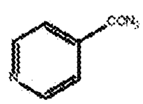 | $C_6H_5N_3O$ | $C_6H_5N_3O$ |
| 38 | 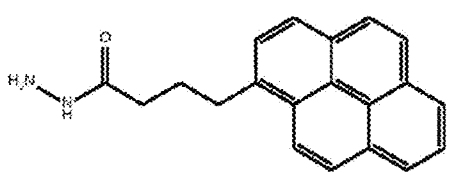 | $C_{20}H_{18}N_2O$ | $C_{20}H_{18}N_2O$ |
| 39 | 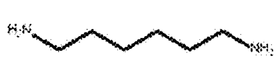 | $C_6H_{16}N_2$ | $C_6H_{16}N_2$ |

Figure 28 cont.

Small molecules label

| # | Structure | Composition | Coded Elements |
|---|---|---|---|
| 40 | 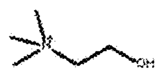 | $C_5H_{14}NO$ | $C_5H_{13}NO$ |
| 41 | 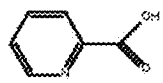 | $C_6H_5NO_2$ | $C_6H_4NO_2$ |
| 42 | 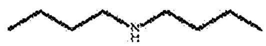 | $C_8H_{19}N$ | $C_8H_{18}N$ |

Figure 28 cont.

NEUTRON ENCODED MASS TAGS FOR ANALYTE QUANTIFICATION

STATEMENT REGARDING FEDERALLY SPONSORED RESEARCH OR DEVELOPMENT

This invention was made with government support under GM080148 awarded by the National Institutes of Health. The government has certain rights in the invention.

CROSS-REFERENCE TO RELATED APPLICATIONS

Not applicable.

BACKGROUND OF INVENTION

Proteome quantification has become an increasingly essential component of modern biology and translational medicine. Whether targeted or global, stable isotope incorporation with mass spectrometry (MS) analysis is the primary mechanism by which protein abundance measurements are determined. There are numerous approaches to introduce stable isotopes into peptides—SILAC, isobariC tagging (TMT/iTRAQ), iCAT, etc. In most conventional approaches, however, these methods incorporate heavy isotopes to increase mass by at least 1 Da. SILAC, the quantification gold standard, for example, typically utilizes a 4 Da spacing so as to limit the isotopic cluster overlap of the heavy and light peptides. This requirement limits the quantitative capacity of SILAC to triplex. The reason for this is twofold: (1) the mass of the amino acids can only be elevated to ~+12 Da and (2) mass spectral complexity is increased as multiple isotopic clusters are introduced.

Isobaric tagging addresses the problem of increases in mass spectra complexity by concealing the quantitative information in the $MS^1$ scan, thereby, permitting a higher level of multiplexing than obtained via conventional SILAC methods. Mc Alister et al. recently report methods for expanding the throughput of methods using TMT isobaric reagents from 6-plex to 8 plex, for example, via techniques that resolve the relatively small isotopic shift resulting from substitution of a $^{15}N$ for a $^{13}C$ in the isobaric tagging agents. [See, Mc Alister et al., *Analytical Chemistry*, accepted manuscript, DOI: 10.1021/ac301572t]. Despite the advances in the degree of multiplexing accessible using isobaric tagging, these methods have been demonstrated to be susceptible to certain limitations that impact their use in quantitative analysis for applications in proteomics. First, isobaric methods suffer from severe dynamic range compression and loss of quantitative accuracy due to precursor interference with in the MS/MS isolation window. Precursor interference in isobaric methods, for example, has been demonstrated to significantly degrade the quantitative accuracy of the technique. Second, quantitative data can only be obtained for peptides that are selected for further $MS^2$ analysis When replicate analyses are necessary, therefore, this becomes a serious problem as there is high variation in which peptides are selected for $MS^2$ from one run to the next (~60%). Third, current isobaric tagging methods are only compatible with collisional activation for dissociation, thus limiting the overall versatility of this technique.

From the foregoing it shall be apparent that a need currently exists for mass spectrometry techniques for proteomic analysis. For example, advanced mass spectrometry techniques are needed that are capable of achieving high degrees of multiplexing necessary for high throughput analysis of protein containing samples. In addition, advanced mass spectrometry techniques are needed that are not susceptible to problems of precursor interference that can impact quantitative accuracy and that are compatible with a range of dissociation techniques including electron capture and electron transfer dissociation methods.

SUMMARY OF THE INVENTION

The invention provides mass spectrometry methods, compositions and systems which enable a unique platform for analyte quantitation accessing very high degrees of multiplexing and accurate quantification, particularly well-suited for a range of quantitative analysis for proteomics applications. Embodiments of the present methods and systems combine isotopic coding agents characterized by very small differences in molecular mass with mass spectrometry methods providing large resolving power to provide relative or absolute analyte quantification in a large number of samples. In some embodiments, for example, quantification methods of the invention access a high degree of multiplexing by introducing isotopic labels from a large number of (e.g., ranging from 2 to 10 and in some embodiments greater than 20) isotopic coding agents that are isotopologues, such as amino acids, tagging agents and/or synthetic proteins and peptides, having mass differences that can be accurately resolved using high resolution mass spectrometry. The methods, compositions and systems described herein enable increased quantitation accuracy compatible with multiplexing necessary to achieve high levels of throughput.

In an aspect, the invention provides a method for determining the abundances of an analyte in a plurality of samples comprising the steps of: (a) providing a plurality of cell cultures including at least a first cell culture and a second cell culture; (b) providing a different isotopically labeled amino acid to each of the cell cultures, wherein the isotopically labeled amino acids of each of the cell cultures are isotopologues of the same amino acid; (c) growing cells of each of the cell cultures, thereby introducing a different isotopic label into proteins generated by each cell culture; (d) generating a sample for each of the cell cultures, wherein each sample is characterized by a different isotopically labeled analyte, the samples including at least a first sample for the first cell culture having a first isotopically labeled analyte and a second sample for the second cell culture having a second isotopically labeled analyte, wherein the isotopically labeled analytes of each sample are isotopologues; and wherein the difference of the molecular masses of the first isotopically labeled analyte and the second isotopically labeled analyte is less than or equal to 300 mDa; (e) analyzing the isotopically labeled analytes for each sample using a mass spectrometry analysis technique providing a resolving power equal to or greater than 100,000, thereby generating an independent and distinguishable mass spectrometry signal for the isotopically labeled analytes of each sample; and (f) comparing the mass spectrometry signals for the isotopically labeled analytes of each sample, thereby determining the abundances of the analyte in the plurality of samples.

In an aspect, the invention provides a method for determining the abundances of an analyte in a plurality of samples comprising the steps of: (a) providing the plurality of samples each having the analyte including at least a first sample and a second sample; (b) providing a different isotopic tagging reagent to each sample, wherein the isotopic tagging reagents of each of the samples are isotopologues, and wherein the isotopic tagging reagents are not isobaric tags having a reporter group and a mass balancing group; (c) chemically reacting the analyte and isotopic tagging reagent of each sample, thereby generating a different isotopically labeled analyte for each sample including a first isotopically labeled analyte for the first sample and a second isotopically labeled analyte for the second sample; wherein the isotopically labeled analytes of each sample are isotopologues; and wherein the difference of the molecular masses of the first isotopically labeled analyte and the second isotopically labeled analyte is less than or equal to 300 mDa; (d) analyzing the isotopically labeled analytes for each sample using a mass spectrometry analysis technique providing a resolving power equal to or greater than 100,000, thereby generating an independent and distinguishable mass spectrometry signal for the isotopically labeled analytes of each sample; and (e) comparing the mass spectrometry signals for the isotopically labeled analytes of each sample, thereby determining the abundance of the analyte in the plurality of samples.

In an aspect, the invention provides a method for determining the abundances of an analyte in a plurality of samples comprising the steps of: (a) providing the plurality of samples each having the analyte including at least a first sample and a second sample; (b) providing a different isotopic tagging reagent to each sample, wherein the isotopic tagging reagents of each of the samples are isotopologues; (c) chemically reacting the analyte and isotopic tagging reagent of each sample, thereby generating a different isotopically labeled analyte for each sample including a first isotopically labeled analyte for the first sample and a second isotopically labeled analyte for the second sample; wherein the isotopically labeled analytes of each sample are isotopologues; and wherein the difference of the molecular masses of the first isotopically labeled analyte and the second isotopically labeled analyte is less than or equal to 300 mDa; (d) analyzing the isotopically labeled analytes for each sample using a mass spectrometry analysis technique providing a resolving power equal to or greater than 100,000, thereby generating an independent and distinguishable mass spectrometry signal for the isotopically labeled analytes of each sample; and (e) comparing the mass spectrometry signals for the isotopically labeled analytes of each sample, thereby determining the abundance of the analyte in the plurality of samples; wherein the step of analyzing the isotopically labeled analytes for each sample using a mass spectrometry analysis technique does not use an isobaric tagging method, for example, wherein the step of analyzing the isotopically labeled analytes for each sample using a mass spectrometry analysis technique does not generate a reporter ion or mass spectrometry data corresponding to a reporter ion.

In some methods of the invention, the isotopically labeled analytes, isotopic tagging reagents, isotopically labeled amino acids and/or isotopically labeled peptide or proteins of the samples do not comprise an isobaric mass tag, such as an TMT or iTRAQ mass tag. In some embodiments, for example, the isotopically labeled analytes, isotopic tagging reagents, isotopically labeled amino acids and/or isotopically labeled peptide or proteins of the samples do not have at least a portion of the functional groups of conventional isobaric mass tags, such as not having a reporter group and/or not having a mass balancing group. It is noted, however, that isotopic tagging reagents of the invention commonly containing reactive groups, such as protein or peptide reactive groups, for example, to allow incorporation of an isotopic label into the analyte via chemical reactions.

In some methods of the invention, the step of analyzing the isotopically labeled analytes for each sample is carried out using a single stage mass spectrometry technique, such as a technique involving fragmentation and detection of product ions generated directed from the analyte such as ions generated directly from electrospray ionization and MALDI techniques. In some embodiments, for example, the step of analyzing the isotopically labeled analytes for each sample using the mass spectrometry analysis technique comprises: (i) generating ions from each of the isotopically labeled analytes for each sample; (ii) fragmenting the ions so as to generate product ions having a different isotopic label for each sample; and (iii) detecting the product ions for each sample. In some embodiments, for example, the product ions are peptide fragment ions having the isotopic label, optionally wherein the product ions are detected without further mass selection or fragmentation of the product ions. In a specific embodiment, the step of analyzing the isotopically labeled analytes for each sample is not carried out using a $MS^x$ multiple stage mass spectrometry, wherein x is greater than or equal to 2, for example, wherein the step of analyzing the isotopically labeled analytes for each sample is not carried out using tandem mass spectrometry. Alternatively, the invention includes methods wherein the step of analyzing the isotopically labeled analytes for each sample is carried out using a $MS^x$ multiple stage mass spectrometry, wherein x is greater than or equal to 2, such as tandem mass spectrometry techniques.

Methods of the invention are compatible with a broad range of approaches for introducing isotopic labels into analytes for generating isotopically labeled analytes, such as reactive techniques, synthetic techniques and metabolic techniques. In reactive techniques, for example, one or more isotopic tagging reagents are provided to a sample under conditions (e.g., concentration of tagging reagent, temperature, pH, ionic strength, solvent composition, etc.) such that at least a portion of the isotopic tagging reagent reacts with analyte to generate isotopically labeled analyte. In synthetic techniques, for example, one or more isotopically labeled standards, such as an isotopically labeled peptide standard, is synthesized, for example via chemical reaction(s) of isotope encoded amino acids, and then added to a sample under analysis. In metabolic techniques, for example, isotope encoded compounds, such as isotopically labeled amino acids or peptides, are provided to a cell culture under conditions wherein the isotopically labeled amino acids or peptides are incorporated into peptides and modified peptides generated by the cells.

In an embodiment, for example, the step of providing the different isotopically labeled amino acids to each of the cell cultures comprises providing a growth medium to each of the cell cultures comprising the isotopically labeled amino acids. In an embodiment, for example, the introducing a different isotopic label into proteins generated by each cell culture is achieved via metabolic incorporation of the isotopically labeled amino acids into cells of the cell cultures. In an embodiment, for example, the step of generating a sample for each of the cell cultures comprises lysing the cells of each of the cell cultures. In an embodiment, for example, the step of generating a sample for each of the cell cultures comprises extracting proteins of each of the cell cultures. In an embodiment, for example, the step of generating a sample for each of the cell cultures comprises digesting proteins of each of the cell cultures. In an embodiment, for example, the samples are digested using trypsin or Endo LysC.

An important aspect of the present methods is use of a series of isotopically labeled analytes, isotopic tagging reagents, isotopically labeled amino acids and/or isotopically labeled peptide or proteins having differences in mass that can be resolved using a mass spectrometry analysis technique providing a resolving power equal to or greater than 100,000. Use of at least a portion of the isotopically labeled analytes, isotopic tagging reagents, isotopically labeled amino acids and/or isotopically labeled peptide or proteins having small differences in molecular mass (e.g., less than or equal to 300 mDa) is beneficial in some embodiments for accessing high multiplexing capabilities. In some embodiments, for example, the step of analyzing the isotopically labeled analytes for each sample comprises resolving differences of the mass to charge ratios and/or molecular masses of the isotopically labeled analytes. In some embodiments, for example, the difference of the molecular masses of the first isotopically labeled analyte and the second isotopically labeled analyte is less than or equal to 100 mDa, and optionally for some applications wherein the difference of the molecular masses of the first isotopically labeled analyte and the second isotopically labeled analyte is less than or equal to 50 mDa and optionally for some applications wherein the difference of the molecular masses of the first isotopically labeled analyte and the second isotopically labeled analyte is greater than or equal to 10 mDa. In some embodiments, for example, the difference of the molecular masses of the first isotopically labeled analyte and the second isotopically labeled analyte is selected over the range of 100 mDa to 1 mDa, and optionally for some applications wherein the difference of the molecular masses of the first isotopically labeled analyte and the second isotopically labeled analyte is selected over the range of 50 mDa to 1 mDa, and optionally for some applications wherein the difference of the molecular masses of the first isotopically labeled analyte and the second isotopically labeled analyte is selected over the range of 10 mDa to 1 mDa. In some embodiments, for example, each of the isotopically labeled analytes have a molecular mass within 100 mDa to 1 mDa of another of the isotopically labeled analyte, and optionally for some applications each of the isotopically labeled analytes have a molecular mass within 50 mDa to 1 mDa of another of the isotopically labeled analyte and optionally for some applications each of the isotopically labeled analytes have a molecular mass within 10 mDa to 1 mDa of another of the isotopically labeled analyte. In some embodiments, for example, the molecular masses of each of the isotopically labeled analytes are within a range of 10000 mDa to 10 mDa, and optionally for some applications the molecular masses of each of the isotopically labeled analytes are within a range of 1000 mDa to 10 mDa, and optionally for some applications the molecular masses of each of the isotopically labeled analytes are within a range of 100 mDa to 10 mDa.

Different isotopically encoded compounds of the invention can have a number of stable heavy isotopes selected over a wide range for different applications. As used herein isotopically encoded compounds refers to compound having one or more stable heavy isotopes functioning as an isotopic label. Isotopically encoded compounds include a range of tagging reagents, standards and/or labeled analytes, such as isotopically labeled analytes, isotopic tagging reagents, isotopically labeled amino acids, isotopically labeled standards and/or isotopically labeled peptide or proteins. Isotopically encoded compounds include compounds having one or more stable heavy isotopes that are isotopologues, for example, isotopologues that can be accurately distinguished using mass spectrometry based on measured mass-to-charge ratios.

In an embodiment, for example, the isotopically labeled analytes, isotopic tagging reagents, isotopically labeled amino acids and/or isotopically labeled peptide or proteins have a number of stable heavy isotopes selected from the group consisting of 2, 3, 4, 5, 6, 7, 8, 9, 10, 11, 12, 13, 14, 15, 16, 17, 18, 19, and 20. In an embodiment, for example, the isotopically labeled analytes, isotopic tagging reagents, isotopically labeled amino acids and/or isotopically labeled peptide or proteins have a number of stable heavy isotopes equal to or greater than 1, and optionally for some applications a number of stable heavy isotopes equal to or greater than 4, and optionally for some applications a number of stable heavy isotopes equal to or greater than 10, and optionally for some applications a number of stable heavy isotopes equal to or greater than 15.

In some embodiments, for example, the isotopically labeled analytes, isotopic tagging reagents, isotopically labeled amino acids and/or isotopically labeled peptide or proteins are selected from the group consisting of: an isotopically labeled analyte, isotopic tagging reagent, isotopically labeled amino acid and/or isotopically labeled peptide or protein having at least one $^{15}$N isotope; an isotopically labeled analyte, isotopic tagging reagent, isotopically labeled amino acid and/or isotopically labeled peptide or protein having at least one $^{13}$C isotope; an isotopically labeled analyte, isotopic tagging reagent, isotopically labeled amino acid and/or isotopically labeled peptide or protein having at least one $^{18}$O isotope; an isotopically labeled analyte, isotopic tagging reagent, isotopically labeled amino acid and/or isotopically labeled peptide or protein having at least one $^{34}$S isotope; and an isotopically labeled analyte, isotopic tagging reagent, isotopically labeled amino acid and/or isotopically labeled peptide or protein having at least one $^{2}$H isotope.

In some embodiments, for example, the isotopically labeled analytes, isotopic tagging reagents, isotopically labeled amino acids and/or isotopically labeled peptide or proteins are selected from the group consisting of: an isotopically labeled analyte, isotopic tagging reagent, isotopically labeled amino acid and/or isotopically labeled peptide or protein having at least two $^{13}$C isotopes; an isotopically labeled analyte, isotopic tagging reagent, isotopically labeled amino acid and/or isotopically labeled peptide or protein having at least one $^{13}$C isotope and at least one $^{15}$N isotope; an isotopically labeled analyte, isotopic tagging reagent, isotopically labeled amino acid and/or isotopically labeled peptide or protein having at least one $^{13}$C isotope and at least one $^{2}$H isotope; an isotopically labeled analyte, isotopic tagging reagent, isotopically labeled amino acid and/or isotopically labeled peptide or protein having at least one $^{13}$C isotope and at least one $^{18}$O isotope; an isotopically labeled analyte, isotopic tagging reagent, isotopically labeled amino acid and/or isotopically labeled peptide or protein having at least one $^{13}$C isotope and a $^{34}$S isotope; an isotopically labeled analyte, isotopic tagging reagent, isotopically labeled amino acid and/or isotopically labeled peptide or protein having at least two $^{15}$N isotopes; an isotopically labeled analyte, isotopic tagging reagent, isotopically labeled amino acid and/or isotopically labeled peptide or protein having at least one $^{15}$N isotope and at least one $^{2}$H isotope; an isotopically labeled analyte, isotopic tagging reagent, isotopically labeled amino acid and/or isotopically labeled peptide or protein having at least one $^{15}$N isotope and at least one $^{18}$O isotope; an isotopically labeled analyte, isotopic tagging reagent, isotopically labeled amino acid and/or isotopically labeled peptide or protein having at least one $^{15}$N isotope and at least one $^{34}$S isotope; an isotopically labeled analyte, isotopic tagging reagent, isotopically labeled amino acid and/or isotopically labeled peptide or protein having at least two $^{2}$H isotopes; an isotopically labeled analyte, isotopic tagging reagent, isotopically labeled amino acid and/or isotopically labeled peptide or protein having at least one $^{2}$H isotope and at least one $^{18}$O isotope; an isotopically labeled analyte, isotopic tagging reagent, isotopically labeled amino acid and/or isotopically labeled peptide or protein having at least one $^{2}$H isotope and at least one $^{34}$S isotope; an isotopically labeled analyte, isotopic tagging reagent, isotopically labeled amino acid and/or isotopically labeled peptide or protein having at least two $^{18}O$ isotopes; an isotopically labeled analyte, isotopic tagging reagent, isotopically labeled amino acid and/or isotopically labeled peptide or protein having at least one $^{18}O$ isotope and at least one $^{34}S$ isotope; an isotopically labeled analyte, isotopic tagging reagent, isotopically labeled amino acid and/or isotopically labeled peptide or protein having at least one $^{13}C$ isotope, at least one $^{15}N$ isotope and at least one $^{2}H$ isotope; an isotopically labeled analyte, isotopic tagging reagent, isotopically labeled amino acid and/or isotopically labeled peptide or protein having at least one $^{13}C$ isotope, at least one $^{15}N$ isotope and at least one $^{18}O$ isotope; an isotopically labeled analyte, isotopic tagging reagent, isotopically labeled amino acid and/or isotopically labeled peptide or protein having at least one $^{13}C$ isotope, at least one $^{15}N$ isotope and at least one $^{34}S$ isotope; and an isotopically labeled analyte, isotopic tagging reagent, isotopically labeled amino acid and/or isotopically labeled peptide or protein having at least one $^{18}O$ isotope, at least one $^{15}N$ isotope and at least one $^{34}S$ isotope.

In an embodiment, for example, the isotopically labeled analytes, isotopic tagging reagents, isotopically labeled amino acids and/or isotopically labeled peptide or proteins are selected from the group consisting of: an isotopically labeled analyte, isotopic tagging reagent, isotopically labeled amino acid and/or isotopically labeled peptide or protein isotopically labeled amino acid selected from the group consisting of: an isotopically labeled analyte, isotopic tagging reagent, isotopically labeled amino acid and/or isotopically labeled peptide or protein having 1, 2, 3, or 4 $^{15}N$ isotopes; an isotopically labeled analyte, isotopic tagging reagent, isotopically labeled amino acid and/or isotopically labeled peptide or protein having 1, 2, 3, 4, 5, 6, 7, 8, 9, 10 or 11 $^{13}C$ isotopes; an isotopically labeled analyte, isotopic tagging reagent, isotopically labeled amino acid and/or isotopically labeled peptide or protein having 1 or 2 $^{15}O$ isotopes; an isotopically labeled analyte, isotopic tagging reagent, isotopically labeled amino acid and/or isotopically labeled peptide or protein having one $^{34}S$ isotope; and an isotopically labeled analyte, isotopic tagging reagent, isotopically labeled amino acid and/or isotopically labeled peptide or protein having 1, 2, 3, 4, 5, 6, 7, 8, 9, or 10 $^{2}H$ isotopes.

Methods of the invention include quantification approaches using isotopically encoded amino acids, such as isotopically labeled amino acids. In an embodiment, for example, the isotopically labeled amino acids are isotopologues of a naturally occurring amino acid. In an embodiment, for example, the isotopically labeled amino acids are isotopologues of serine, leucine, tyrosine, lysine, methionine, or arginine. In an embodiment, for example, the isotopologues have a number of stable heavy isotopes selected from the group consisting of 2, 3, 4, 5, 6, 7, 8, 9, 10, 11, 12, 13, 14, 15, 16, 17, 18, 19, and 20. In an embodiment, for example, the isotopically labeled amino acids of each sample have an isotopic composition for its coded element formula selected from the group consisting of:

$^{12}C_{3-i}{}^{13}C_i{}^{1}H_{4-j}{}^{2}H_j{}^{14}N_{1-n}{}^{15}N_n{}^{16}O_{1-o}{}^{18}O_o$, wherein $i \leq 3$, $j \leq 4$, $n \leq 1$, $o \leq 1$;
$^{12}C_{6-i}{}^{13}C_i{}^{1}H_{7-j}{}^{2}H_j{}^{14}N_{4-n}{}^{15}N_n{}^{16}O_{1-o}{}^{18}O_o$, wherein $i \leq 6$, $j \leq 7$, $n \leq 4$, $o \leq 1$;
$^{12}C_{4-i}{}^{13}C_i{}^{1}H_{3-j}{}^{2}H_j{}^{14}N_{2-n}{}^{15}N_n{}^{16}O_{2-o}{}^{18}O_o$, wherein $i \leq 4$, $j \leq 3$, $n \leq 2$, $o \leq 2$;
$^{12}C_{4-i}{}^{13}C_i{}^{1}H_{3-j}{}^{2}H_j{}^{14}N_{1-n}{}^{15}N_n{}^{16}O_{2-o}{}^{18}O_o$, wherein $i \leq 4$, $j \leq 3$, $n \leq 1$, $o \leq 2$;
$^{12}C_{3-i}{}^{13}C_i{}^{1}H_{3-j}{}^{2}H_j{}^{14}N_{1-n}{}^{15}N_n{}^{16}O_{1-o}{}^{18}O_o{}^{32}S_{1-p}{}^{34}S_p$, wherein $i \leq 3$, $j \leq 3$, $n \leq 1$, $o \leq 1$, $p \leq 1$;
$^{12}C_{5-i}{}^{13}C_i{}^{1}H_{5-j}{}^{2}H_j{}^{14}N_{1-n}{}^{15}N_n{}^{16}O_{2-o}{}^{18}O_o$, wherein $i \leq 5$, $j \leq 5$, $n \leq 1$, $o \leq 2$;
$^{12}C_{5-i}{}^{13}C_i{}^{1}H_{5-j}{}^{2}H_j{}^{14}N_{2-n}{}^{15}N_n{}^{16}O_{2-o}{}^{18}O_o$, wherein $i \leq 5$, $j \leq 5$, $n \leq 2$, $o \leq 2$;
$^{12}C_{2-i}{}^{13}C_i{}^{1}H_{2-j}{}^{2}H_j{}^{14}N_{1-n}{}^{15}N_n{}^{16}O_{1-o}{}^{18}O_o$, wherein $i \leq 2$, $j \leq 2$, $n \leq 1$, $o \leq 1$;
$^{12}C_{6-i}{}^{13}C_i{}^{1}H_{5-j}{}^{2}H_j{}^{14}N_{3-n}{}^{15}N_n{}^{16}O_{1-o}{}^{18}O_o$, wherein $i \leq 6$, $j \leq 5$, $n \leq 3$, $o \leq 1$;
$^{12}C_{6-i}{}^{13}C_i{}^{1}H_{10-j}{}^{2}H_j{}^{14}N_{1-n}{}^{15}N_n{}^{16}O_{1-o}{}^{18}O_o$, wherein $i \leq 6$, $j \leq 10$, $n \leq 1$, $o \leq 1$;
$^{12}C_{6-i}{}^{13}C_i{}^{1}H_{10-j}{}^{2}H_j{}^{14}N_{1-n}{}^{15}N_n{}^{16}O_{1-o}{}^{18}O_o$, wherein $i \leq 6$, $j \leq 10$, $n \leq 1$, $o \leq 1$;
$^{12}C_{6-i}{}^{13}C_i{}^{1}H_{9-j}{}^{2}H_j{}^{14}N_{2-n}{}^{15}N_n{}^{16}O_{1-o}{}^{18}O_o$, wherein $i \leq 6$, $j \leq 9$, $n \leq 2$, $o \leq 1$;
$^{12}C_{5-i}{}^{13}C_i{}^{1}H_{8-j}{}^{2}H_j{}^{14}N_{1-n}{}^{15}N_n{}^{16}O_{1-o}{}^{18}O_o{}^{32}S_{1-p}{}^{34}S_p$, wherein $i \leq 5$, $j \leq 8$, $n \leq 1$, $o \leq 1$, $p \leq 1$;
$^{12}C_{9-i}{}^{13}C_i{}^{1}H_{8-j}{}^{2}H_j{}^{14}N_{1-n}{}^{15}N_n{}^{16}O_{1-o}{}^{18}O_o$, wherein $i \leq 9$, $j \leq 8$, $n \leq 1$, $o \leq 1$;
$^{12}C_{5-i}{}^{13}C_i{}^{1}H_{7-j}{}^{2}H_j{}^{14}N_{1-n}{}^{15}N_n{}^{16}O_{1-o}{}^{18}O_o$, wherein $i \leq 5$, $j \leq 7$, $n \leq 1$, $o \leq 1$;
$^{12}C_{3-i}{}^{13}C_i{}^{1}H_{3-j}{}^{2}H_j{}^{14}N_{1-n}{}^{15}N_n{}^{16}O_{1-o}{}^{18}O_o$, wherein $i \leq 3$, $j \leq 3$, $n \leq 1$, $o \leq 1$;
$^{12}C_{4-i}{}^{13}C_i{}^{1}H_{5-j}{}^{2}H_j{}^{14}N_{1-n}{}^{15}N_n{}^{16}O_{1-o}{}^{18}O_o$, wherein $i \leq 4$, $j \leq 5$, $n \leq 1$, $o \leq 1$;
$^{12}C_{11-i}{}^{13}C_i{}^{1}H_{8-j}{}^{2}H_j{}^{14}N_{2-n}{}^{15}N_n{}^{16}O_{1-o}{}^{18}O_o$, wherein $i \leq 11$, $j \leq 8$, $n \leq 2$, $o \leq 1$;
$^{12}C_{9-i}{}^{13}C_i{}^{1}H_{7-j}{}^{2}H_j{}^{14}N_{1-n}{}^{15}N_n{}^{16}O_{1-o}{}^{18}O_o$, wherein $i \leq 9$, $j \leq 7$, $n \leq 1$, $o \leq 1$; and
$^{12}C_{5-i}{}^{13}C_i{}^{1}H_{8-j}{}^{2}H_j{}^{14}N_{1-n}{}^{15}N_n{}^{16}O_{1-o}{}^{18}O_o$, wherein $i \leq 5$, $j \leq 8$, $n \leq 1$, $o \leq 1$;
wherein each of i, j, n, o and p are independently an integer or 0.

In an embodiment, for example, the isotopically labeled amino acids have the formula:

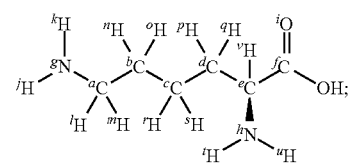

(FX1)

wherein, $^gN$ and $^hN$ are both $^{15}N$; or one of $^gN$ and $^hN$ is $^{15}N$, and one of $^aC$, $^bC$, $^cC$, $^dC$, $^eC$ and $^fC$ is $^{13}C$; or one of $^gN$ and $^hN$ is $^{15}N$, and one of $^jH$, $^kH$, $^lH$, $^mH$, $^nH$, $^oH$, $^pH$, $^qH$, $^rH$, $^sH$, $^tH$, $^uH$ and $^vH$ is $^{2}H$; or $^iO$ is $^{18}O$; or two of $^aC$, $^bC$, $^cC$, $^dC$, $^eC$ and $^fC$ are $^{13}C$; or one of $^aC$, $^bC$, $^cC$, $^dC$, $^eC$ and $^fC$ is $^{13}C$, and one of $^jH$, $^kH$, $^lH$, $^mH$, $^nH$, $^oH$, $^pH$, $^qH$, $^rH$, $^sH$, $^tH$, $^uH$ and $^vH$ is $^{2}H$; or two of $^jH$, $^kH$, $^lH$, $^mH$, $^nH$, $^oH$, $^pH$, $^qH$, $^rH$, $^sH$, $^tH$, $^uH$ and $^vH$ are $^{2}H$.

In an embodiment, for example, the isotopically labeled amino acids have the formula:

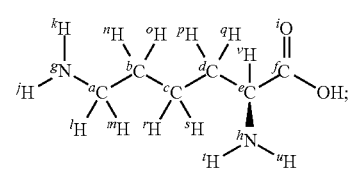

(FX1)

wherein, $^gN$ and $^hN$ are both $^{15}N$, and $^iO$ is $^{18}O$; or $^gN$ and $^hN$ are both $^{15}N$, and two of $^aC$, $^bC$, $^cC$, $^dC$, $^eC$ and $^fC$ are $^{13}C$; or $^g$N and $^h$N are both $^{15}$N, one of $^a$C, $^b$C, $^c$C, $^d$C, $^e$C and $^f$C is $^{13}$C, and one of $^j$H, $^k$H, $^l$H; $^m$H, $^n$H, $^o$H, $^p$H, $^q$H, $^r$H, $^s$H, $^t$H, $^u$H and $^v$H is $^2$H; or one of $^g$N and $^h$N is $^{15}$N, one of $^a$C, $^b$C, $^c$C, $^d$C, $^e$C and $^f$C is $^{13}$C, and $^i$O is $^{18}$O; or $^g$N and $^h$N are both $^{15}$N, and two of $^j$H, $^k$H, $^l$H, $^m$H, $^n$H, $^o$H, $^p$H, $^q$H, $^r$H, $^s$H, $^t$H, $^u$H and $^v$H are $^2$H; or one of $^g$N and $^h$N is $^{15}$N, and three of $^a$C, $^b$C, $^c$C, $^d$C, $^e$C and $^f$C are $^{13}$C; or one of $^g$N and $^h$N is $^{15}$N, one of $^j$H, $^k$H, $^l$H, $^m$H, $^n$H, $^o$H, $^p$H, $^q$H, $^r$H, $^s$H, $^t$H, $^u$H and $^v$H is $^2$H, and $^i$O is $^{18}$O; or one of $^g$N and $^h$N is $^{15}$N, two of $^a$C, $^b$C, $^c$C, $^d$C, $^e$C and $^f$C are $^{13}$C, and one of $^j$H, $^k$H, $^l$H, $^m$H, $^n$H, $^o$H, $^p$H, $^q$H, $^r$H, $^s$H, $^t$H, $^u$H and $^v$H is $^2$H; or two of $^a$C, $^b$C, $^c$C, $^d$C, $^e$C and $^f$C are $^{13}$C, and $^i$O is $^{18}$O; or one of $^g$N and $^h$N is $^{15}$N, one of $^a$C, $^b$C, $^c$C, $^d$C, $^e$C and $^f$C is $^{13}$C, and two of $^j$H, $^k$H, $^l$H, $^m$H, $^n$H, $^o$H, $^p$H, $^q$H, $^r$H, $^s$H, $^t$H, $^u$H and $^v$H are $^2$H; or four of $^a$C, $^b$C, $^c$C, $^d$C, $^e$C and $^f$C are $^{13}$C; or one of $^a$C, $^b$C, $^c$C, $^d$C, $^e$C and $^f$C is $^{13}$C, one of $^j$H, $^k$H, $^l$H, $^m$H, $^n$H, $^o$H, $^p$H, $^q$H, $^r$H, $^s$H, $^t$H, $^u$H and $^v$H is $^2$H, and $^i$O is $^{18}$O; or one of $^g$N and $^h$N is $^{15}$N, and three of $^j$H, $^k$H, $^l$H, $^m$H, $^n$H, $^o$H, $^p$H, $^q$H, $^r$H, $^s$H, $^t$H, $^u$H and $^v$H are $^2$H; or three of $^a$C, $^b$C, $^c$C, $^d$C, $^e$C and $^f$C are $^{13}$C, and one of $^j$H, $^k$H, $^l$H, $^m$H, $^n$H, $^o$H, $^p$H, $^q$H, $^r$H, $^s$H, $^t$H, $^u$H and $^v$H is $^2$H; or two of $^j$H, $^k$H, $^l$H, $^m$H, $^n$H, $^o$H, $^p$H, $^q$H, $^r$H, $^s$H, $^t$H, $^u$H and $^v$H are $^2$H, and $^i$O is $^{18}$O; or two of $^a$C, $^b$C, $^c$C, $^d$C, $^e$C and $^f$C are $^{13}$C, and two of $^j$H, $^k$H, $^l$H, $^m$H, $^n$H, $^o$H, $^p$H, $^q$H, $^r$H, $^s$H, $^t$H, $^u$H and $^v$H are $^2$H; or one of $^a$C, $^b$C, $^c$C, $^d$C, $^e$C and $^f$C is $^{13}$C, and three of $^j$H, $^k$H, $^l$H, $^m$H, $^n$H, $^o$H, $^p$H, $^q$H, $^r$H, $^s$H, $^t$H, $^u$H and $^v$H are $^2$H; or four of $^j$H, $^k$H, $^l$H, $^m$H, $^n$H, $^o$H, $^p$H, $^q$H, $^r$H, $^s$H, $^t$H, $^u$H and $^v$H are $^2$H.

In an embodiment, for example, the isotopically labeled amino acids have the formula:

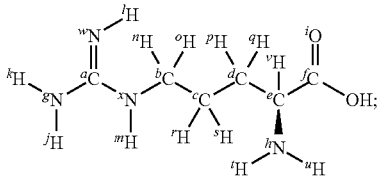

(FX2)

wherein, two of $^g$N, $^h$N, $^w$N and $^x$N are $^{15}$N; or one of $^g$N, $^h$N, $^w$N and $^x$N is $^{15}$N, and one of $^a$C, $^b$C, $^c$C, $^d$C, $^e$C and $^f$C is $^{13}$C; or one of $^g$N, $^h$N, $^w$N and $^x$N is $^{15}$N, and one of $^j$H, $^k$H, $^l$H, $^m$H, $^n$H, $^o$H, $^p$H, $^q$H, $^r$H, $^s$H, $^t$H, $^u$H and $^v$H is $^2$H; or $^i$O is $^{18}$O; or two of $^a$C, $^b$C, $^c$C, $^d$C, $^e$C and $^f$C are $^{13}$C; or one of $^a$C, $^b$C, $^c$C, $^d$C, $^e$C and $^f$C is $^{13}$C, and one of $^j$H, $^k$H, $^l$H, $^m$H, $^n$H, $^o$H, $^p$H, $^q$H, $^r$H, $^s$H, $^t$H, $^u$H and $^v$H is $^2$H; or two of $^j$H, $^k$H, $^l$H, $^m$H, $^n$H, $^o$H, $^p$H, $^q$H, $^r$H, $^s$H, $^t$H, $^u$H and $^v$H are $^2$H.

In an embodiment, for example, the isotopically labeled amino acids have the formula:

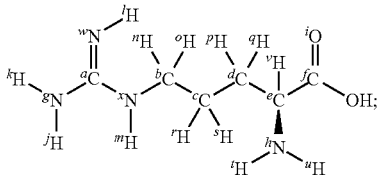

(FX2)

wherein, four of $^g$N, $^h$N, $^w$N and $^x$N are $^{15}$N; or three of $^g$N, $^h$N, $^w$N and $^x$N are $^{15}$N, and one of $^a$C, $^b$C, $^c$C, $^d$C, $^e$C and $^f$C is $^{13}$C; or three of $^g$N, $^h$N, $^w$N and $^x$N are $^{15}$N, and one of $^j$H, $^k$H, $^l$H, $^m$H, $^n$H, $^o$H, $^p$H, $^q$H, $^r$H, $^s$H, $^t$H, $^u$H and $^v$H is $^2$H; or two of $^g$N, $^h$N, $^w$N and $^x$N are $^{15}$N, and $^i$O is $^{18}$O; or two of $^g$N, $^h$N, $^w$N and $^x$N are $^{15}$N, and two of $^a$C, $^b$C, $^c$C, $^d$C, $^e$C and $^f$C are $^{13}$C; or two of $^g$N, $^h$N, $^w$N and $^x$N are $^{15}$N, one of $^a$C, $^b$C, $^c$C, $^d$C, $^e$C and $^f$C is $^{13}$C, and one of $^j$H, $^k$H, $^l$H, $^m$H, $^n$H, $^o$H, $^p$H, $^q$H, $^r$H, $^s$H, $^t$H, $^u$H and $^v$H is $^2$H; or one of $^g$N, $^h$N, $^w$N and $^x$N is $^{15}$N, one of $^a$C, $^b$C, $^c$C, $^d$C, $^e$C and $^f$C is $^{13}$C, and $^i$O is $^{18}$O; or two of $^g$N, $^h$N, $^w$N and $^x$N are $^{15}$N, and two of $^j$H, $^k$H, $^l$H, $^m$H, $^n$H, $^o$H, $^p$H, $^q$H, $^r$H, $^s$H, $^t$H, $^u$H and $^v$H are $^2$H; or one of $^g$N, $^h$N, $^w$N and $^x$N is $^{15}$N, and three of $^a$C, $^b$C, $^c$C, $^d$C, $^e$C and $^f$C are $^{13}$C; or one of $^g$N, $^h$N, $^w$N and $^x$N is $^{15}$N, one of $^j$H, $^k$H, $^l$H, $^m$H, $^n$H, $^o$H, $^p$H, $^q$H, $^r$H, $^s$H, $^t$H, $^u$H and $^v$H is $^2$H, and $^i$O is $^{18}$O; or one of $^g$N, $^h$N, $^w$N and $^x$N is $^{15}$N, two of $^a$C, $^b$C, $^c$C, $^d$C, $^e$C and $^f$C are $^{13}$C, and one of $^j$H, $^k$H, $^l$H, $^m$H, $^n$H, $^o$H, $^p$H, $^q$H, $^r$H, $^s$H, $^t$H, $^u$H and $^v$H is $^2$H; or two of $^a$C, $^b$C, $^c$C, $^d$C, $^e$C and $^f$C are $^{13}$C, and $^i$O is $^{18}$O; or one of $^g$N, $^h$N, $^w$N and $^x$N is $^{15}$N, one of $^a$C, $^b$C, $^c$C, $^d$C, $^e$C and $^f$C is $^{13}$C, and two of $^j$H, $^k$H, $^l$H, $^m$H, $^n$H, $^o$H, $^p$H, $^q$H, $^r$H, $^s$H, $^t$H, $^u$H and $^v$H are $^2$H; or four of $^a$C, $^b$C, $^c$C, $^d$C, $^e$C and $^f$C are $^{13}$C; or one of $^a$C, $^b$C, $^c$C, $^d$C, $^e$C and $^f$C is $^{13}$C, one of $^j$H, $^k$H, $^l$H, $^m$H, $^n$H, $^o$H, $^p$H, $^q$H, $^r$H, $^s$H, $^t$H, $^u$H and $^v$H is $^2$H, and $^i$O is $^{18}$O; or one of $^g$N, $^h$N, $^w$N and $^x$N is $^{15}$N, and three of $^j$H, $^k$H, $^l$H, $^m$H, $^n$H, $^o$H, $^p$H, $^q$H, $^r$H, $^s$H, $^t$H, $^u$H and $^v$H are $^2$H; or three of $^a$C, $^b$C, $^c$C, $^d$C, $^e$C and $^f$C are $^{13}$C, and one of $^j$H, $^k$H, $^l$H, $^m$H, $^n$H, $^o$H, $^p$H, $^q$H, $^r$H, $^s$H, $^t$H, $^u$H and $^v$H is $^2$H; or two of $^j$H, $^k$H, $^l$H, $^m$H, $^n$H, $^o$H, $^p$H, $^q$H, $^r$H, $^s$H, $^t$H, $^u$H and $^v$H are $^2$H, and $^i$O is $^{18}$O; or two of $^a$C, $^b$C, $^c$C, $^d$C, $^e$C and $^f$C are $^{13}$C, and two of $^j$H, $^k$H, $^l$H, $^m$H, $^n$H, $^o$H, $^p$H, $^q$H, $^r$H, $^s$H, $^t$H, $^u$H and $^v$H are $^2$H; or one of $^a$C, $^b$C, $^c$C, $^d$C, $^e$C and $^f$C is $^{13}$C, and three of $^j$H, $^k$H, $^l$H, $^m$H, $^n$H, $^o$H, $^p$H, $^q$H, $^r$H, $^s$H, $^t$H, $^u$H and $^v$H are $^2$H; or four of $^j$H, $^k$H, $^l$H, $^m$H, $^n$H, $^o$H, $^p$H, $^q$H, $^r$H, $^s$H, $^t$H, $^u$H and $^v$H are $^2$H.

Methods of the invention include quantification approaches using isotopically encoded tagging agents, such as isotopically labeled tagging reagents, and isotopically encoded labels, such as isotopically labeled functional groups of analytes including isotopically labeled peptide groups. In an embodiment, for example, the isotopic tagging reagents comprise an amine reactive group or a carboxylic acid reactive group, such as one or more functional groups that react with an amine group or carboxylic acid group of a protein or peptide. In an embodiment, for example, the isotopic tagging reagents are isotopologues of a peptide isotopic tag or modified peptide isotopic tag. In an embodiment, for example, the isotopic tagging reagents are isotopologues of a peptide label reagent. In an embodiment, for example, the isotopologues of the peptide isotopic tag or modified peptide isotopic tag of each sample have an isotopic composition for its coded element formula selected from the group consisting of:

$^{12}C_{9-i}{}^{13}C_i{}^{1}H_{7-j}{}^{2}H_j{}^{35}Cl_{1-m}{}^{37}Cl_m{}^{14}N_{1-n}{}^{15}N_n{}^{16}O_{1-o}{}^{18}O_o$, wherein $i \leq 9$, $j \leq 7$, $m \leq 1$, $n \leq 1$, $o \leq 1$;

$^{12}C_{5-i}{}^{13}C_i{}^{1}H_{1-j}{}^{2}H_j{}^{14}N_{5-n}{}^{15}N_n{}^{16}O_{1-o}{}^{18}O_o$, wherein $i \leq 5$, $j \leq 1$, $n \leq 5$, $o \leq 1$;

$^{12}C_{5-i}{}^{13}C_i{}^{1}H_{6-j}{}^{2}H_j{}^{14}N_{2-n}{}^{15}N_n$, wherein $i \leq 5$, $j \leq 6$, $n \leq 2$;

$^{12}C_{3-i}{}^{13}C_i{}^{1}H_{2-j}{}^{2}H_j{}^{14}N_{5-n}{}^{15}N_n$, wherein $i \leq 3$, $j \leq 2$, $n \leq 5$;

$^{12}C_{4-i}{}^{13}C_i{}^{1}H_{7-j}{}^{2}H_j{}^{14}N_{3-n}{}^{15}N_n$, wherein $i \leq 4$, $j \leq 7$, $n \leq 3$;

$^{12}C_{4-i}{}^{13}C_i{}^{1}H_{6-j}{}^{2}H_j{}^{14}N_{4-n}{}^{15}N_n$, wherein $i \leq 4$, $j \leq 6$, $n \leq 4$;

$^{12}C_{9-i}{}^{13}C_i{}^{1}H_{7-j}{}^{2}H_j{}^{79}Br_{1-l}{}^{14}N_{1-n}{}^{15}N_n{}^{16}O_{1-o}{}^{18}O_o$, wherein $i \leq 9$, $j \leq 7$, $l \leq 1$, $n \leq 1$, $o \leq 1$;

$^{12}C_{4-i}{}^{13}C_i{}^{1}H_{2-j}{}^{2}H_j{}^{14}N_{3-n}{}^{15}N_n{}^{16}O_{1-o}{}^{18}O_o$, wherein $i \leq 4$, $j \leq 2$, $n \leq 3$, $o \leq 1$;

$^{12}C_{4-i}{}^{13}C_i{}^{1}H_{2-j}{}^{2}H_j{}^{14}N_{2-n}{}^{15}N_n{}^{16}O_{2-o}{}^{18}O_o$, wherein $i \leq 4$, $j \leq 2$, $n \leq 2$, $o \leq 2$;

$^{12}C_{5-i}{}^{13}C_i{}^{1}H_{4-j}{}^{2}H_j{}^{14}N_{2-n}{}^{15}N_n{}^{16}O_{2-o}{}^{18}O_o$, wherein $i \leq 5$, $j \leq 4$, $n \leq 2$, $o \leq 2$;

$^{12}C_{14-i}{}^{13}C_i{}^{1}H_{14-j}{}^{2}H_j{}^{14}N_{3-n}{}^{15}N_n{}^{16}O_{4-o}{}^{18}O_o$, wherein $i \leq 14$, $j \leq 14$, $n \leq 3$, $o \leq 4$;

$^{12}C_{9-i}{}^{13}C_i{}^{1}H_{11-j}{}^{2}H_j{}^{14}N_{1-n}{}^{15}N_n{}^{16}O_{1-o}{}^{18}O_o$, wherein $i \leq 9$, $j \leq 11$, $n \leq 1$, $o \leq 1$;

$^{12}C_{10-i}{}^{13}C_i{}^{1}H_{10-j}{}^{2}H_j{}^{14}N_{1-n}{}^{15}N_n{}^{16}O_{2-o}{}^{18}O_o$, wherein $i \leq 10$, $j \leq 10$, $n \leq 1$, $o \leq 2$;

$^{12}C_{10-i}{}^{13}C_i{}^1H_{9-j}{}^2H_j{}^{14}N_{3-n}{}^{15}N_n{}^{16}O_{3-o}{}^{18}O_o$, wherein i≤10, j≤9, n≤3, o≤3;
$^{12}C_{7-i}{}^{13}C_i{}^1H_{7-j}{}^2H_j{}^{14}N_{1-n}{}^{15}N_n{}^{16}O_{1-o}{}^{18}O_o$, wherein i≤7, j≤7, n≤1, o≤1;
$^{12}C_{11-i}{}^{13}C_i{}^1H_{12-j}{}^2H_j{}^{14}N_{1-n}{}^{15}N_n{}^{16}O_{1-o}{}^{18}O_o{}^{32}S_{1-p}{}^{34}S_p$, wherein i≤11, j≤12, n≤1, o≤1, p≤1;
$^{12}C_{12-i}{}^{13}C_i{}^1H_{17-j}{}^2H_j{}^{14}N_{1-n}{}^{15}N_n{}^{16}O_{1-o}{}^{18}O_o$, wherein i≤12, j≤17, n≤1, o≤1;
$^{12}C_{9-i}{}^{13}C_i{}^1H_{9-j}{}^2H_j{}^{14}N_{2-n}{}^{15}N_n{}^{16}O_{1-o}{}^{18}O_o$, wherein i≤9, j≤9, n≤2, o≤1;
$^{12}C_{14-i}{}^{13}C_i{}^1H_{14-j}{}^2H_j{}^{14}N_{3-n}{}^{15}N_n{}^{16}O_{4-o}{}^{18}O_o$, wherein i≤14, j≤14, n≤3, o≤4;
$^{12}C_{14-i}{}^{13}C_i{}^1H_{14-j}{}^2H_j{}^{14}N_{3-n}{}^{15}N_n{}^{16}O_{4-o}{}^{18}O_o$, wherein i≤14, j≤14, n≤3, o≤4;
$^{12}C_{12-i}{}^{13}C_i{}^1H_{13-j}{}^2H_j{}^{14}N_{2-n}{}^{15}N_n{}^{16}O_{3-o}{}^{18}O_o$, wherein i≤12, j≤13, n≤2, o≤3;
$^{12}C_{16-i}{}^{13}C_i{}^1H_{23-j}{}^2H_j{}^{14}N_{2-n}{}^{15}N_n{}^{16}O_{4-o}{}^{18}O_o$, wherein i≤16, j≤23, n≤2, o≤4;
$^{12}C_{12-i}{}^{13}C_i{}^1H_{15-j}{}^2H_j{}^{14}N_{2-n}{}^{15}N_n{}^{16}O_{3-o}{}^{18}O_o$, wherein i≤12, j≤15, n≤2, o≤3;
$^{12}C_{14-i}{}^{13}C_i{}^1H_{19-j}{}^2H_j{}^{14}N_{2-n}{}^{15}N_n{}^{16}O_{4-o}{}^{18}O_o$, wherein i≤14, j≤19, n≤2, o≤4;
$^{12}C_{11-i}{}^{13}C_i{}^1H_{13-j}{}^2H_j{}^{14}N_{2-n}{}^{15}N_n{}^{16}O_{2-o}{}^{18}O_o$, wherein i≤11, j≤13, n≤2, o≤2;
$^{12}C_{8-i}{}^{13}C_i{}^1H_{7-j}{}^2H_j{}^{14}N_{2-n}{}^{15}N_n{}^{16}O_{2-o}{}^{18}O_o$, wherein i≤8, j≤7, n≤2, o≤2;
$^{12}C_{18-i}{}^{13}C_i{}^1H_{21-j}{}^2H_j{}^{14}N_{4-n}{}^{15}N_n{}^{16}O_{5-o}{}^{18}O_o$, wherein i≤18, j≤21, n≤4, o≤5; and
$^{12}C_{18-i}{}^{13}C_i{}^1H_{21-j}{}^2H_j{}^{14}N_{4-n}{}^{15}N_n{}^{16}O_{5-o}{}^{18}O_o$, wherein i≤18, j≤21, n≤4, o≤5;
wherein each of i, j, l, m, n, o, and p are independently an integer or 0.

In an embodiment, for example, the isotopically labeled analytes independently comprise a peptide label. In an embodiment, for example, the peptide label of each isotopically labeled analyte has an isotopic composition for its coded element formula selected from the group consisting of:
$^{12}C_{14-i}{}^{13}C_i{}^1H_{12-j}{}^2H_j{}^{14}N_{8-n}{}^{15}N_n{}^{16}O_{1-o}{}^{18}O_o$, wherein i≤14, j≤12, n≤8, o≤1;
$^{12}C_{27-i}{}^{13}C_i{}^1H_{27-j}{}^2H_j{}^{14}N_{8-n}{}^{15}N_n{}^{16}O_{4-o}{}^{18}O_o$, wherein i≤27, j≤27, n≤8, o≤4;
$^{12}C_{17-i}{}^{13}C_i{}^1H_{10-j}{}^2H_j{}^{14}N_{6-n}{}^{15}N_n{}^{16}O_{1-o}{}^{18}O_o$, wherein i≤17, j≤10, n≤6, o≤1;
$^{12}C_{9-i}{}^{13}C_i{}^1H_{10-j}{}^2H_j{}^{14}N_{6-n}{}^{15}N_n{}^{16}O_{1-o}{}^{18}O_o$, wherein i≤9, j≤10, n≤6, o≤1;
$^{12}C_{30-i}{}^{13}C_i{}^1H_{31-j}{}^2H_j{}^{14}N_{12-n}{}^{15}N_n{}^{16}O_{4-o}{}^{18}O_o$, wherein i≤30, j≤31, n≤12, o≤4;
$^{12}C_{31-i}{}^{13}C_i{}^1H_{35-j}{}^2H_j{}^{14}N_{8-n}{}^{15}N_n{}^{16}O_{6-o}{}^{18}O_o$, wherein i≤31, j≤35, n≤8, o≤6;
$^{12}C_{15-i}{}^{13}C_i{}^1H_{12-j}{}^2H_j{}^{14}N_{8-n}{}^{15}N_n{}^{16}O_{1-o}{}^{18}O_o$, wherein i≤15, j≤12, n≤8, o≤1;
$^{12}C_{12-i}{}^{13}C_i{}^1H_{8-j}{}^2H_j{}^{14}N_{9-n}{}^{15}N_n{}^{16}O_{1-o}{}^{18}O_o$, wherein i≤12, j≤8, n≤9, o≤1;
$^{12}C_{11-i}{}^{13}C_i{}^1H_{6-j}{}^2H_j{}^{14}N_{8-n}{}^{15}N_n{}^{16}O_{1-o}{}^{18}O_o$, wherein i≤11, j≤6, n≤8, o≤1;
$^{12}C_{31-i}{}^{13}C_i{}^1H_{35-j}{}^2H_j{}^{14}N_{8-n}{}^{15}N_n{}^{16}O_{4-o}{}^{18}O_o$, wherein i≤31, j≤35, n≤8, o≤4;
$^{12}C_{12-i}{}^{13}C_i{}^1H_{20-j}{}^2H_j{}^{14}N_{2-n}{}^{15}N_n{}^{16}O_{2-o}{}^{18}O_o$, wherein i≤12, j≤20, n≤2, o≤2;
$^{12}C_{7-i}{}^{13}C_i{}^1H_{13-j}{}^2H_j{}^{14}N_{2-n}{}^{15}N_n{}^{16}O_{1-o}{}^{18}O_o$, wherein i≤7, j≤13, n≤2, o≤1; and
$^{12}C_{18-i}{}^{13}C_i{}^1H_{25-j}{}^2H_j{}^{14}N_{3-n}{}^{15}N_n{}^{16}O_{3-o}{}^{18}O_o$, wherein i≤18, j≤25, n≤3, o≤3;
wherein each of i, j, n, and o are independently an integer or 0.

In an embodiment, for example, the isotopic tagging reagents of the methods are isotopologues of a small molecule isotopic tag. In an embodiment, for example, the isotopologues of the small molecule isotopic tag of each sample have an isotopic composition for its coded element formula selected from the group consisting of:
$^{12}C_{9-i}{}^{13}C_i{}^1H_{14-j}{}^2H_j{}^{14}N_{1-n}{}^{15}N_n$, wherein i≤9, j≤14, n≤1;
$^{12}C_{3-i}{}^{13}C_i{}^1H_{9-j}{}^2H_j{}^{28}Si_{1-q}{}^{30}Si_q$, wherein i≤3, j≤9, q≤1;
$^{12}C_{11-i}{}^{13}C_i{}^1H_{7-j}{}^2H_j{}^{14}N_{1-n}{}^{15}N_n{}^{32}Si_{1-p}{}^{34}S_p$, wherein i≤11, j≤7, n≤1, p≤1;
$^{12}C_{12-i}{}^{13}C_i{}^1H_{16-j}{}^2H_j{}^{14}N_{6-n}{}^{15}N_n{}^{16}O_{2-o}{}^{18}O_o{}^{32}S_{1-p}{}^{34}S_p$, wherein i≤12, j≤16, n≤6, o≤2, p≤1;
$^{12}C_{6-i}{}^{13}C_i{}^1H_{15-j}{}^2H_j{}^{28}Si_{1-q}{}^{30}Si_q$, wherein i≤6, j≤15, q≤1;
$^{12}C_{2-i}{}^{13}C_i{}^1H_{3-j}{}^2H_j{}^{16}O_{2-o}{}^{18}O_o$, wherein I≤2, j≤3, o≤2;
$^{12}C_{3-i}{}^{13}C_i{}^{16}O_{1-o}{}^{18}O_o$, wherein i≤3, o≤1;
$^{12}C_{4-i}{}^{13}C_i{}^1H_{5-j}{}^2H_j{}^{16}O_{2-o}{}^{18}O_o$, wherein i≤4, j≤5, o≤2;
$^{12}C_{1-i}{}^{13}C_i{}^1H_{2-j}{}^2H_j{}^{14}N_{2-n}{}^{15}N_n$, wherein i≤1, j≤2, n≤2;
$^{12}C_{6-i}{}^{13}C_i{}^1H_{4-j}{}^2H_j{}^{14}N_{2-n}{}^{15}N_n{}^{16}O_{2-o}{}^{18}O_o$, wherein i≤6, j≤4, n≤2, o≤2;
$^{12}C_{2-i}{}^{13}C_i{}^{16}O_{1-o}{}^{18}O_o$, wherein i≤2, o≤1;
$^{12}C_{7-i}{}^{13}C_i{}^1H_{6-j}{}^2H_j{}^{14}N_{2-n}{}^{15}N_n{}^{16}O_{3-o}{}^{18}O_o$, wherein i≤7, j≤6, n≤2, o≤3;
$^{12}C_{7-i}{}^{13}C_i{}^1H_{7-j}{}^2H_j{}^{14}N_{3-n}{}^{15}N_n{}^{16}O_{1-o}{}^{18}O_o$, wherein i≤7, j≤7, n≤3, o≤1;
$^{12}C_{6-i}{}^{13}C_i{}^1H_{3-j}{}^2H_j{}^{14}N_{4-n}{}^{15}N_n{}^{16}O_{4-o}{}^{18}O_o$, wherein i≤6, j≤3, n≤4, o≤4;
$^{12}C_{6-i}{}^{13}C_i{}^1H_{1-j}{}^{16}O_{2-o}{}^{18}O_o$, wherein i≤6, j≤1, o≤2;
$^{12}C_{15-i}{}^{13}C_i{}^1H_{11-j}{}^2H_j{}^{16}O_{2-o}{}^{18}O_o$, wherein i≤15, j≤11, o≤2;
$^{12}C_{6-i}{}^{13}C_i{}^1H_{8-j}{}^2H_j{}^{16}O_{2-o}{}^{18}O_o$, wherein i≤6, j≤8, o≤2;
$^{12}C_{12-i}{}^{13}C_i{}^1H_{12-j}{}^2H_j{}^{14}N_{3-n}{}^{15}N_n{}^{16}O_{2-o}{}^{18}O_o{}^{32}S_{1-p}{}^{34}S_p$, wherein i≤12, j≤12, n≤3, o≤2, p≤1;
$^{12}C_{18-i}{}^{13}C_i{}^1H_{23-j}{}^2H_j{}^{14}N_{2-n}{}^{15}N_n{}^{16}O_{1-o}{}^{18}O_o$, wherein i≤18, j≤23, n≤2, o≤1;
$^{12}C_{5-i}{}^{13}C_i{}^1H_{4-j}{}^2H_j{}^{14}N_{3-n}{}^{15}N_n$, wherein i≤5, j≤4, n≤3;
$^{12}C_{6-i}{}^{13}C_i{}^1H_{8-j}{}^2H_j{}^{16}O_{2-o}{}^{18}O_o$, wherein i≤6, j≤8, o≤2;
$^{12}C_{6-i}{}^{13}C_i{}^1H_{7-j}{}^2H_j{}^{14}N_{3-n}{}^{15}N_n$, wherein i≤6, j≤7, n≤3;
$^{12}C_{6-i}{}^{13}C_i{}^1H_{11-j}{}^2H_j{}^{14}N_{2-n}{}^{15}N_n{}^{16}O_{1-o}{}^{18}O_o$, wherein i≤6, j≤11, n≤2, o≤1;
$^{12}C_{11-i}{}^{13}C_i{}^1H_{11-j}{}^2H_j{}^{14}N_{3-n}{}^{15}N_n{}^{16}O_{1-o}{}^{18}O_o$, wherein i≤11, j≤11, n≤3, o≤1;
$^{12}C_{6-i}{}^{13}C_i{}^1H_{2-j}{}^2H_j{}^{14}N_{3-n}{}^{15}N_n{}^{16}O_{3-o}{}^{18}O_o$, wherein i≤6, j≤2, n≤3, o≤3;
$^{12}C_{9-i}{}^{13}C_i{}^1H_{10-j}{}^2H_j{}^{14}N_{2-n}{}^{15}N_n{}^{32}S_{1-p}{}^{34}S_p$, wherein i≤9, j≤10, n≤2, p≤1;
$^{12}C_{11-i}{}^{13}C_i{}^1H_{7-j}{}^2H_j{}^{14}N_{1-n}{}^{15}N_n{}^{16}O_{1-o}{}^{18}O_o$, wherein i≤11, j≤7, n≤1, o≤1;
$^{12}C_{4-i}{}^{13}C_i{}^{16}O_{1-o}{}^{18}O_o$, wherein i≤4, o≤1;
$^{12}C_{7-i}{}^{13}C_i{}^1H_{4-j}{}^2H_j{}^{14}N_{2-n}{}^{15}N_n{}^{16}O_{2-o}{}^{18}O_o{}^{32}S_{1-p}{}^{34}S_p$, wherein i≤7, j≤4, n≤2, o≤2, p≤1;
$^{12}C_{7-i}{}^{13}C_i{}^1H_{4-j}{}^2H_j{}^{14}N_{1-n}{}^{15}N_n{}^{16}O_{4-o}{}^{18}O_o$, wherein i≤7, j≤4, n≤1, o≤4;
$^{12}C_{8-i}{}^{13}C_i{}^1H_{14-j}{}^2H_j{}^{14}N_{1-n}{}^{15}N_n{}^{16}O_{3-o}{}^{18}O_o$, wherein i≤8, j≤14, n≤1, o≤3;
$^{12}C_{14-i}{}^{13}C_i{}^1H_{14-j}{}^2H_j{}^{14}N_{1-n}{}^{15}N_n{}^{16}O_{4-o}{}^{18}O_o$, wherein i≤14, j≤14, n≤1, o≤4;
$^{12}C_{9-i}{}^{13}C_i{}^1H_{12-j}{}^2H_j{}^{14}N_{2-n}{}^{15}N_n$, wherein i≤9, j≤12, n≤2;
$^{12}C_{12-i}{}^{13}C_i{}^1H_{12-j}{}^2H_j{}^{14}N_{3-n}{}^{15}N_n{}^{16}O_{2-o}{}^{18}O_o{}^{32}S_{1-p}{}^{34}S_p$, wherein i≤12, j≤12, n≤3, o≤2, p≤1;
$^{12}C_{12-i}{}^{13}C_i{}^1H_{12-j}{}^2H_j{}^{14}N_{1-n}{}^{15}N_n{}^{16}O_{2-o}{}^{18}O_o{}^{32}S_{1-p}{}^{34}S_p$, i≤12, j≤12, n≤1, o≤2, p≤1;
$^{12}C_{6-i}{}^{13}C_i{}^1H_{4-j}{}^2H_j{}^{14}N_{1-n}{}^{15}N_n{}^{16}O_{2-o}{}^{18}O_o$, wherein i≤6, j≤4, n≤1, o≤2;
$^{12}C_{6-i}{}^{13}C_i{}^1H_{4-j}{}^2H_j{}^{14}N_{4-n}{}^{15}N_n{}^{16}O_{1-o}{}^{18}O_o$, wherein i≤6, j≤4, n≤4, o≤1;
$^{12}C_{20-i}{}^{13}C_i{}^1H_{15-j}{}^2H_j{}^{14}N_{2-n}{}^{15}N_n{}^{16}O_{1-o}{}^{18}O_o$, wherein i≤20, j≤15, n≤2, o≤1;
$^{12}C_{6-i}{}^{13}C_i{}^1H_{12-j}{}^2H_j{}^{14}N_{2-n}{}^{15}N_n$, wherein i≤6, j≤12, n≤2;
$^{12}C_{5-i}{}^{13}C_i{}^1H_{13-j}{}^2H_j{}^{14}N_{1-n}{}^{15}N_n{}^{16}O_{1-o}{}^{18}O_o$, wherein i≤5, j≤13, n≤1, o≤1;

$^{12}C_{6-i}{}^{13}C_i{}^1H_{4-j}{}^2H_j{}^{14}N_{1-n}{}^{15}N_n{}^{16}O_{2-o}{}^{18}O_o$, wherein i≤6, j≤4, n≤1, o≤2; and
$^{12}C_{8-i}{}^{13}C_i{}^1H_{18-j}{}^2H_j{}^{14}N_{1-n}{}^{15}N_n$, wherein i≤8, j≤18, n≤1;
wherein each of i, j, n, o, p and q are independently an integer or 0.

Isotopically encoded compounds useful in the present methods, such as the isotopically labeled analytes, isotopic tagging reagents, isotopically labeled amino acids and/or isotopically labeled peptide or proteins, may comprise a wide range of stable isotope combinations. In an embodiment, for example, at least a portion of the isotopically labeled analytes, isotopic tagging reagents, isotopically labeled amino acids and/or isotopically labeled peptide or proteins comprises at least one $^{12}C$ isotope and at least one $^{15}N$ isotope; and at least a portion of the isotopically labeled analytes, isotopic tagging reagents, isotopically labeled amino acids and/or isotopically labeled peptide or proteins comprises at least one $^{13}C$ isotope and at least one $^{14}N$ isotope. In an embodiment, for example, at least a portion of the isotopically labeled analytes, isotopic tagging reagents, isotopically labeled amino acids and/or isotopically labeled peptide or proteins comprises at least one $^{12}C$ isotope and at least one $^2H$ isotope; and at least a portion of the isotopically labeled analytes, isotopic tagging reagents, isotopically labeled amino acids and/or isotopically labeled peptide or proteins comprises at least one $^{13}C$ isotope and at least one $^1H$ isotope. In an embodiment, for example, at least a portion of the isotopically labeled analytes, isotopic tagging reagents, isotopically labeled amino acids and/or isotopically labeled peptide or proteins comprises at least one $^{14}N$ isotope and at least one $^2H$ isotope; and at least a portion of the isotopically labeled analytes, isotopic tagging reagents, isotopically labeled amino acids and/or isotopically labeled peptide or proteins comprises at least one $^{15}N$ isotope and at least one $^1H$ isotope. In an embodiment, for example, at least a portion of the isotopically labeled analytes, isotopic tagging reagents, isotopically labeled amino acids and/or isotopically labeled peptide or proteins comprises at least one $^{16}O$ isotope; and at least a portion of the isotopically labeled analytes, isotopic tagging reagents, isotopically labeled amino acids and/or isotopically labeled peptide or proteins comprises at least one $^{18}O$ isotope. In an embodiment, for example, at least a portion of the isotopically labeled analytes, isotopic tagging reagents, isotopically labeled amino acids and/or isotopically labeled peptide or proteins comprises at least two $^{13}C$, $^2H$ or $^{15}N$ isotopes and at least one $^{16}O$ isotope; and at least a portion of the isotopically labeled analytes, isotopic tagging reagents, isotopically labeled amino acids and/or isotopically labeled peptide or proteins comprises at least one $^{18}O$ isotope and at least at least two $^{12}C$, $^1H$ or $^{14}N$ isotopes. In an embodiment, for example, at least a portion of the isotopically labeled analytes, isotopic tagging reagents, isotopically labeled amino acids and/or isotopically labeled peptide or proteins comprises at least two $^{13}C$, $^2H$ or $^{15}N$ isotopes; and at least a portion of the isotopically labeled analytes, isotopic tagging reagents, isotopically labeled amino acids and/or isotopically labeled peptide or proteins comprises at least one $^{34}S$ isotope and at least at least two $^{12}C$, $^1H$ or $^{14}N$ isotopes.

In an embodiment, for example, each of the isotopically labeled analytes are independently protein analytes or modified protein analytes having a different isotopic label. In an embodiment, for example, each of the isotopically labeled analytes are independently peptide analytes or modified peptide analytes having a different isotopic label. In an embodiment, for example, the isotopically labeled analytes have molecular masses selected from the range of 50 Da to 250 kDa, optionally selected from the range of 400 Da to 250 kDa, for example, for applications directed to protein and peptide analytes. In an embodiment, for example, the isotopically labeled analytes have molecular masses with 1 to 300 mDa of each other.

Methods of the invention provide an improvement on isobaric and SILAC-type quantification approaches, for example, via accessing much larger degrees for multiplexing. Enhance multiplexing in some embodiments results, at least in part, from compatibility of the methods for a large number of isotopically coded analytes, reagents, tagging agents, labels, standards, amino acids, etc. that are isotopologues that are distinguishable on the basis of mass to charge ratio using mass spectrometry analysis techniques. In an embodiment, the invention provides a multiplex method of analyzing the relative or absolute abundances of the analyte in the plurality of samples, for example a plurality of samples corresponding to difference in vivo or in vitro conditions. In an embodiment, for example, the method is for analyzing the relative or absolute abundances abundance of an analyte in at least 2 samples, optionally for some applications at least 4 samples, optionally for some applications at least 8 samples, optionally for some applications at least 20 samples. In an embodiment, for example, the step of providing the plurality of cell cultures comprises providing 2 to 20 cell cultures; and wherein the step of generating a sample for each of the cell cultures comprises generating 2 to 100 samples. In an embodiment, for example, the step of analyzing the isotopically labeled analytes for each sample using the mass spectrometry analysis technique providing the resolving power equal to or greater than 100,000 generates 2 to 150 of the independent and distinguishable mass spectrometry signals corresponding to the isotopically labeled analytes.

The present methods are compatible with a wide range of mass spectrometry techniques providing useful resolving powers, including techniques designed to probe the abundances of analytes in a plurality of samples, such as protein and peptide containing samples. In an embodiment, for example, a method of the invention further comprising the step of combining the samples characterized by a different isotopically labeled analyte prior to the step of analyzing the isotopically labeled analytes or isotopically labeled standards for each sample using the mass spectrometry analysis technique providing the resolving power equal to or greater than 100,000, thereby ensuring each sample undergoes similar sample preparation, purification, ionization, fragmentation and/or detection conditions. In an embodiment, for example, different isotopically labeled analytes or isotopically labeled standards for the plurality of samples are analyzed concurrently, for example, via purification steps and mass spectrometric analysis steps of a combination of a plurality of samples. In an embodiment, for example, the step of analyzing the isotopically labeled analytes for each sample comprises: generating one or more product ions for each of the isotopically labeled analytes, and measuring mass-to-charge ratios for at least a portion of the product ions using the mass spectrometry analysis technique providing the resolving power equal to or greater than 100,000. In an embodiment, for example, the step of analyzing the isotopically labeled analytes or isotopically labeled standards for each sample is carried out using a quadrupole ion trap, Fourier transform ion cyclotron resonance ion trap, a linear quadrupole ion trap, an orbitrap ion trap, a quadrupole mass analyzer or a time of flight mass analyzer.

In an embodiment, for example, the step of analyzing the isotopically labeled analytes or isotopically labeled standards comprises generating from the isotopically labeled analyte or isotopically labeled standards, for example, using electrospray ionization and MALDI techniques. In an embodiment, for example, the step of analyzing the isotopically labeled analytes or isotopically labeled standards comprises fragmenting ions generated from the isotopically labeled analytes or isotopically labeled standards, for example using one or more techniques selected from the group consisting of collision induced dissociation (CID), surface induced dissociation (SID), laser induced dissociation (LID), electron capture dissociation (ECD), electron transfer dissociation (ETD).

In an embodiment, for example, the method of the invention further comprises purifying proteins or peptides of the samples prior to the step of analyzing the isotopically labeled protein or peptide analytes for each sample, for example, via liquid phase chromatography (e.g., HPLC), gas phase chromatography, and/or capillary electrophoresis. In an embodiment, for example, the method of the invention further comprises frationating proteins or peptides of the samples prior to the step of analyzing the isotopically labeled protein or peptide analytes for each sample.

The methods of the present invention are useful for analyzing a variety of samples, including biological materials and samples derived from biological materials, such as biofluids, cell extracts, cell lysates, tissue extracts, etc. The methods of the present invention are useful for analyzing samples derived from in vivo biological materials. The methods of the present invention are useful for analyzing samples for proteomic analysis such as micro array samples and derived from in vitro assays. In embodiment, for example, the analyte is a protein, a peptide, a modified protein or a modified peptide. The methods of the present invention are useful for analyzing samples for analysis via gas chromatography—mass spectrometry methods, liquid chromatography—mass spectrometry methods and electrophoresis—mass spectrometry methods.

In another aspect, the invention provides a method for determining the abundance of an analyte in a sample comprising the steps of: (a) providing the sample having the analyte, wherein the analyte is a peptide or protein; (b) providing an isotopically labeled standard to the sample, wherein the analyte and the isotopically labeled standard are isotopologues; and wherein the difference of the molecular mass of the analyte and the isotopically labeled standard is less than or equal to 300 mDa; (c) analyzing the analyte and the isotopically labeled standard in the sample using a mass spectrometry analysis technique providing a resolving power equal to or greater than 100,000, thereby generating independent and distinguishable mass spectrometry signals for the analyte and the isotopically labeled standard of the sample; and (e) comparing the mass spectrometry signals for the analyte and the isotopically labeled standard of the sample, thereby determining the abundance of the analyte in the sample. As used herein, an "isotopically labeled standard" refers to an isotopically encoded compound provided to a sample to allow for absolute or relative quantification, such as an isotopically encoded peptide or protein that is provided to a sample in a known amount (e.g., having a known concentration). In an embodiment, for example, the isotopically labeled standard is an isotopically encode protein or peptide synthesized using one or more isotopically labeled amino acids, such as those provided throughout the present description. In an embodiment, the method of this aspect further comprises: (a) providing a plurality of samples, wherein each sample has the analyte; (b) providing the isotopically labeled standard to each of the samples; (c) analyzing the analyte and the isotopically labeled standard in each of the samples using a mass spectrometry analysis technique providing a resolving power equal to or greater than 100,000, thereby generating independent and distinguishable mass spectrometry signals for the analyte and the isotopically labeled standard of each sample; and (e) comparing the mass spectrometry signals for the analyte and the isotopically labeled standard of each sample, thereby determining the abundances of the analyte in the plurality of samples.

The invention also provides compositions of matter including any of the isotopically encoded compounds described herein, such as isotopically labeled amino acids, isotopically labeled standards, isotopically labeled analytes, isotopic tagging reagents, and/or isotopically labeled peptides or proteins described herein, provided in a purified state. In an embodiment, for example, the invention also provides compositions of matter including any of the isotopically encoded compounds described herein, such as isotopically labeled amino acids, isotopically labeled standards, isotopically labeled analytes, isotopic tagging reagents, and/or isotopically labeled peptides or proteins described herein, provided as an isotopically enriched composition.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1A—By one definition, the resolving power is m/$\Delta$m=500/1=500. FIG. 1B—By a second definition, the resolving power for the same pair of peaks is m/$m_{1/2}$=500/0.481=1.040. FIG. 1C—With the second definition, two peaks at m/z 500 and 501 are just barely discernible if the resolving power is 500.

FIG. 8A—The minimum m/z (Th) spacing that can be resolved at m/z 1,200 for mass resolutions from $10^3$ to $10^6$. FIG. 8B—Percentage of peptides that are resolved (FWOM) at varied mass resolutions ($10^3$-$10^6$).

FIG. 9. Possible isotopologues of Lysine when its mass is increased by 2 Da using various combinations of $^{13}C$, $^2H$, $^{15}N$, $^{18}O$ atoms. The mass range spanned by isotopologues depends on the number of heavy isotopes and the overall composition of the tagged molecule. For Lys+2 Da, a mass range of 18.5 mDa can be achieved.

FIG. 10A—Base peak chromatogram following 60 minute nLC-MS/MS analysis of tryptic yeast peptides. FIG. 10B—$MS^1$ scan #12,590, collected at 30K and inset of a selected precursor having m/z at 827. Also shown in FIG. 10B is the signal recorded in a subsequent high resolution $MS^1$ scan (480K), and the inset shows that the SILAC pair is concealed at typical resolution. FIG. 10C—MS/MS spectrum following CAD and ion trap m/z analysis of neutron encoded SILAC pair.

FIG. 11A—the dashed horizontal lines indicate the true ratio (grey=1:1, black=5:1) while boxplots demarcate the median (stripe), the 25th to 75th percentile (interquartile range, box), 1.5 times the interquartile range (whiskers), and outliers (open circles). From these data, it was concluded that NeuCode SILAC (referred to in the figure as OMNE SILAC) offers quantitative accuracy and precision that is not distinguishable from traditional SILAC. FIG. 11B—the percentage of time a PSM produced quantitative information for both NeuCode SILAC and traditional SILAC as a function of precursor intensity. Both methods produce quantitative data less frequently (at essentially the same rate) as precursor intensity is decreased; however, NeuCode SILAC generated 1,824 PSMs having precursor intensity less than $10^{5.5}$ (arbitrary units) while traditional SILAC only detected 522 in that same range. NeuCode SILAC permits increased sampling depth compared to traditional SILAC, while maintaining highly comparable quantitative accuracy and precision.

FIG. 15. Summary of possible isotopologues, mass ranges, and plexing capacity for +4 Da, +8 Da, and +12 Da Lysine isotopologues. Combination of these three labels could produce highly plexed quantitative capability.

FIG. 23A—Urea carbamylates the primary amines of peptides when exposed to heat. Peptides carbamylated with urea (labeled with either $^{13}C$ or $^{15}N_2$) are carbamylated with either a single $^{13}C$ or $^{15}N$ for each carbamyl group added. These carbamyl tags differ by 6.3 mDa per carbamylation site. FIG. 23B—The peptide LEQNPEESQDIK was carbamylated using each of the labeled ureas. Both the peptide n-terminus and the primary amine on the lysine chain were carbamylated thereby producing peptides that are 12.6 mDa apart. This difference was observed as a m/z difference of 6.6 for the peptide with charge (z)=2.

FIG. 24. A table showing common elements having stable heavy isotopes that can be incorporated into molecules. The third column provides the nominal mass of each isotope while the third column provides the exact masses. The fourth column provides the abundance ratios of the isotopes.

FIG. 25. Structures, chemical formulas, and coded element formulas for common amino acids which can be used as isotopic tagging reagents.

DETAILED DESCRIPTION OF THE INVENTION

Figure 1:
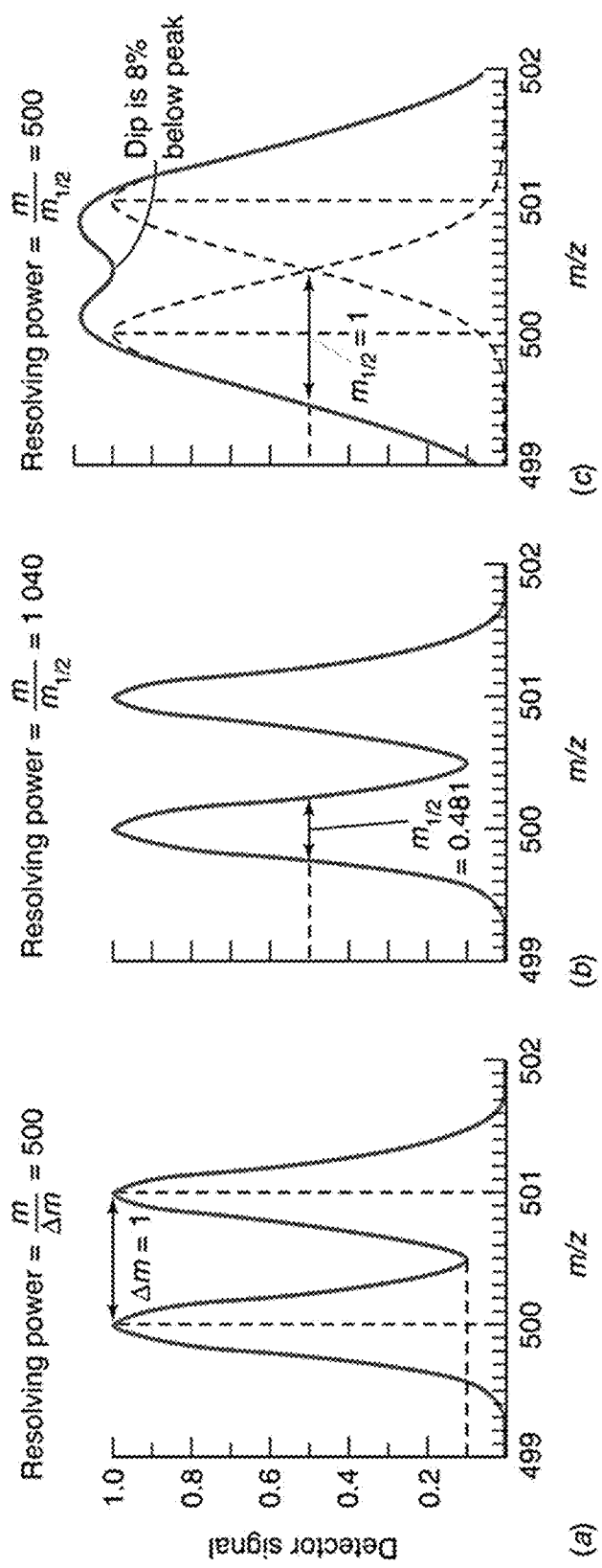
FIG. 1. Illustration how to calculate resolving power.

In general, the terms and phrases used herein have their art-recognized meaning, which can be found by reference to standard texts, journal references and contexts known to those skilled in the art. The following definitions are provided to clarify their specific use in the context of the invention.

In an embodiment, a composition or compound of the invention, such as an isotopically encoded compound including isotopically labeled analytes, isotopic tagging reagents, isotopically labeled amino acids, isotopically labeled standards and/or isotopically labeled peptides or proteins, is isolated or purified. In an embodiment, an isolated or purified compound is at least partially isolated or purified as would be understood in the art. In an embodiment, a composition or compound of the invention has a chemical purity of 90%, optionally for some applications 95%, optionally for some applications 99%, optionally for some applications 99.9%, optionally for some applications 99.99%, and optionally for some applications 99.999% pure. In some embodiments, an isolated or purified compound of the invention, such as an isotopically encoded compound including isotopically labeled analytes, isotopic tagging reagents, isotopically labeled amino acids, isotopically labeled standards and/or isotopically labeled peptides or proteins, is an isotopically enriched composition.

Many of the molecules disclosed herein contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "precursor ion" is used herein to refer to an ion which is produced during ionization stage of mass spectrometry analysis, including the $MS^1$ ionization stage of MS/MS analysis.

As used herein, the terms "product ion" and "secondary ion" are used interchangeably in the present description and refer to an ion which is produced during ionization and/or fragmentation process(es) during mass spectrometry analysis. The term "secondary product ion" as used herein refers to an ion which is the product of successive fragmentations.

As used herein, the term "analyzing" refers to a process for determining a property of an analyte. Analyzing can determine, for example, physical properties of analytes, such as mass, mass to charge ratio, concentration, absolute abundance, relative abundance, or atomic or substituent composition. In the context of proteomic analysis, the term analyzing can refer to determining the composition (e.g., sequence) and/or abundance of a protein or peptide in a sample.

As used herein, the term "analyte" refers to a compound, mixture of compounds or other composition which is the subject of an analysis. Analytes include, but are not limited to, proteins, modified proteins, peptides, modified peptides, small molecules, pharmaceutical compounds, oligonucleotides, sugars, polymers, metabolites, lipids, and mixtures thereof. An "isotopically labeled analyte" refers to an analyte that has been labeled with one or more isotopic labels, such as one or more stable heavy isotopes, for example, in a manner allowing isotopologoues of an isotopically labeled analyte to be distinguished on the basis of mass to charge ratio and quantitatively analyzed independently via mass spectrometry. For example, an "isotopically labeled analyte" includes analyte having one or more stable heavy isotopes of hydrogen, carbon, oxygen, nitrogen, sulfur, chlorine, bromine, and silicon, such as $^{13}C$, $^{15}N$, $^{2}D$, $^{17}O$, $^{18}O$, $^{34}S$, $^{37}Cl$, $^{81}Br$, $^{29}Si$, and $^{30}Si$.

As used herein, the term "ion source" refers to a device component which produces ions from a sample, for example, during mass spectrometry analysis. Examples of ion sources useful in the present methods include, but are not limited to, electrospray ionization sources and matrix assisted laser desorption/ionization (MALDI) sources.

As used herein, the term "mass spectrometry" (MS) refers to an analytical technique for the determination of the elemental composition, mass to charge ratio, absolute abundance and/or relative abundance of an analyte. Mass spectrometric techniques are useful for elucidating the composition and/or abundance of analytes, such as proteins, peptides and other chemical compounds. Mass spectrometry includes processes comprising ionizing analytes to generate charged species or species fragments, fragmentation of charged species or species fragments, such as product ions, and measurement of mass-to-charge ratios of charged species or species fragments, optionally including additional processes of isolation on the basis of mass to charge ratio, additional fragmentation processing, charge transfer processes, etc. Conducting a mass spectrometric analysis of an analyte results in the generation of mass spectrometry data for example, comprising the mass-to-charge ratios and corresponding intensity data for the analyte and/or analyte fragments. Mass spectrometry data corresponding to analyte ion and analyte ion fragments is commonly provided as intensities of as a function of mass-to-charge (m/z) units representing the mass-to-charge ratios of the analyte ions and/or analyte ion fragments. Mass spectrometry commonly allows intensities corresponding to difference analytes to be resolved in terms of different mass to charge ratios. In tandem mass spectrometry (MS/MS or $MS^2$), multiple sequences of mass spectrometry analysis are performed. For example, samples containing a mixture of proteins and peptides can be ionized and the resulting precursor ions separated according to their mass-to-charge ratio.

Selected precursor ions can then be fragmented and further analyzed according to the mass-to-charge ratio of the fragments.

As used herein, the term "interference" refers to a species detected in an analysis which interferes with the detection of a species or analyte of interest. Interference can refer to detection of a protein, or protein fragment, which is not a protein or protein fragment of interest and which interferes with the accurate detection or quantitation of the protein or peptide fragment of interest. Interference can be quantified as an interference ratio, such as a ratio of an amount of interference signal to an amount of analyte signal. In a mass spectral analysis, interference can be manifested as an interference peak which corresponds to detection of a species which is not an analyte of interest.

As described herein, "isolation" or an "isolation window" refers to a range of ions, such as precursor ions that is selectively separated and fragmented, manipulated or isolated.

As used herein, the term "species" refers to a particular molecule, compound, ion, anion, atom, electron or proton. Species include isotopically labeled analytes, isotopic tagging reagents, isotopically labeled amino acids and/or isotopically labeled peptide or proteins.

As used herein, the term "signal-to-noise ratio" refers to a measure which quantifies how much a signal has been corrupted by noise, or unwanted signal. It can also refer to the ratio of signal power to the noise power corrupting the signal. A ratio higher than 1:1 indicates more signal than noise and is desirable for some applications.

As used herein, the term "mass-to-charge ratio" refers to the ratio of the mass of a species to the charge state of a species. The term "m/z unit" refers to a measure of the mass to charge ratio. The Thomson unit (abbreviated as Th) is an example of an m/z unit and is defined as the absolute value of the ratio of the mass of an ion (in Daltons) to the charge of the ion (with respect to the elemental charge).

As used herein, the term "ion optic" refers to a device component which assists in the transport and manipulation of charged particles, for example, by the application of electric and/or magnetic fields. The electric or magnetic field can be static, alternating, or can contain both static and alternating components. Ion optical device components include, but are not limited to, ion deflectors which deflect ions, ion lenses which focus ions, and multipoles (such as quadruples) which confine ions to a specific space or trajectory. Ion optics include multipole RF device components which comprise multiple rods having both static and alternating electric and/or magnetic fields.

As used herein, the term "mass spectrometer" refers to a device which generates ions from a sample, separates the ions according to mass to charge ratio, and detects ions, such as product ions derived from isotopically labeled analytes, isotopic tagging reagents, isotopically labeled amino acids and/or isotopically labeled peptide or proteins. Mass spectrometers include single stage and multistage mass spectrometers. Multistage mass spectrometers include tandem mass spectrometers which fragment the mass-separated ions and separate the product ions by mass once.

As used herein, the term "disease state" refers to condition that can cause pain, dysfunction, distress, social problems, and/or death to a patient. Methods and systems described herein can be useful for diagnosis of a disease state.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides include, for example, polypeptides comprising 2 to 100 amino acid units, optionally for some embodiments 2 to 50 amino acid units and, optionally for some embodiments 2 to 20 amino acid units and, optionally for some embodiments 2 to 10 amino acid units.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

As used herein, the term "controller" refers to a device component which can be programmed to control a device or system, as is well known in the art. Controllers can, for example, be programmed to control mass spectrometer systems so as to carry out the methods as described herein. The invention includes mass spectrometers having a controller configured to carry out any of the methods described herein.

As used herein, the term "fractionated" or "fractionate" refers to the physical separation of a sample, as is well known in the art. A sample can be fractionated according to physical properties such as mass, length, or affinity for another compound, among others using chromatographic techniques as are well known in the art. Fractionation can occur in a separation stage which acts to fractionate a sample of interest by one or more physical properties, as are well known in the art. Separation stages can employ, among other techniques, liquid and gas chromatographic techniques. Separation stages include, but are not limited to, liquid chromatography separation systems, gas chromatography separation systems, affinity chromatography separation systems, and capillary electrophoresis separation systems.

Quantitative analysis in chemistry is the determination of the absolute or relative abundance of one, several, or all particular substance(s) present in a sample. For biological samples, quantitative analysis performed via mass spectrometry can determine the relative abundances of peptides and proteins. The quantitation process typically involves isotopic labeling of protein and peptide analytes and analysis via mass spectrometry.

"Fragment" refers to a portion of molecule, such as a peptide. Fragments may be singly or multiple charged ions. Fragments may be derived from bond cleavage in a parent molecule, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes whereby one or more side chains of amino acids are removed, or a modification is removed, or any combination of these processes. Fragments useful in the present invention include fragments formed under metastable conditions or result from the introduction of energy to the precursor by a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from a an analyte, such as a isotopically labeled analyte, isotopically labeled standard and/or isotopically labeled peptide or proteins, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum.

An "amine reactive group" of a tagging reagent can be any functional group able to react with an amine group of a peptide, protein or other molecule, thereby forming bond between the tagging reagent and the peptide, protein or other molecule.

An "amino acid" refers to an organic compound containing an amino group ($NH_2$), a carboxylic acid group (COOH), and any of various side chain groups. Amino acids may be characterized by the basic formula $NH_2CHRCOOH$ wherein R is the side chain group. Natural amino acids are those amino acids which are produced in nature, such as isoleucine, alanine, leucine, asparagine, lysine, aspartic acid, methionine, cysteine, phenylalanine, glutamic acid, threonine, glutamine, tryptophan, glycine, valine, proline, serine, tyrosine, arginine, and histidine as well as ornithine and selenocysteine.

As used herein, "isotopically labeled" refer to compounds (e.g., such as isotopically labeled amino acids, isotopically labeled standards, isotopically labeled analyte, isotopic tagging reagents, and/or isotopically labeled peptide or proteins) having one or more isotopic labels, such as one or more heavy stable isotopes. An "isotopic label" refers to one or more heavy stable isotopes introduced to a compound, such as such as isotopically labeled amino acids, isotopically labeled standards, isotopically labeled analyte, isotopic tagging reagents, and/or isotopically labeled peptide or proteins, such that the compound generates a signal when analyzed using mass spectrometry that can be distinguished from signals generated from other compounds, for example, a signal that can be distinguished from other isotopologues on the basis of mass-to-charge ratio. "Isotopically-heavy" refers to a compound or fragments/moieties thereof having one or more high mass, or heavy isotopes (e.g., stable heavy isotopes such as $^{13}C$, $^{15}N$, $^{2}D$, $^{17}O$, $^{18}O$, $^{33}S$, $^{34}S$, $^{37}Cl$, $^{81}Br$, $^{29}Si$, and $^{30}Si$.).

In an embodiment, an isotopically enriched composition comprises a compound of the invention having a specific isotopic composition, wherein the compound is present in an abundance that is at least 10 times greater, for some embodiments at least 100 times greater, for some embodiments at least 1,000 times greater, for some embodiments at least 10,000 times greater, than the abundance of the same compound having the same isotopic composition in a naturally occurring sample. In another embodiment, an isotopically enriched composition has a purity with respect to a compound of the invention having a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%. In another embodiment, an isotopically enriched composition is a sample that has been purified with respect to a compound of the invention having a specific isotopic composition, for example using isotope purification methods known in the art.

"Mass spectrometer resolving power, often termed resolution, is a quantitative measure of how well m/z peaks in a mass spectrum are separated (i.e., resolved). There are a variety of conventions to calculate resolving power. The IUPAC definition is:

$$\text{Resolving power } (R): R = m/\Delta m$$

FIG. 1A, is from Harris, Quantitative Chemical Analysis. This Figure and the equation above illustrate how to calculate resolving power (R) where m is the mass corresponding to the peak and $\Delta m$ is the spacing between that peak and the nearest neighbor peak. Another, utilized definition for resolving power is:

$$\text{Resolving power}(R): R = m/m\frac{1}{2}$$

In this definition (see, FIG. 1B), the m is the mass corresponding to the peak (m) and $m\frac{1}{2}$ is a variable refering to the full width at half maximum of the peak ($m\frac{1}{2}$=FWHM). With the second definition, two peaks at m/z 500 and 501 are just barely discernible if the resolving power is 500 (FIG. 1C). This method of calculating resolution is particularly useful as it provides a metric to assess peak width regardless of whether there is a nearby neighbor to compare it to. For the calculations contained in this writing we use this method of calculating resolution.

As used herein, the "coded element formula" of a compound refers to constituent elements of the compound, as well as the number of atoms of each element, that are suitable to be isotopically labeled with stable heavy isotopes, for example, to form isotopologues that may be analyzed via mass spectrometry in the present methods. The coded element formula of a compound will contain the same or fewer elements, as well as the same or fewer number of atoms of each element, than the chemical formula of the compound due to the fact that some atoms of the compound may not be suitable to be isotopically labeled to form isotopologues for use in the present methods. For example, H atoms of the compound that are easily exchangeable with H atoms of solvents, such as water, may not be suitable to be isotopically labeled in the present methods because such exchange processes may degrade the isotopic signature of isotopically labeled analytes and/or standards. Similarly, if the compound contains leaving groups or reactive groups which are not ultimately present in the isotopically label species, such as the isotopically labeled analytes, isotopic tagging reagents, isotopically labeled amino acids and/or isotopically labeled peptide or proteins, then atoms within the leaving groups or reactive groups would also not be suitable to be isotopically labeled in the present invention and, thus, would not be included in the coded element formula. Certain elements of such reactive groups and/or leaving groups, for example, may be exchanged or otherwise removed or lost in the chemical reaction between the tag and the analyte, and, hence would not result in incorporation in the isotopic label. For example, in one embodiment, the chemical formula for lysine is: $C_6H_{14}N_2O_2$ while the coded element formula for lysine is: $C_6H_9N_2O$. In one embodiment, H atoms that are easily exchangeable with H atoms of solvents are not included in a compound's coded element formula. For instance, in one embodiment, the H atoms of at least some, and optionally all of, —OH, —SH, —NH—, and —NH$_2$ groups would be part of a compound's chemical formula but would not be part of the compound's coded element formula. In a further embodiment, the O atoms of at least some, and optionally all of, —OH groups would not be part of the compound's coded element formula. In one embodiment, all carbon atoms in a compound, particularly an amino acid, would be part of the compound's coded element formula. In one embodiment, all nitrogen atoms in a compound, particularly an amino acid, would be part of the compound's coded element formula.

Brief Description of Proteome Quantification

There are currently two main methods for global proteome quantification. The first is SILAC (stable isotope labeling with amino acids in cell culture), which is very popular and has been used for nearly a decade. In SILAC, $^{13}C$ atoms are incorporated into amino acids so that these amino acids (called heavy amino acids) are 3 to 6 Da heavier than the normal amino acids. Cells are then grown in separate cultures, one culture containing the heavy amino acids and the other culture containing normal amino acids.

New proteins synthesized in the cultures incorporate either the heavy amino acids or the normal amino acids and the cells are then treated with a perturbation and the proteins are combined. After enzymatic digestion, the peptides produced have the same sequence, but have slightly different masses because of the $^{13}C$ atoms in the heavy amino acids. When analyzed by MS, two discrete peaks are seen for the same peptide—a light peak and a heavy peak. These peaks are usually separated by approximately 3 to 8 Da. However, it has been very difficult to multiplex (compare 4 or more samples simultaneously) with SILAC because a minimum of 3 Da separation between the labeled peptides is required to minimize isotopic distribution overlap. With a maximum range of 10 Da, plexing is limited to roughly 3 samples.

Because of the lack of ability to multiplex (>3), researchers have become increasingly excited about isobaric tagging (TMT or iTRAQ commercial products). Isobaric tagging involves the addition of a tag to the analyte peptides. Isobaric tags are designed to have three components: (1) a reactive group for attachment to the analyte, (2) a balance group, and (3) an ionizable reporter group. The balance and reporter groups are designed with a distribution of stable isotopes so that they have the same mass with approximately 6 to 8 different tags. When the samples elute into the mass spectrometer, the tagged samples all have the same mass so a single peak is obtained. The targets in this peak are isolated and the reporter group is cleaved. Each reporter group has a mass that is approximately 1 Da separated from the next reporter group so the 6-8 analytes become distinguishable using MS/MS. However, there are two genuine problems with isobaric tagging. First, targets are isolated with a broad window, approximately 2 to 3 m/z, and so interferences get co-isolated, then co-fragmented during MS/MS and produce reporter peaks at the same m/z values, leading to a lower dynamic range and quantitative accuracy. The second problem is that a MS/MS scan must be acquired to get quantitative data. This becomes problematic with multiple replicates since the overlap between what gets isolated for MS/MS in one experiment to the next can be low.

The developers of the TMT isobaric tags have recently published work showing that by swapping a $^{12}C$ for a $^{13}C$ and concomitantly a $^{15}N$ for a $^{14}N$ in the TMT reagents, one can achieve a new reagent that has a 6 mDa mass difference due to the energetics of the neutron binding difference between N and C. This slight mass difference makes them distinguishable using high resolution mass spectrometers. With this approach they have expanded their TMT reagents from a 6-plex to an 8-plex system.

Brief Description of Present Tagging System

The present invention discloses a new method and customized tagging reagents for MS proteome quantification generally called "neutron encoded mass tagging" or "NeuCode". This method is also referred to herein as "offset mass neutron encoding" or "OMNE". In this method, the neutron mass difference between heavy isotopes, such as N and C, could be coupled with amino acids and novel reagent tags to create a MS1-based quantification method that is superior to both conventional SILAC and isobaric tagging in many ways. This idea was initially tested using two +8 Da heavy lysine amino acids, one with six $^{13}C$'s and two $^{15}N$'s and another with eight deuteriums ($^2H$).

Figure 2:
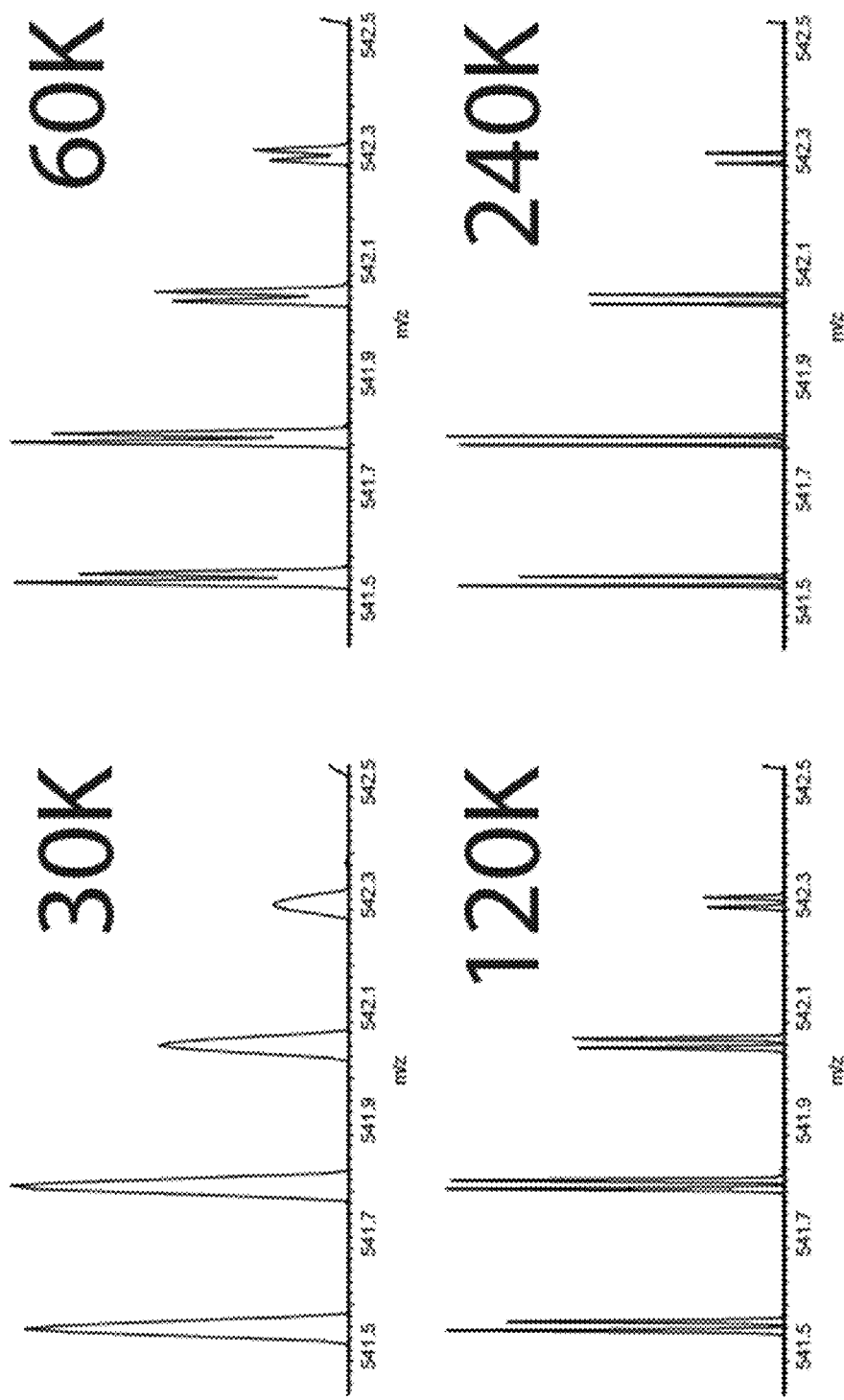
FIG. 2. Mass spectrometry results for a selected lysine labeled pair of peptides at varying resolution settings. At the typical operating resolution of the Orbitrap MS system (30,000) the two NeuCode labeled peptides are indistinguishable and appear as one species. When analyzed at 240,000 resolving power, the pair is baseline resolved. Operation of the system at its highest resolution—480,000—produced baseline resolution of nearly every peptide species detected in the complex mixture.

FIG. 2 illustrates results for selected lysine labeled pair of peptides at varying resolution settings. At the typical operating resolution of the Orbitrap MS system (30,000) the two NeuCode labeled peptides are indistinguishable and appear as one species. When analyzed at 240,000, however, the pair is baseline resolved and one can determine the relative abundance of each analyte.

These neutron tags can be incorporated into amino acids and then the modified amino acids used during cell culture similar to SILAC. Using such a tagging system would alleviate the spectral complication problem associated with SILAC and allow for increased multiplexing. Initial calculations for the incorporation of nine different heavy isotopes into the amino acid Lysine (either $^{15}N$, $^{13}C$, $^2H$, or $^{18}O$ atoms) showed that the construction of 41 different isotopologues that have masses spanning only 41.4 mDa is possible (shown in FIG. 3).

In addition, this tagging system may be used with novel tagging reagents and are not limited to SILAC related methods. This would allow for analysis of tissues and other body fluids that are not compatible with tissue culture. NHS ester technology is a widely used chemistry to link tags onto peptides for proteomic analysis. Both commercial isobaric tagging methods (iTRAQ and TMT) use this approach. Accordingly, the present tagging system could utilize a dipeptide-like tag, or other tags able to bind to peptides, that is simple to synthesize that also uses the NHS ester linkage chemistry. Unlike isobaric tags, however, the present tagging system would not require specialized designs that incorporate reporter groups, linkers and charge sites. Instead the tags of the present invention are designed to remain bound to the peptide and to provide a quantitative measure only when examined under high resolution conditions. An initial version of this tag was tested in silico and shown to enable a 5-plex analysis at current MS resolving powers. The resolution of mass spectrometry systems are reasonably expected to double within the several years which means this tag could then enable a 9-plex analysis.

Thus, using this tagging system with cell culture allows for greater multiplexing compared to conventional SILAC methods, while also ameliorating the spectral complexity problem associated with SILAC. Using this tagging system with novel reagent tags allows for similar multiplexing compared to isobaric tagging methods, but without the problems caused by interferences due to co-isolation or the need to perform MS/MS.

EXAMPLES

Example 1

Background of SILAC and Isobaric Tagging Methods and Overview of Neutron Encoded Mass Tagging Protein identification technologies have rapidly matured such that constructing catalogs of the thousands of proteins present in a cell using mass spectrometry is now relatively straightforward. Knowing how the abundance of these molecules change under various circumstances, however, is not straightforward. Stable isotope incorporation is a central component of many MS-based protein quantification strategies. Presently, there are two main approaches to accomplish this. The first is to metabolically introduce heavy stable isotopes (i.e., $^{13}C$, $^{18}O$, $^{15}N$, $^{2}H$) into proteins during cell growth. In SILAC, amino acids that incorporate stable isotopes, which are typically 4 or 8 Da heavier than the normal amino acids, are included in the cell culture media so that all synthesized proteins incorporate the heavy amino acids. Combination of cells grown on heavy and light media produce identical proteomes except that each peptide that includes a heavy amino acid that differs by +4 Da from its light counterpart. Using this technique to proteomes can be simultaneously compared by MS analysis of the heavy and light peptides.

Isobaric tagging is an elegant solution to this problem, allowing relative quantification of up to eight proteomes simultaneously. Further, unlike metabolic labeling approaches, it is compatible with mammalian tissues and biofluids. Despite its potential, isobaric tagging has not been widely embraced for large-scale studies—chiefly because of the problem of precursor interference. This problem does not exist for SILAC because abundance measurements are obtained from high-resolution survey mass spectra (MS1). Even for very complex samples having hundreds of co-eluting peptides, highresolving power mass analyzers can easily distinguish the target from neighboring peaks less than 0.01 Th away.

Isobaric tags are designed to have three components: (1) a reactive group for attachment to the analyte, (2) a balance group, and (3) an ionizable reporter group. The balance and reporter groups are designed with stable isotopes so that they have the same aggregate mass with 6 to 8 different tags. In this way 6 to 8 samples are co-analyzed. When the tagged samples elute into the mass spectrometer, the samples all will have the same mass so just one peak is produced. When MS/MS is performed, the tagged peptide is fragmented causing the reporter group to cleave off and be detected. Each reporter group has a mass that is approximately 1 Da separated from the next reporter group, so the 6-8 analytes become distinguishable in MS/MS analysis. From this, the abundance of the analyte in each of the 6-8 conditions can be determined.

MS1 vs. MS2 Quantification Quality

SILAC is the most widely used multiplexing strategy for protein quantification. By obtaining quantitative data from MS1 scanning, SILAC can offer improved quantitative performance over isobaric labeling approaches for three main reasons. First, $MS^1$ abundance measurements allow averaging of several data points per peptide. Isobaric tagging, on the other hand, typically draws all information from a single MS/MS scan. A second benefit of $MS^1$ vs. $MS^2$-based quantitation is that upon peptide identification, quantitative information for that peptide can be extracted from $MS^1$ data alone in each replicate. Isobaric tagging, however, requires both the collection of an $MS^2$ scan and an identification in each replicate analysis. With a ~50-75% run-to-run overlap in spectral identifications, this caveat limits statistical significant testing to the subset of peptides/proteins identified across multiple experiments. The third advantage of $MS^1$-centric quantification is significantly improved quantitative accuracy. Specifically, isobaric tagging suffers from the well-documented problem of precursor interference—the co-isolation of impurities. This problem does not exist for SILAC because abundance measurements are obtained from high-resolution $MS^1$ scans and even for very complex samples having hundreds of co-eluting peptides, high-resolving power mass analyzers can easily distinguish the target from neighboring peaks less than 0.01 m/z away. In the isobaric tagging approach, the target peptide is isolated at much lower resolution (typically 1-3 m/z), then dissociated to produce reporter tags. Therefore, the quantitative signal in the reporter region is compiled from every species in the isolation window. Co-isolation of multiple species is the rule, not the exception for even highly fractionated samples.

Multiplexing

Even with these fundamental limitations, two essential advantages—tissue compatibility and high multiplexing capacity—propel the widespread use of isobaric tagging. Since isobaric tagging is a chemical, rather than metabolic, labeling strategy one can easily compare up to 8 mammalian tissue samples. The ability to analyze biological fluids and tissues is vital for the application of proteomics to translational medicine. Beyond the obvious direct analysis of human tissues, there are countless mammalian models of disease, e.g., cancer, diabetes, multiple sclerosis, etc., where proteome characterization requires tissue-compatible technologies. Advancing quantitative proteomics from cell culture toward more complex animal-based disease models, requires increased replicate analysis and, typically, several biological states. In a simple experiment examining the effects of caloric restriction (CR) and the deacetylase Sirt3 in mice, there are four conditions—wt (control), Sirt3 knockout, wt CR, and Sirt3 knockout CR. For statistical significance testing, at least 3 animals in each condition must be analyzed for a minimum of 12 samples. And this experiment only considers analysis of one tissue, one age, and one strain. Thus, the ability to achieve expanded multiplexed proteomic comparisons with high quantitative accuracy and reproducibility will deeply impact modern biology and medicine.

Accuracy Issues with MS2 Quantification are not Acceptably Resolved

Even though MS2 approaches already deliver multiplexing capacity, data quality and quantification overlap (reproducibility, see above) are still require improvement. Efforts have been made to overcome these shortcomings. For example, ion/ion reactions for gas-phase precursor purification have been explored as well as MS3-based strategies. Despite improved quantitative accuracy on model systems (approximately −20% accuracy bias, i.e., true value 10:1 detected as 8:1), duty cycle, sensitivity, and availability of both approaches are problematic. Both MS3 and QuantMode acquisition methods reduce duty cycle and, consequently, generate about 50 to 70% of the identifications as compared to typical shotgun analyses. The sensitivity of either approach is likewise restricted by limited sampling depth (duty cycle) and by reduced reporter ion intensities (purification losses).

Finally, both require the presence of an ion trap and Quant-Mode requires ETD capability. Experience with these purification approaches indicates that there is no straightforward remedy to the duty cycle, sensitivity, and compatibility issues outlined above. These problems, combined with the irreproducibility of $MS^2$-based quantification over multiple replicate analyses (see above), strongly suggest that developing a multiplexed $MS^1$-centric approach is key to advancing quantitative proteomics and, in particular, its application to translational medicine.

MS1 Multiplexing—The Path Forward

Unfortunately, achieving multiplexed analysis with $MS^1$-based technology has been challenging. SILAC provides a means to make binary or ternary comparisons and by interlacing these experiments, higher-order comparisons can be obtained; however, obtaining such measurements are laborious and only reported by a handful of expert laboratories. SILAC is practically limited to triplex comparisons because a minimum of 4 Da separation between the labeled peptides is needed to minimize isotopic distribution overlap. This spacing is greatly compressed when precursor charge is 3 or greater.

Figure 4:
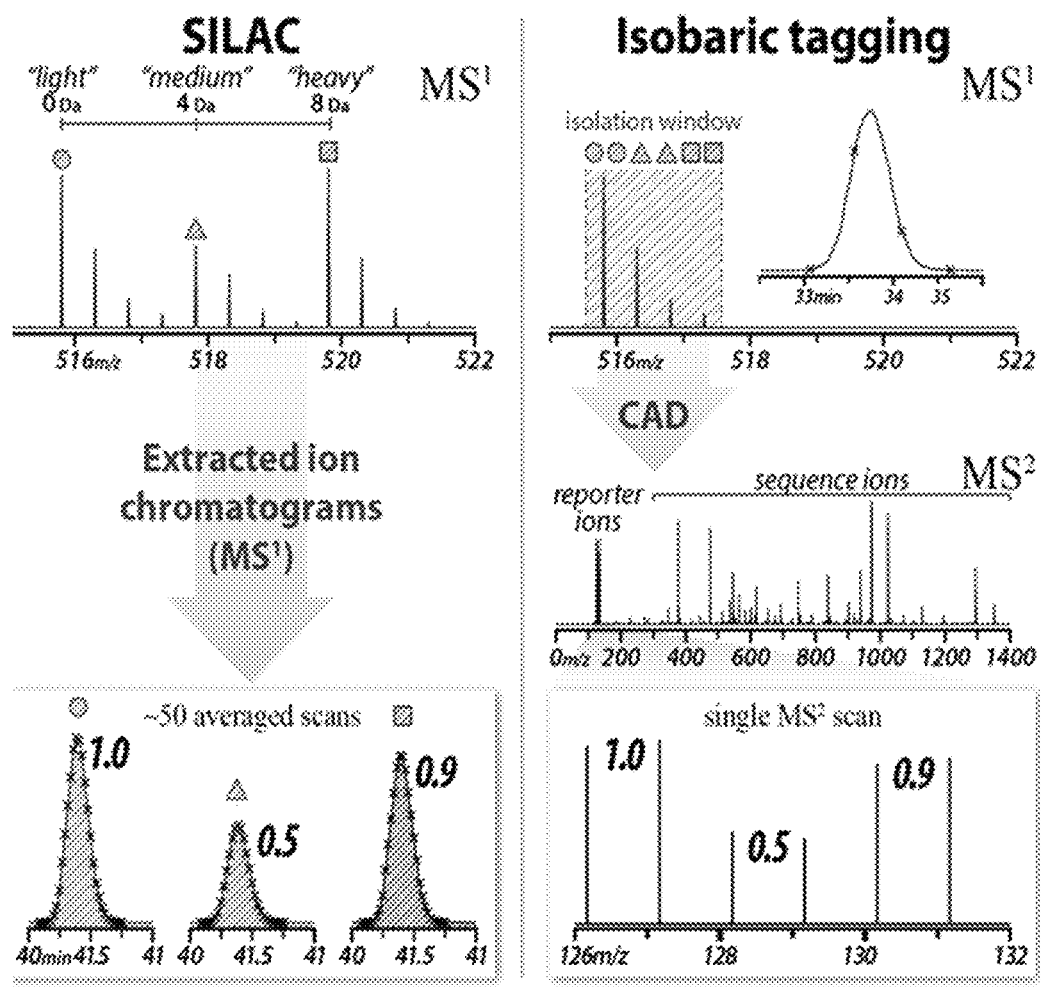
FIG. 4. Overview of SILAC and isobaric tagging methods. In SILAC, three isotopic clusters are generated: "light" (0 added Da), "medium" (4 added Da) and "heavy" (8 added Da). These signals are distinguished during MS1 analysis and the ion chromatograms for each are extracted over the entire elution profile so that quantitative data is averaged over ~50 scans per peptide. In isobaric tagging all plexes have the same mass so that only one isotopic cluster peak is generated during MS1. During collisionally activated dissociation (CAD) fragmentation during MS2, the tags cleave and reporter ion signals are detected. These reporter ion signals can be integrated to determine relative abundance.

In SILAC multiple isotopic clusters are generated, typically 4 Da apart, for each additional plex that is quantified—up to three-plex (see FIG. 4). These signals are distinguished during MS1 analysis and the ion chromatograms for each are extracted over the entire elution profile so that quantitative data is averaged over ~50 scans per peptide. In isobaric tagging all plexes have the same mass so that only one isotopic cluster peak is generated during MS1. During MS2 the tags cleave and reporter ion signals are detected. These can be integrated to determine relative abundance. This approach, however, often draws quantitative data from a single scan and an MS2 event is required.

The ability to introduce heavy isotopes into Lys for SILAC is limited by its composition (six C atoms and 2 N atoms); hence, the largest commercially available heavy version is +8 Da. A handful of attempts to increase SILAC plexing have been reported, but require non-trivial computation and the presence of Arg within each peptide. These limitations have precluded their widespread adoption. A second problem of SILAC plexing is the increased spectral complexity. Specifically, for each peptide every SILAC channel produces an additional set of m/z peaks. MS/MS sampling of more than one of these peaks produces redundant identifications and, consequently, consumes MS/MS bandwidth so that lower abundance m/z peaks often do not get sampled. Overall such increased complexity reduces proteome coverage.

Isobaric Neutron Encoded Mass Tagging

The developers of the TMT isobaric tags have recently discovered that by swapping a $^{12}C$ for a $^{13}C$ and concomitantly a $^{15}N$ for a $^{14}N$ in the TMT reagents can achieve a new reagent that has a 6 mDa mass difference. The mass change results from the discrepancy in energetics of neutron binding between N and C and can be distinguished with a mass resolution of 50,000 at m/z 130. By implementing this approach, the TMT reagents can be expanded from a 6-plex system to an 8-plex system. This new TMT isobaric concept still relies upon $MS^2$-based quantification and all does not resolve the issues outlined above. The present invention advances this neutron encoding concept to develop an ultraplexed (up to 45-plex) $MS^1$-based quantification technology that combines the best aspects of both SILAC and isobaric tagging.

Differences Between Neutron Coding and Traditional Isobaric Tagging

Traditional isobaric tagging relies on introduction of chemical tags to peptides. The chemical tags are designed to have three specific components: a reactive group, a balance group, and a reporter group. During MS1 analysis, analytes labeled with isobaric tags appear as a single m/z peak and quantitative information cannot be obtained from MS1 analysis—no matter how high the resolving power. Quantitative data is only retrieved upon fragmentation of the precursor ions by collisional activation. During this process the charged reporter group is released from the balance group and produces a detectable m/z peak at a defined mass. Isobaric tags currently offer up to 8 channels of quantitation. Reporter ions vary in mass between each channel by 1 Da. For example, m/z 126, 127, and 128. Thus, quantitative data can only be measured by first performing collisional activation and by monitoring the product ions by MS/MS.

Limitations of this approach are many in number. First, since no data is derived from the MS1 scan, if an MS/MS event is not acquired for a given precursor, then no quantitative data of any kind is recorded. Second, all precursors within the MS/MS isolation window (usually about 1-3 m/z) are subjected to collisions and produce the reporter tags. This means that the quantitative signal is the convolution of all the precursors within the isolation window. This shortcoming severely limits quantitative accuracy. Third, isobaric tagging is only compatible with one type dissociation collisional activation. Key to isobaric tagging is that the reporter group be cleaved from the balance group and detected. For commercial products these have been optimized for collisional activation; however, many types of dissociation are available and include electron capture and transfer dissociation along with those that use photons.

The neutron encoding strategy of the present invention embeds very subtle mass differences into analytes for quantitative purposes. These differences are so small (<50 mDa) that they cannot be distinguished at normal MS resolving powers. Analysis under high resolution conditions, however, (>100,000) can separate these closely spaced peaks and reveal quantitative information. Neutron codes can be introduced by growing cells on custom amino acid isotopologues or by placing chemical tags onto peptides. For the latter case the chemical reagents do not have the features of a traditional isobaric tag, i.e., no reporter or balance group. Instead the tag is simply a delivery vehicle to embed a neutron fingerprint onto each analyte. This fingerprint is then only detected when the sample is analyzed under high resolution conditions, typically in the MS1 scan.

Figure 5:
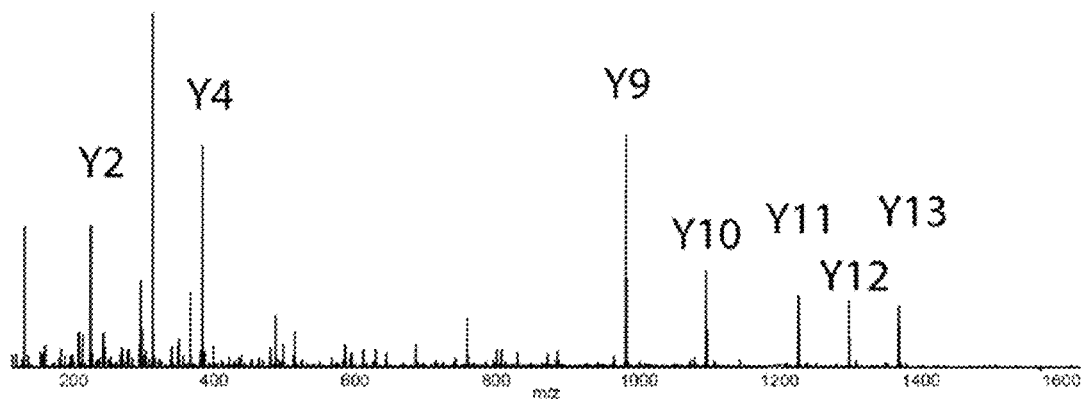
FIGS. 5-7. MS/MS scans of a NeuCode labeled peptide. At low resolution, such as shown in FIG. 5, the quantitative information is invisible and the peaks appear as single peaks. At high resolution (FIG. 6), however, these peaks are revealed as multiple peaks providing additional data (FIG. 7). These data are reflective of abundance and could be used for quantification.
Figure 6:
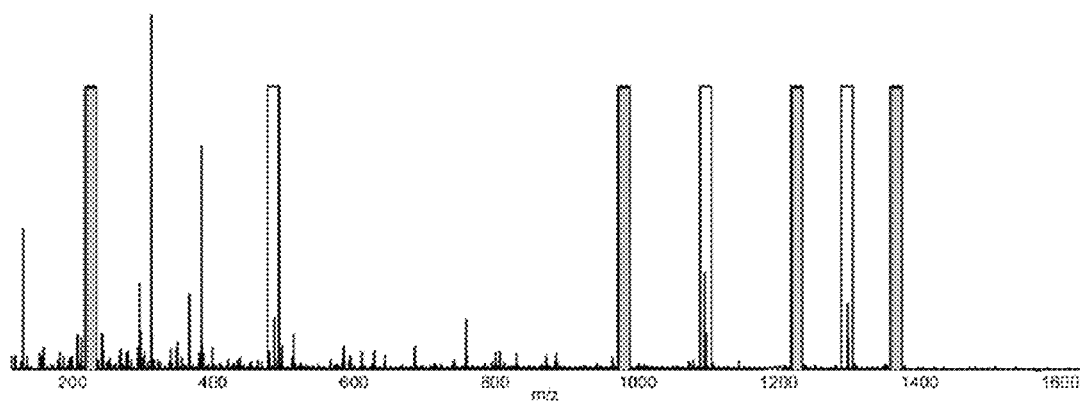
Figure 7:
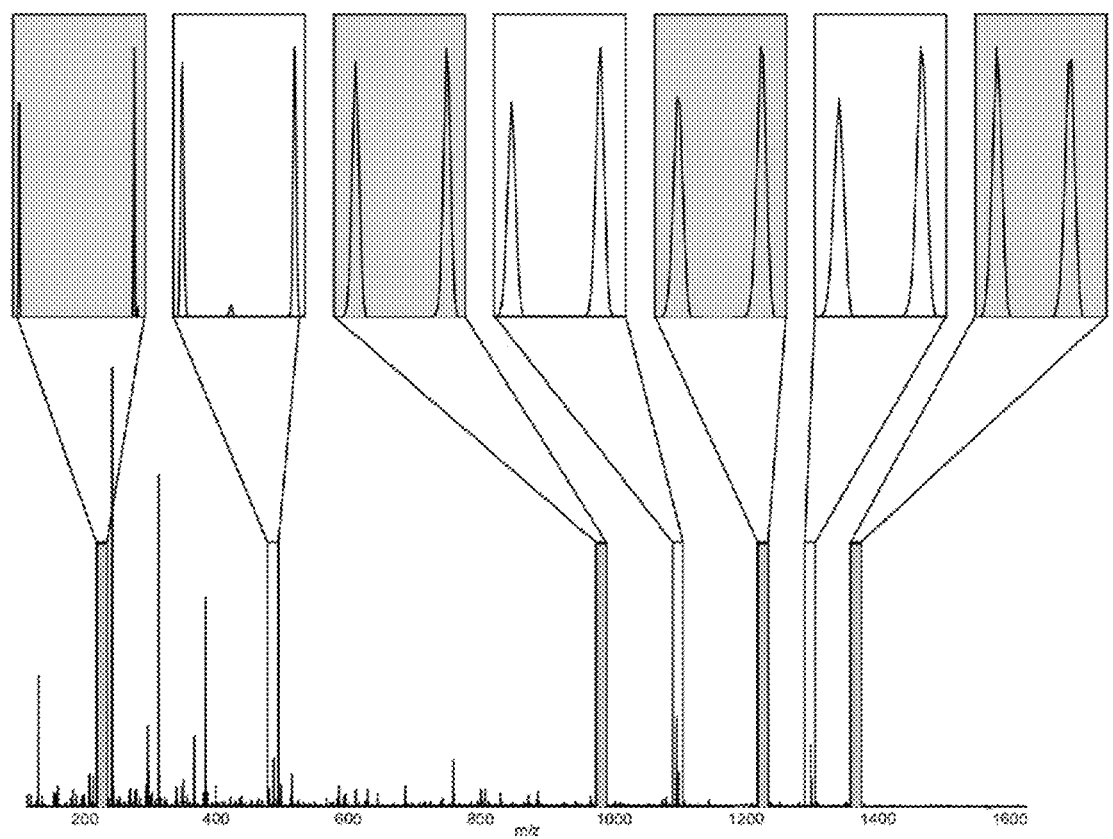

FIGS. 5-7 show MS/MS scans of a neutron encoded labeled peptide. At low resolution, such as shown in FIG. 5, the quantitative information is invisible and the peaks appear as single peaks. At high resolution (FIG. 6), however, these peaks are revealed as multiple peaks providing additional data (FIG. 7). These data are reflective of abundance and could be used for quantification.

Another major difference from traditional isobaric tagging is that the neutron encoding signatures of the present invention stay with the peptide after dissociation. Dissociation can be accomplished by any fragmentation method. Product ions that result from the cleavage of the peptide backbone that contain the neutron coding tag, either the amino acid or the chemical tag, will be detected if analyzed under high resolution conditions (>100,000). Unlike traditional isobaric tagging, these signals do not occur at the same mass for every precursor (the reporter fragment mass), they occur along with the backbone fragments of the peptide and at every fragment that contains the neutron tag. This means that quantitative information can also be gathered from MS/MS spectra, but only if scanned under high resolution and at m/z peaks where the peptide fragments. Thus, for neutron coding, the interference problem of traditional isobaric tags is eliminated.

NeuCode Overview

The neutron encoded mass difference that has been exploited to expand the plexing capacity of isobaric tagging can be harnessed to create an $MS^1$ quantification method—one that is superior to both conventional SILAC and isobaric tagging.

To determine the feasibility of NeuCode, a library of 105,067 identified tandem mass spectra was surveyed and it was determined that 99.4% of the peptide precursors had m/z values of 1,200 or less. Next, the minimum resolvable difference (full width at 1% max, FWOM, i.e., only 1% overlap in peak areas) was calculated for a 1,200 Th precursor as a function of resolving power ranging from $10^3$ to $10^7$ (FIG. 8A). The current commercially available Orbitrap is capable of 480,000 resolving power, enabling separation of precursors spaced as narrowly as 11.1 mTh. This value falls to half that (5.6 mTh) with the highest reported Orbitrap resolution of 960,000. The average precursor has a much lower m/z (~750) and can be resolved at 7.0 and 3.5 mTh at 480,000 and 960,000, respectively. Using these calculations as a guide, the peptide library was used to model the percentage of the peptidome that would be quantifiable (i.e., separated at FWOM) when labeled at intervals of 12, 18, and 36 mDa (FIG. 8B). This takes into account the diversity of precursor m, z, and m/z that is typically observed in a shotgun experiment. These data demonstrate that at a resolving power of 480,000, >85% of identified peptides can be quantified (i.e., resolved) when spaced 18 mDa apart. At 960,000 resolving power, >90% coverage was achieved with 12 mDa spacing.

These data confirm that with the current commercial Orbitrap resolving power capability of 480,000, detection and identification using the NeuCode tagging strategy could be achieved for nearly the entire peptidome with ~18 mDa spacing between labeled peaks. At the highest reported Orbitrap resolving power of 960,000, similar coverage could be achieved with only 12 mDa peak spacing. It was next determined what spacing ranges and gap sizes could be achieved using the common elements found in biological systems—i.e., C, H, N, and O. FIG. 9 presents all theoretical isotopologues of the amino acid Lysine that contains a +2 Da offset by incorporation of $^{13}C$, $^2H$, $^{15}N$, $^{18}O$ in various combinations. With just a modest mass difference of 2 Da, 7 isotopologues can be created spanning a mass range of 18.5 mDa (referred to herein as the offset mass) offering either du-plex or tri-plex tagging (i.e., ~9 and 18 mDa spacing). Incorporation of more stable isotopes, +8 Da, can deliver offset mass ranges in excess of 50 mDa. Together with the theoretical calculations above, it was concluded that sufficient offset masses can be introduced to allow implementation of the NeuCode strategy with currently available mass resolving power.

Neutron-Encoded Amino Acids for Multiplexed SILAC (NeuCode SILAC)

Rationale:

Synthesis of amino acids that incorporate the NeuCode labeling strategy will produce SILAC reagents that greatly expand (4-10×) the multiplexing capability of the gold standard protein quantification technique—SILAC. This added plexing capacity will neither increase $MS^1$ spectral complexity nor reduce peptide identification rate, as compared to the conventional SILAC strategy.

Hypothesis:

Using conventional multi-Da isotopic spacing limits SILAC to binary and ternary comparisons. Highly multiplexed experiments allow measurement of time-course experiments, permit collection of biological replicate data, and enable direct comparison of transcriptomic and proteomic data. By incorporating various isotopologues of Lysine, each differing by approximately 10 mDa, a set of amino acids is created that yield 12 channels for quantification when combined. These amino acids deliver a greatly increased level of multiplexing and performance compared to SILAC.

Preliminary Data:

To test the hypothesis that isobaric isotopologues of amino acids can allow SILAC hyperplexing, two +8 Da heavy lysine amino acids were purchased, one with six $^{13}C$ atoms and two $^{15}N$ atoms and the other with eight $^2H$ atoms. These two isotopologues differ in mass by 36 mDa and are easily distinguished at the commercially available resolution of current Orbitrap systems (480K). Two yeast cultures (BY4741 Lys1Δ) were grown in defined synthetic complete drop out media supplemented with either the "light" lysine (+0 Da), "heavy 1" $^{13}C_6/^{15}N_2$Lys (+8.0142 Da) or "heavy 2" $^2H_8$ (+8.0502 Da). To ensure complete Lys incorporation, cells were propagated for at least 10 doublings, then harvested in mid-log phase by centrifugation at 3,000×g for 3 minutes. Cell pellets were re-suspended in 5 mL lysis buffer and protein was extracted by glass bead milling. Protein from lysed yeast cells were reduced, alkylated, and digested with endo-LysC. Next, three traditional SILAC samples were prepared in known mixing ratios by combining the "light" (+0 Da) and "heavy 1" (+8 Da) labeled peptides in ratios of 1:1 and 1:5 by mass. NeuCode SILAC ratios were prepared exactly the same, except by using "heavy 1" (+8.0142 Da) and "heavy 2" (+8.0502 Da) labeled peptides.

Figure 10:
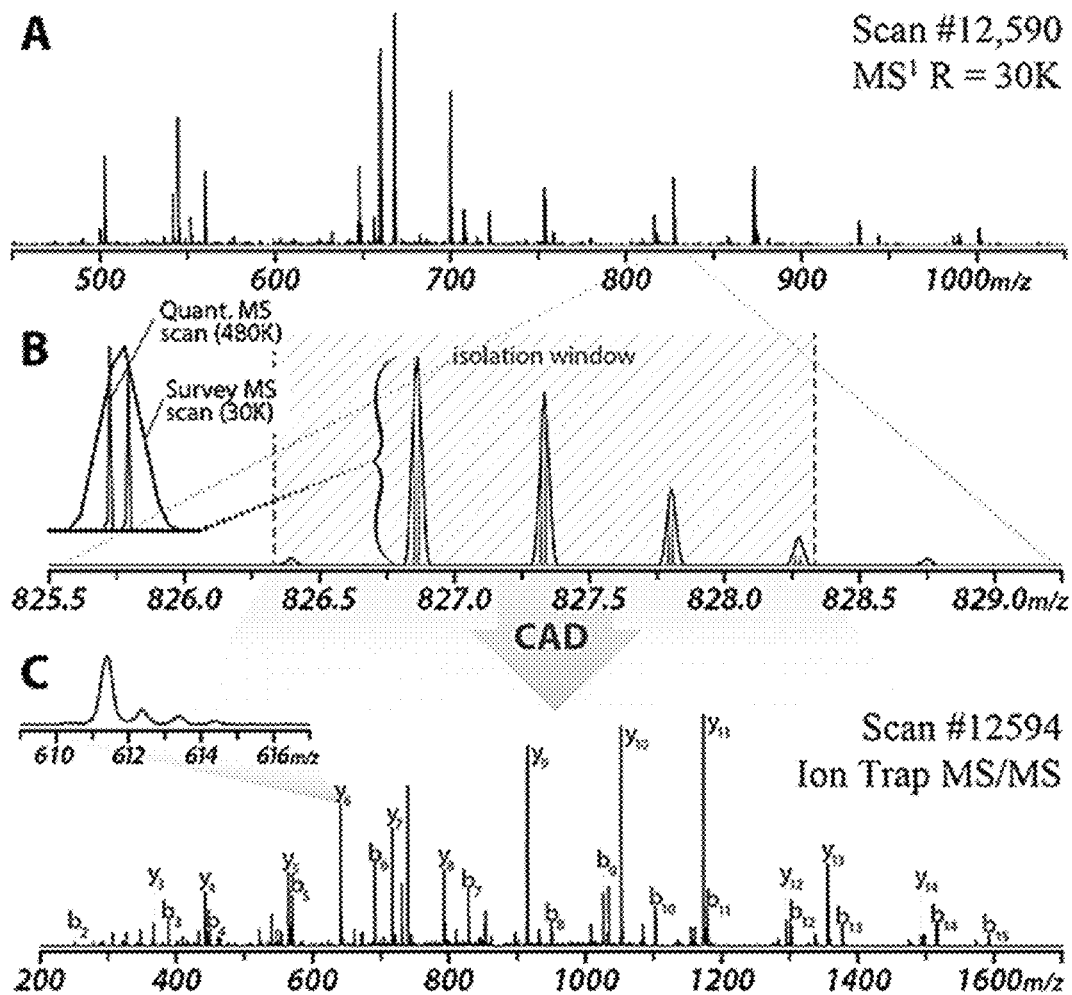
FIG. 10. Preliminary data using NeuCode SILAC method with two Lys isotopologues differing by 36 mDa.

Samples from each method (i.e., NeuCode SILAC and traditional SILAC) were independently loaded onto a capillary nLC column and gradient eluted into an ion trap-Orbitrap hybrid MS over 60 minutes. For traditional SILAC, $MS^1$ analyses were performed at a resolving power of 30,000 with the top 10 most intense precursors selected for MS/MS analysis (ion trap CAD). For NeuCode SILAC analysis, an additional $MS^1$ scan was implemented at a resolving power of 480,000 immediately following the first 30,000 resolving power full scan. The high resolution scan distinguished the NeuCode SILAC pairs—effectively decoding the embedded quantitative data. Example spectra from that analysis are presented in FIG. 10; panel A displays a $MS^1$ scan (R=30K) and panel B presents the isotopic cluster of a selected precursor at m/z 827. Here, the signal that is generated under the typical 30K resolving power and the high resolution quantification scan (480K) are plotted. Both "heavy" Lysine isotopologues that are spaced only 36 mDa apart were observed. The very close m/z spacing of these NeuCode SILAC partners is ideal for MS/MS scanning since both isotopologues are co-isolated, fragmented, and mass analyzed together. In fact, since MS/MS analysis is typically executed at low resolution (i.e., <7,500) the NeuCode SILAC MS/MS spectra are essentially identical to those of an unlabeled, non-multiplexed sample. Panel C of FIG. 10 displays the ion trap MS/MS of the isolated precursor shown in Panel B. At these low resolutions, the encoded abundance information is concealed and spectral matching is executed as if no multiplexing were being performed. It should be noted that the high resolution scan takes ~1.6 seconds to complete; however, the system performs ion trap MS/MS analyses (top 10) during that time so that very little effect on overhead is induced (16,852 vs. 18,973 MS/MS spectra acquired, NeuCode SILAC vs. traditional SILAC, respectively). The NeuCode SILAC experiment produced considerably more unique peptide spectral matches (PSMs)—2,935 vs. 2,401. This is because in traditional SILAC, each unique peptide precursor appears at two distinct m/z values—separated by 4 Da. This means that there is a tremendous amount of redundancy in peptide identifications because the most abundant peptide partners both get selected. The result is limited sampling depth. NeuCode SILAC eliminates this problem as all quantitative information is encoded within a single m/z peak for each precursor (insert of FIG. 10B) so that redundant MS/MS scans on partner peaks are not acquired.

Quantitative Accuracy and Precision of NeuCode SILAC

Figure 11:
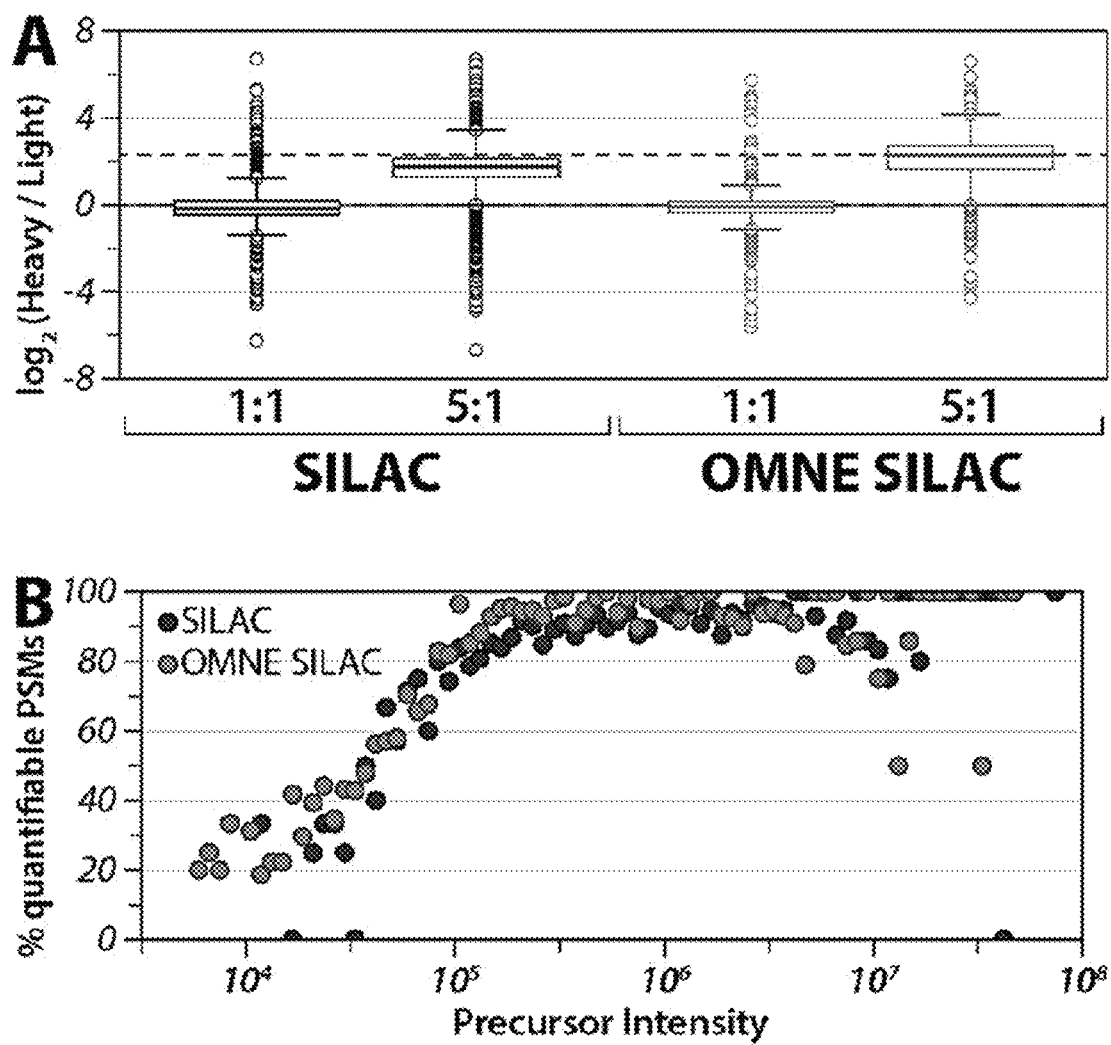
FIG. 11. NeuCode provides quantitative data that is commensurate with traditional SILAC.

Next, the quality of the quantitative data generated by NeuCode SILAC (also referred to as OMNE SILAC) was assessed as compared to traditional SILAC. FIG. 11A captures quantitative metrics for both methods: the dashed horizontal lines indicate the true ratio (grey=1:1, black=5:1) while boxplots demarcate the median (stripe), the 25th to 75th percentile (interquartile range, box), 1.5 times the interquartile range (whiskers), and outliers (open circles). From these data, it was concluded that NeuCode SILAC offers quantitative accuracy and precision that is not distinguishable from traditional SILAC. Of the 2,935 PSMs posted by NeuCode SILAC, 80% were quantifiable (2,572). For traditional SILAC 2,120 PSMs produced quantitative data 88% percent of the 2,401 total PSMs. It was wondered why NeuCode SILAC would have a reduced quantifiable rate? It should be noted that PSMs were quantified only if both partners were detected with a S/N ratio in excess of 2:1. It was surmised that since NeuCode SILAC permitted greater sampling depth and, hence, more identifications for lower S/N precursors, there was likely no fundamental difference in the frequency with which a peptide could be quantified between the two methods. To test this hypothesis, the percentage of time a PSM produced quantitative information was plotted (FIG. 11B) for both NeuCode SILAC and traditional SILAC as a function of precursor intensity. Both methods produce quantitative data less frequently (at essentially the same rate) as precursor intensity is decreased; however, NeuCode SILAC generated 1,824 PSMs having precursor intensity less than $10^{5.5}$ (arbitrary units) while traditional SILAC only detected 522 in that same range. NeuCode SILAC permits increased sampling depth compared to traditional SILAC, while maintaining highly comparable quantitative accuracy and precision.

Figures 12, 13:
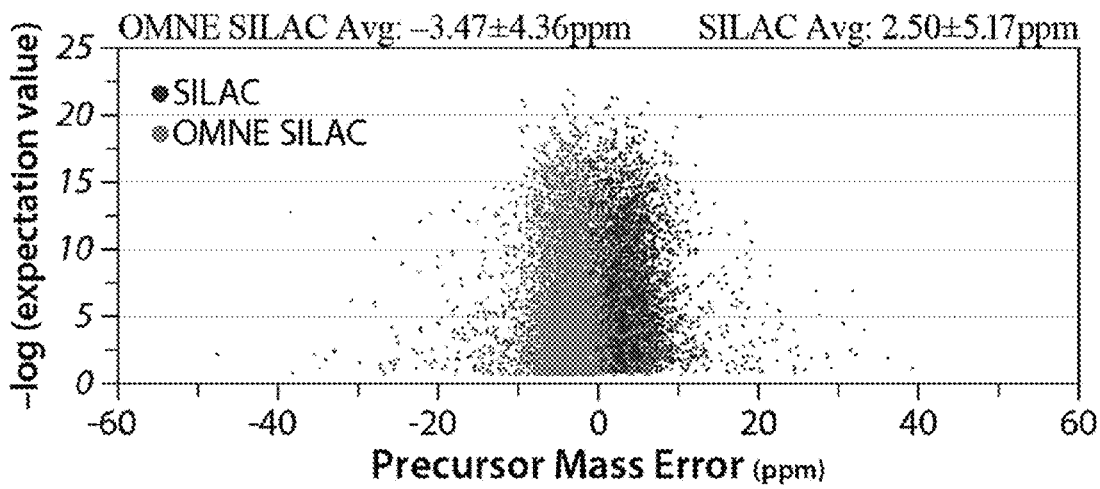
FIG. 12. A plot of the distribution of mass error (ppm) as a function of identification e-value (~significance) for both NeuCode SILAC (labeled in the figure as OMNE SILAC) and traditional SILAC for all identifications (1% FDR). NeuCode labeling does not significantly affect mass accuracy as compared to traditional SILAC.
FIG. 13. Number of neutron encoded isotopologues and their mass ranges for the six amino acids most commonly used in SILAC.

Preliminarily, all identifications from the NeuCode SILAC data were generated using the $MS^1$ scans collected under low resolution settings (30K, FIG. 10B). Since those peaks contain two unresolved versions of each peptide that differ in mass by 36 mDa, it was wondered whether any major decrease in mass accuracy would result. To test this, the distribution of mass error (ppm) was plotted as a function of identification e-value (~significance) for both NeuCode SILAC and traditional SILAC for all identifications (1% FDR, FIG. 12). A very subtle decrease in mass accuracy for NeuCode SILAC—3.5 vs. 2.5 ppm—is present with comparable precision. It was concluded that this subtle increase in mass error is not problematic as most database searching imposes precursor mass error tolerances of ±7 to ±25 ppm. It was also noted that the use of the mass values from the high resolution $MS^1$ scan, where the isotopologues are resolved, could completely eliminate this subtle error altogether.

Sample Preparation.

*Saccharomyces cerevisiae* strain BY4741 Lys1Δ was grown in defined, synthetic-complete (SC, Sunrise Science) drop out media supplemented with either light lysine (+0 Da), heavy $6^{13}C/2^{15}N$ lysine (+8.0142 Da, Cambridge Isotopes), or heavy 8D (+8.0502 Da, Cambridge Isotopes). Cells were allowed to propagate for a minimum of 10 doublings to ensure complete lysine incorporation. Upon reaching mid-log phase, the cells were harvested by centrifugation at 3,000×g for 3 minutes and washed three times with chilled $ddH_2O$. Cell pellets were re-suspended in 5 mL lysis buffer (50 mM Tris pH8, 8M urea, 75 mM sodium chloride, 100 mM sodium butyrate, 1 mM sodium orthovanadate, protease and phosphatase inhibitor tablet), and total protein was extracted by glass bead milling (Retsch). Lysate protein concentration was measured by BCA (Pierce).

Protein from lysed yeast cells was reduced by addition of 5 mM dithiothitriol and incubation for 30 minutes at ambient temperature. Free thiols were alkylated by addition of 15 mM iodoacetamide and incubated in the dark, at ambient temperature, for 30 minutes, followed by quenching with 5 mM dithiothitriol. Urea concentration was diluted to 4 M with 50 mM tris pH 8.0. Proteolytic digestion was performed by addition of LysC (Wako), 1:50 enzyme to protein ratio, and incubated at ambient temperature for 16 hours. The digest reaction was quenched by addition of TFA and desalted with a tC18 sep-pak (Waters).

SILAC known ratios were prepared by mixing "light"=+0 Da and "heavy"=+8 Da labeled peptides in the "light" to "heavy" ratios 1:1, 1:5, and 1:10 by mass. NeuCode ratios were prepared exactly the same, except light=+8.0142 Da and heavy=+8.0502 Da.

6-plex samples were prepared by labeling each NeuCode SILAC yeast peptide with three mTRAQ tags (AB SCIEX), according to the manufacturer's protocol, except that hydroxylamine was added to quench the labeling reaction after 2 hours. These peptides were mixed in the ratio 10:10:5:5:1:1 by mass.

LC-MS/MS.

For the NeuCode SILAC vs. SILAC comparison, each sample was independently loaded onto a 75 μm capillary packed with 5 μm Magic C18 (Michrome) particles in mobile phase A (0.2% formic acid in water). Peptides were gradient-eluted with mobile phase B (0.2% formic acid in acetonitrile) over 60 minutes. Eluted peptides were analyzed by an Orbitrap elite mass spectrometer (Thermo Scientific). A survey scan was performed by the Orbitrap at 30,000 resolving power to identify precursors to sample for data dependent top-10 ion trap CAD tandem mass spectrometry. NeuCode SILAC analysis had an additional quantitative 480,000 resolving power scan immediately following the survey scan. Preview mode was enabled, and precursors with unknown charge, or charge=+1, were excluded from MS2 sampling. MS1 and MS2 target ion accumulation values were set to $1\times10^6$ and $4\times10^4$, respectively. Dynamic exclusion was set to 30 seconds for −0.55 m/z and +2.55 m/z of selected precursors. MS1 6-plex samples were analyzed as above except for the following changes. Samples were eluted over a 90 minute gradient. Tandem mass spectrometry was performed by HCD fragmentation in the HCD cell followed by detection in the orbitrap with 15,000 resolving power. Finally, MS2 target ion accumulation values were set to $5\times10^4$.

Data Analysis.

MS raw files were converted to searchable text files and searched against a target-decoy database (*Saccharomyces* Genome Database (yeast), www.yeastgenome.org; UniProt (mouse), www.uniprot.org) using the Open Source Mass Spectrometry Search Algorithm (OMSSA). For all samples, methionine oxidation and cysteine carbamidomethylation were searched as a variable and fixed modification, respectively. SILAC samples were searched independently with an unmodified lysine and +8.014199 fixed modification, and later combined during false discovery rate filtering. NeuCode SILAC samples were searched with a single fixed modification representing the average mass shift from the $6^{13}C/2^{15}N$ and 8$^2$H isotopologues (+8.0322). Precursor mass tolerance was defined as 100 ppm and fragment ion mass tolerance was set to 0.5 Da. This relatively wide precursor mass tolerance was used to account for the mass difference observed between isotopologues. Search results were filtered to 1% FDR based on E-values. 6-plex samples were searched as above except for the following changes. The light (l), medium (m), and heavy (h) versions of mTRAQ were independently searched. The peptide N-terminal fixed modifications: +140.0953 (l), +144.1024 (m), or +148.104 (h); lysine fixed modifications: +148.1275 (l), +152.1346 (m), or +156.1362 (h); tyrosine variable modifications: +140.0953, +144.1024, or +148.104. Fragment ion mass tolerance was reduced to 0.1 Da. The three independent searches were combined during FDR filtering. Peptides were grouped into proteins and filtered to 1% FDR according to rules previously described.

Quantitation.

Following database searching, the FDR-filtered list of peptide-spectrum matches was first utilized to calculate the systematic precursor mass error associated with the data set. After adjusting "light" and "heavy" precursor masses for this error, an algorithm inspected every high-resolution MS1 scan within 30 seconds of all PSMs identifying a unique peptide sequence. In each MS1 scan "light" and "heavy" peaks were isolated for the first four isotopes of the isotopic cluster. If at least two peaks, with greater than S/N of 3, are found within the specified tolerance (±5 ppm for NeuCode; ±10 ppm for SILAC), a SILAC pair is created. Any peaks below the noise level simply contribute a noise-based intensity to the appropriate missing "light" or "heavy" channel. Peaks exhibiting possible peak coalescence, as determined by de-normalizing intensity by injection time, are excluded from quantitation. The intensities for "light" and "heavy" channels are summed across their elution profiles. To eliminate the noise-capped peaks on the fringes of a peptide's elution profile compressing the quantitative ratio towards 1:1, peaks with intensities below ½e the maximum intensity were discarded. Peptides were required to have a minimum of 3 ratio-providing pairs (i.e., quantified across at least 3 MS1 scans) to be eligible for quantification. Protein quantification was accomplished by averaging the ratios of all corresponding peptides. The resulting protein ratios were normalized to a median fold-change around 0 to account for unequal mixing. This algorithm was utilized to quantify both traditional and NeuCode SILAC data sets.

Example 2

Neutron-Encoded Signatures for Multiplexed Protein Quantification

Applying a neutron-encoded tagging system to protein quantification involves exploiting the subtle mass differences that are induced by the varying energies of neutron binding in C, N, O, S, Cl, Br, Si and H atoms. For example, a difference in mass of 6 mDa can be induced by swapping a $^{14}$N for a $^{15}$N atom while concomitantly switching a $^{13}$C with a $^{12}$C atom in the analyte molecule. Doing this process in various combinations, within the context of an analyte molecule, generates dozens of chemically identical isotopologues that when analyzed under normal MS analysis conditions (mass resolution <30,000) are indistinguishable—i.e., produce one m/z peak. Analysis with high resolving power (>100,000 resolution), however, reveals distinct m/z peaks whose abundances can be extracted and used to determine analyte quantity across the sundry conditions. This technology will permit very high levels of multiplexing (such as 45-plex systems, ultraplexing) while avoiding the pitfalls of both SILAC and isobaric tagging. Applications of such a tagging system include analysis of the skeletal muscle mitochondrial proteome (1098 proteins), which is of outstanding importance to human health. For example, the tagging system of the present invention can be used to precisely monitor the alterations of mitochondrial protein and phosphoproteins levels in response to cellular iron deprivation, the top worldwide nutritional disorder.

Neutron-Encoded Amino Acids for Multiplexed SILAC

Neutron-encoded isotopic versions of Lysine and Arginine permit up to 11-plex SILAC quantification. However, these highly multiplexed SILAC reagents will offer less spectral complexity than traditional 3-plex SILAC. This is accomplished by incorporating various isotopologues of each amino acid—each differing by approximately 6 mDa—to create a set of 5-plex and a 6-plex Arg/Lys amino acids that when combined yield 11 channels for quantification. These amino acids deliver an unprecedented level of multiplexing and performance to the current gold standard protein quantification technology, SILAC.

NeuCode SILAC Performance in a Complex Biological System

Figure 29:
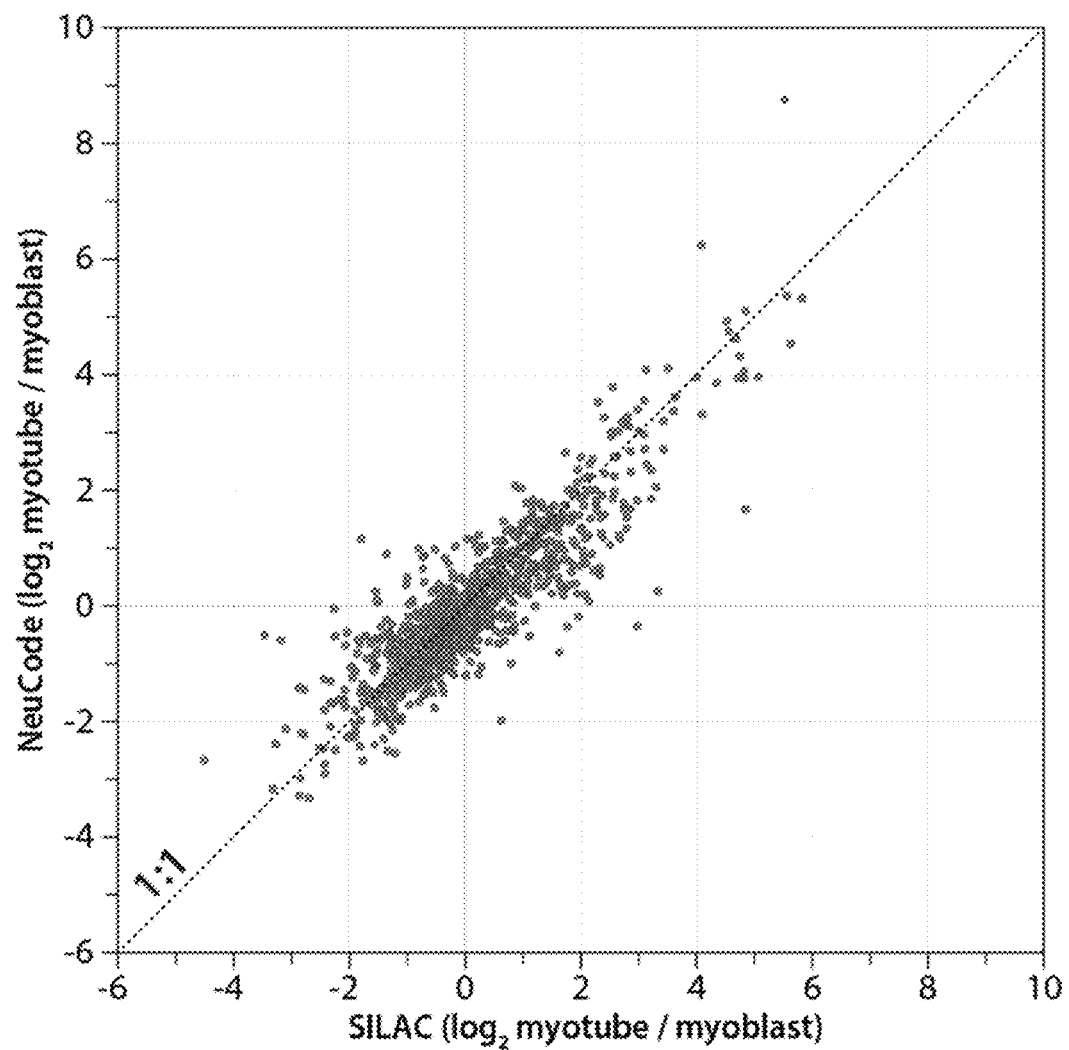
FIG. 29. Plot showing that NeuCode SILAC and SILAC demonstrate a strong correlation for quantifying protein changes during the myogenic differentiation of mouse-derived C2C12 myoblasts (m=0.82, $R^2$=0.78).
Figure 30:
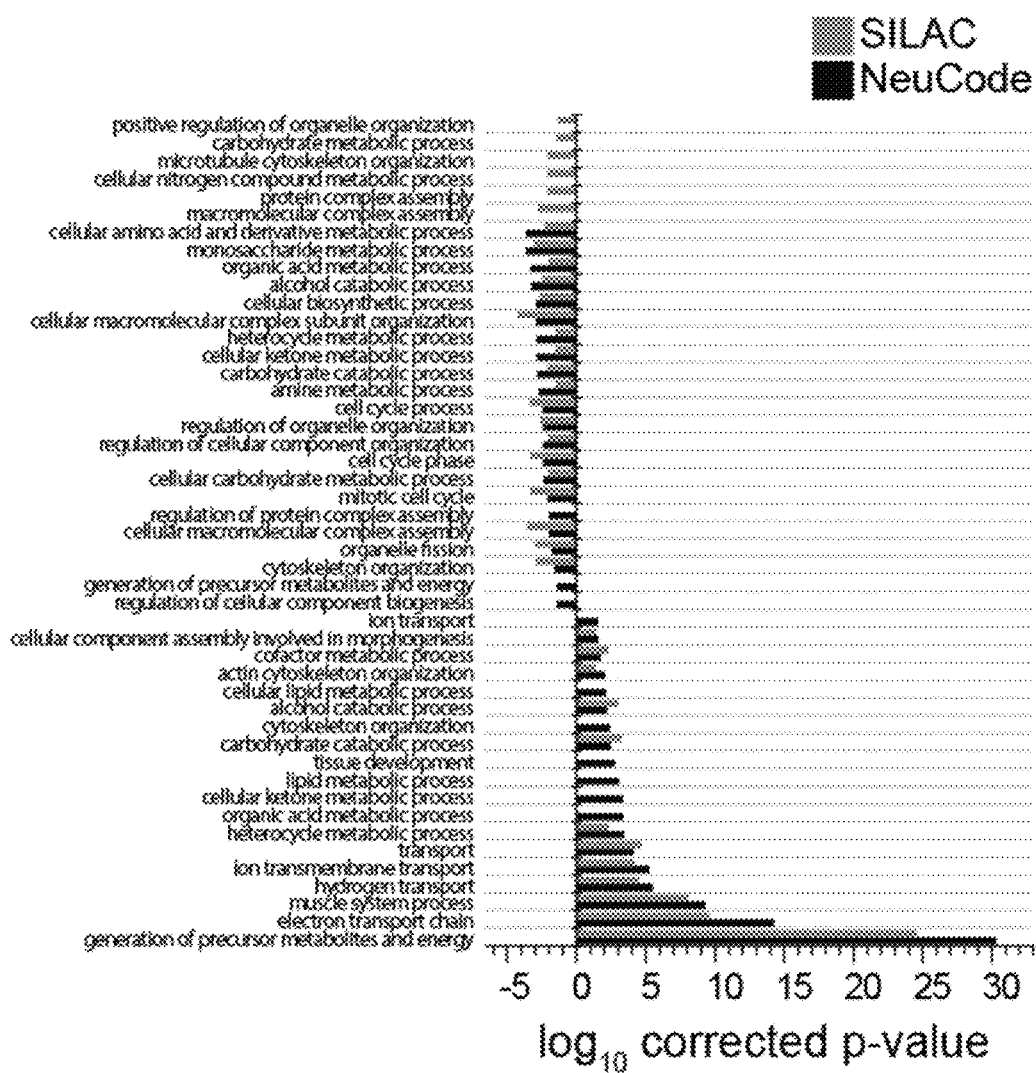
FIG. 30. Gene ontology enrichment SILAC and NeuCode. Statistically significant gene ontology bioprocess terms that are down-regulated (−) or up-regulated during differentiation from myoblast to myotube (p-value, fisher's exact test with benjamini hochberg correction).

To benchmark the performance of NeuCode against traditional SILAC in a complex biological system, NeuCode and SILAC labels were each used to quantify protein during mouse myoblasts and their myogenic differentiation to myotubes. The differentiation of mouse-derived C2C12 myoblasts is an extensively-studied model system for the development of skeletal muscle myocytes. NeuCode quantifies x % more proteins than traditional SILAC (1,458 vs. 1,031) while comparably estimating relative protein abundance (m=0.82, $R^2$=0.78; FIG. 29). Both methods measure protein changes that support the ongoing myogenic differentiation, as evidenced by the enrichment of GO terms such as electron transport chain and muscle system process (FIG. 30).

Example 3

Neutron Encoded Amino Acids

The above data demonstrates the feasibility of the NeuCode tagging strategy and doubles the plexing capacity provided by SILAC. For increased plexing, custom isotopologues of SILAC amino acids are synthesized. To determine the most expedient strategy, the mass range and number of NeuCode isotopologues for each of the six amino acids used for SILAC (Ser, Leu, Tyr, Lys, Met, and Arg) were calculated. These six amino acids alone can be manipulated to produce 3,004 isotopologues (FIG. 13)! On average, these isotopologues are spaced 1.07 mDa apart over ranges of 26-63 mDa. This means that the plexing capacity can be maximized by precisely matching isotopologue offset mass spacing to the currently achievable mass resolution. Arg offers the widest offset mass range (62.8 mDa) and, thus, the potential for the highest level of multiplexing.

Traditional SILAC experiments, however, utilize either Lys, alone, or in combination with Arg. Since custom amino acid synthesis can be costly, custom isotopologues of only Lys were initially generated. If one only uses Lys for SILAC, the best results are achieved with the protease endo LysC. This enzyme cuts peptides at Lys, ensuring every generated peptide contains a label. Endo LysC is rapidly becoming a preferred protease for proteomics and is often used in place of trypsin. LysC produces only a slightly larger peptides, on average, than trypsin (11 vs. 13 residues, yeast). Besides this, LysC is often preferred as it maintains proteolytic activity at very high amounts of denaturing agents such as urea (up to 8M).

Development of NeuCode Lysine Isotopologues

Figure 14:
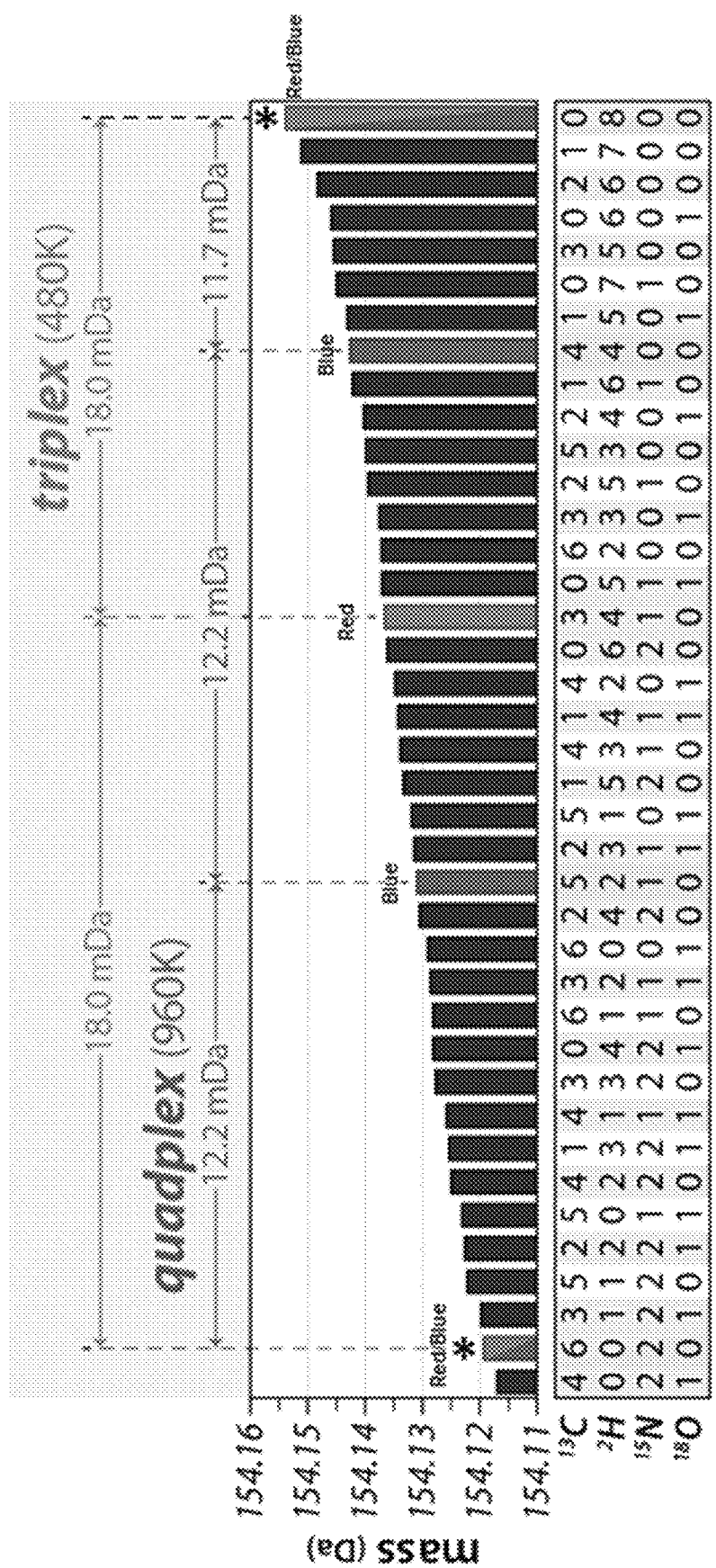
FIG. 14. Illustration of triplex and quadplex NeuCode SILAC strategy using isotopologues of +8 Da Lysine. At a resolving power of 480K, differentially NeuCode labeled peptides carrying Lysine spaced ~18 mDa apart provide a triplex quantification method (red and red/blue isotopologues). At higher resolving power (i.e., 960K), the isotopologues can be spaced closer together (~12 mDa) so that now quadplex quantification can be performed (blue and red/blue isotopologues).

FIG. 14 displays the isotope compositions and molecular weights of the 39 Lys isotopologues that are +8 Da heavier than unlabeled Lys. One can achieve an offset mass range of 38.5 mDa (adding a total of 10 Da of heavy isotopes generates the maximum offset shown in FIG. 13). Only two of the +8 isotopologues are commercially available ($^{13}C_6\,^2H_0\,^{15}N_2$ and $^{13}C_0\,^2H_8\,^{15}N_0$, red/blue striped bars in FIG. 14). These two isotopologues nearly span the entire offset mass range (36.0 mDa) and for this experiment are used as the two most extreme tags (i.e., lightest and heaviest) in either a triplex or quadplex NeuCode SILAC strategy. Synthesis of the +8 Da Lys isotopologue, $^{13}C_3\,^2H_4\,^{15}N_1$, will create a "medium" tag that is precisely 18.0 mDa from the "heavy" and "light" (red bar, FIG. 14). This spacing is compatible with 480K resolving power—the current commercial capability of the Orbitrap system and resolution used for the preliminary data shown here. It is anticipated that the wide commercial implementation of 960K resolving power on Orbitrap systems will occur in the near future. For those systems, and FT-ICR-MS systems, a quadplex NeuCode SILAC method can be implemented by synthesis of two additional +8 Lys isotopologues—$^{13}C_5\,^2H_2\,^{15}N_1$ and $^{13}C_4\,^2H_4\,^{15}N_0$. These two custom isotopologues, in combination with the commercial available "heavy" and "light"+8 Da Lys residues, are equally spaced at 12 mDa intervals (blue bars, FIG. 14). Doubling on MS resolution from 480K to 960K, and use of these custom isotopologues, will permit a quadplex NeuCode SILAC method that, when analyzed under routine conditions resolution <100K) offers the spectral complexity of an unlabeled sample.

The Route to 11-Plex NeuCode SILAC

Figure 16:
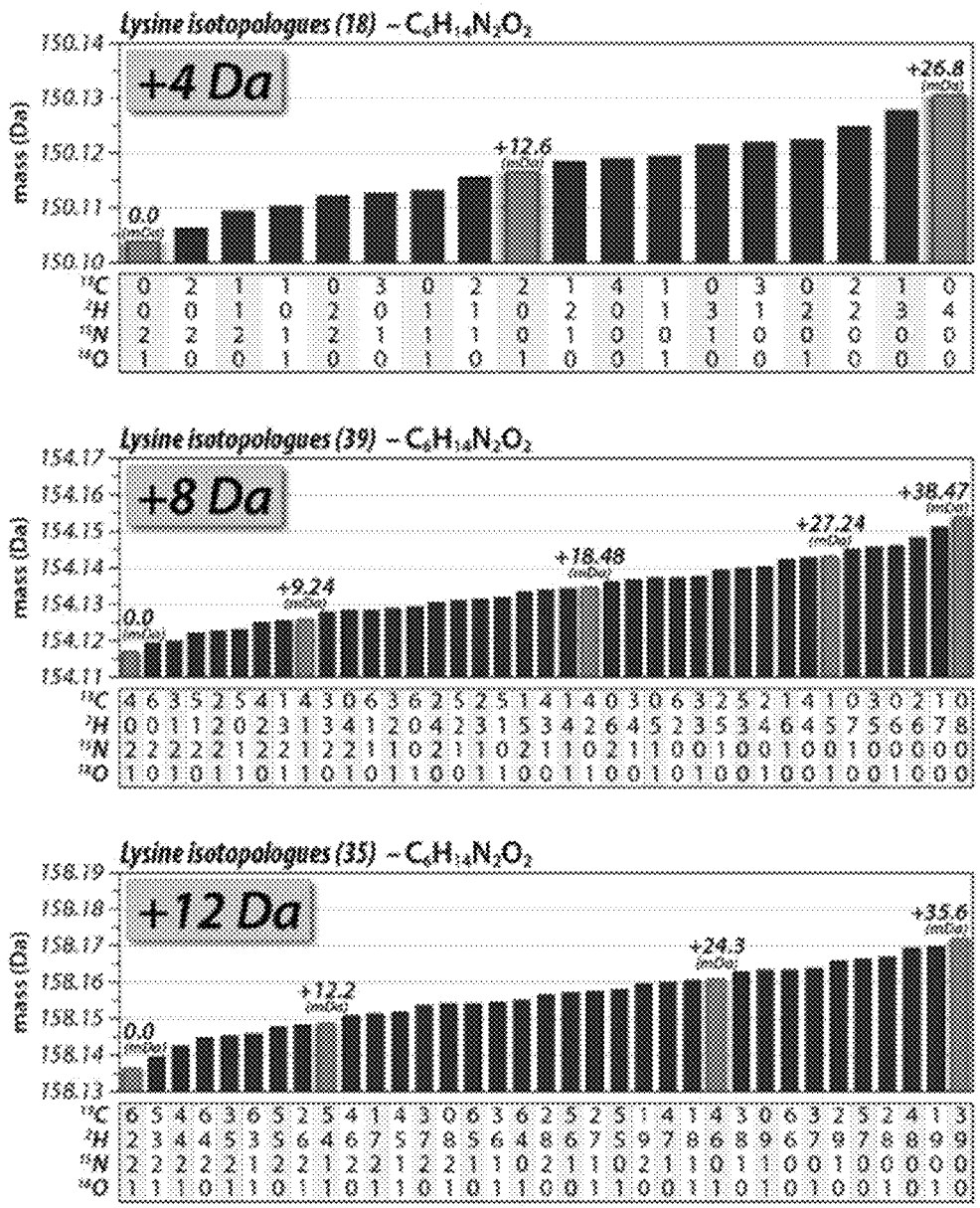
FIG. 16. A plot of the masses and isotope composition of theoretical isotopologues for the amino acid Lysine when 4, 8, or 12 extra neutrons are added using various combinations of $^{13}C$, $^2H$, $^{15}N$, $^{18}O$ atoms.

As discussed above, NeuCode SILAC reduces the spectral complexity of SILAC experiments; moreover, it greatly increases multiplexing capability (up to quadplex). It was reasoned that coupling the above NeuCode SILAC strategy with the conventional multi-Da SILAC strategy would permit even higher orders of MS1-based multiplexing. This can be accomplished this directly by generating the NeuCode isotopologues shown above with various offset masses (e.g., +4, +8, +12 Da). FIG. 15 displays the number of isotopologues available when the mass of Lys is increased by 4, 8, and 12 Da by stable heavy isotope incorporation. By dividing the mass range over which these isotopologues span with defined offset masses of 6, 12, or 18 mDa, the number of plexes each offers can be calculated (FIG. 15). By combining these three Lys groups, i.e., +4, +8, and +12 Da, either 8-plex (18 mDa spacing) or 11-plex (12 mDa spacing) NeuCode SILAC can be produced. The masses and isotope compositions of the isotopologues for the amino acid Lysine when 4, 8, or 12 extra neutrons are added using various combinations of $^{13}C$, $^2H$, $^{15}N$, $^{18}O$ atoms are shown in FIG. 16.

Figure 17:
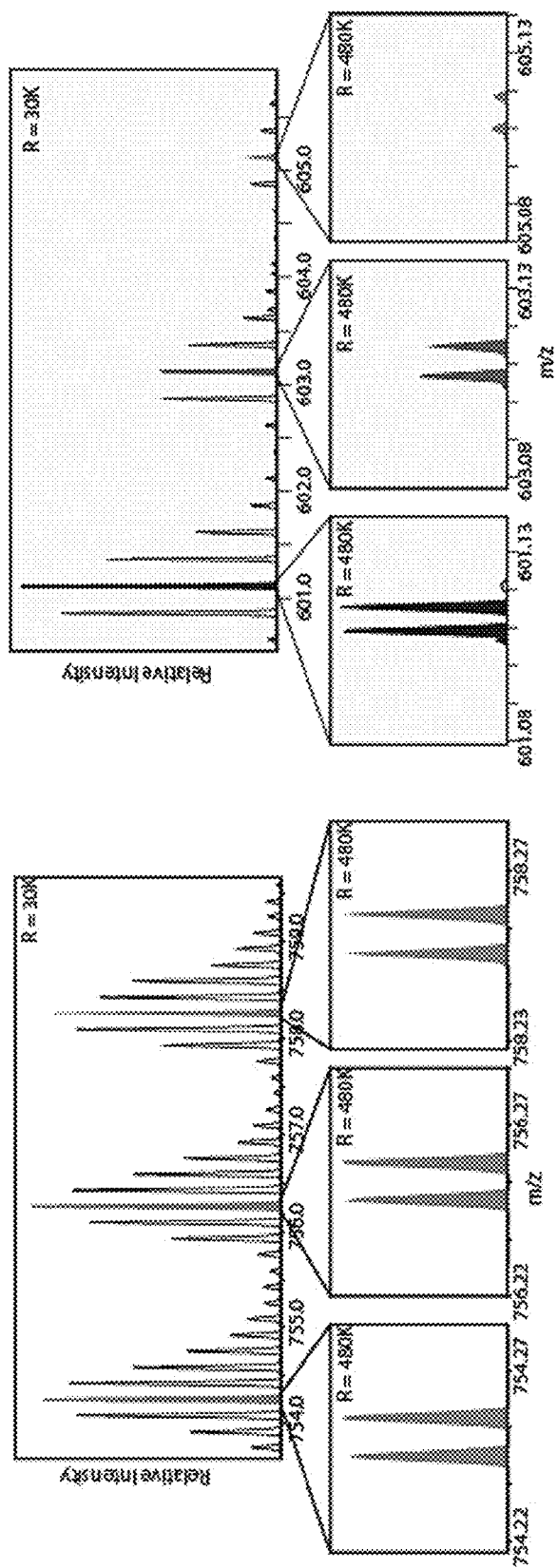
FIG. 17. Preliminary results for coupling the NeuCode SILAC strategy with the conventional multi-Da SILAC strategy to achieve very high multiplexing capacity using the duplex Lys isotopologues ($^{13}C_6/^{15}N_2$ Lys (+8.0142 Da) or $^2H_8$ (+8.0502 Da)). Once labeled, peptides containing duplex NeuCode SILAC and mTRAQ were mixed (six-plex) in a 1:1:1:1:1:1 (left) or 10:10:5:5:1:1 (right) ratios.

To transform custom quadplex Lys isotopologues into a 12-plex experiment NeuCode SILAC peptides are chemically labeled using the commercial mTRAQ tag. mTRAQ imparts a +0, +4, and +8 Da tag onto all primary amines (i.e., Lys and N-termini). In this strategy, peptides having the same sequences are distributed across 3 $MS^1$ isotopic clusters—each cluster comprises four-plex quantitative information that is only revealed upon high resolution $MS^1$ scanning. It should be noted that the mTRAQ delivers the gross mass differences that produce the three distinct isotopic clusters. This chemical labeling serves to mimic the results that would be achieved if the custom Lys isotopologues described above were available. FIG. 17 presents preliminary results using this strategy with the duplex Lys isotopologues ($^{13}C_6/^{15}N_2$Lys (+8.0142 Da) or $^2H_8$ (+8.0502 Da)). Once labeled, peptides containing duplex NeuCode SILAC and mTRAQ were mixed (six-plex) in a 1:1:1:1:1:1 (FIG. 17, left) or 10:10:5:5:1:1 (FIG. 17, right) ratio and analyzed by with the same nLC-MS/MS method described above.

Figure 8:
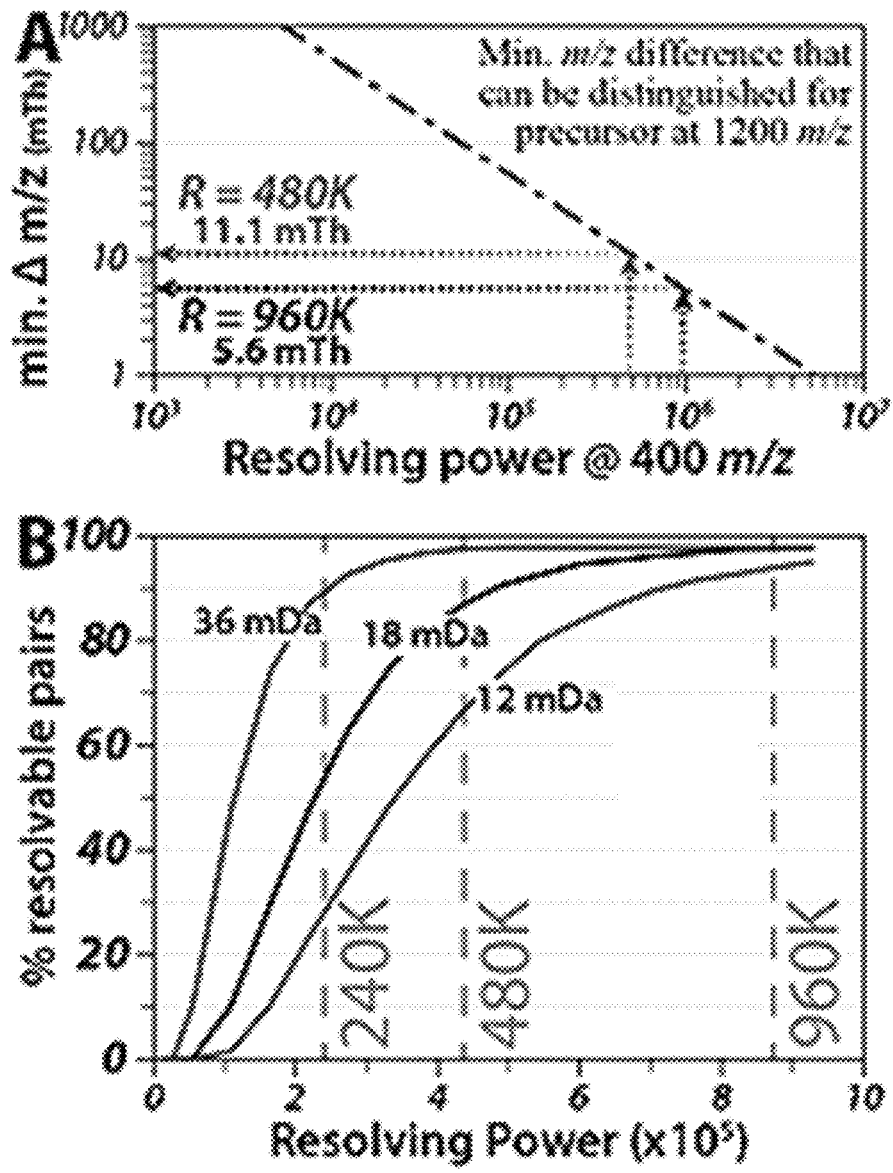
FIG. 8. Theoretical calculations depicting the minimum mass spacing that can be distinguished at R=480,000 or 960,000.

FIG. 14 presents a plot of the masses of all theoretical isotopologues of the amino acid lysine at offset masses of +4, +8, and +12 Da. Each has 18, 39, and 35 unique isotopologues spanning 26.8, 38.5, and 35.6 mDa, respectively. Current instrumentation does not have adequate resolution to distinguish each of these isotopologues, so a 92-plex SILAC capacity is not feasible with current commercial instrumentation. With current technology, however, it is possible to resolve isotopologues spaced ~10-20 mDa apart. As indicated in FIG. 8, approximately ~40% of peptides are quantifiable with 10 mDa spacing at 480K resolving power (current commercial Orbitrap maximum resolution). At 20 mDa nearly 90% are quantifiable at this resolving power. At 960K resolving power, which was recently published and under commercial development for Orbitraps, would quantify ~90% of observed peptides at 10 mDa spacing. Using ~10-12 mDa spacing, 3, 5, and 4 isotopologues were selected from the +4, +8, and +12 Da offset mass groups. When combined, these residues would offer up to 12-plex SILAC that are compatible with current FT-MS instrumentation.

Figure 18:
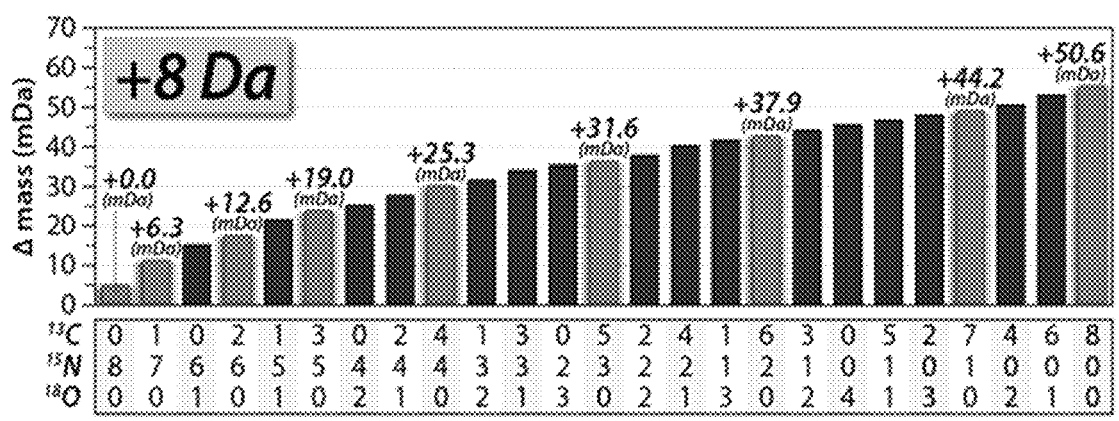
FIG. 18. Different isotopologues of a chemical tag comprising up to 8 $^{13}C$ and $^{15}N$ atoms and 4 $^{18}O$ atoms (no $^2H$ atoms).
Figure 19:
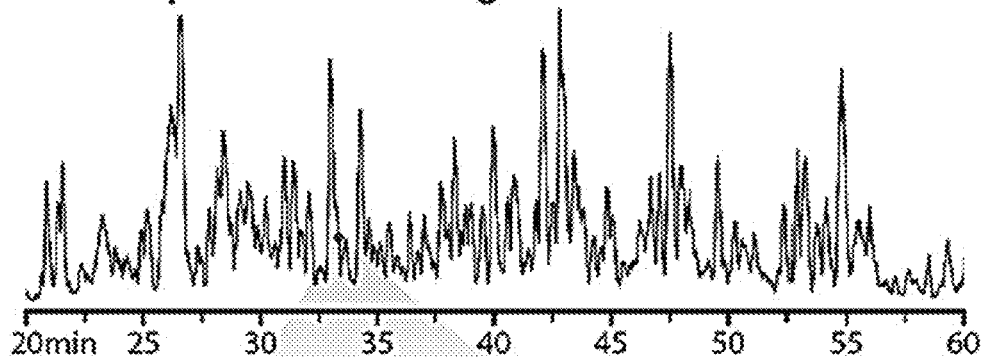
FIG. 19. Theoretical spectra achieved using the 9-plex tags described herein at 480K resolving power. Panel C displays the quantitative data and that it is only revealed upon high resolution analysis.
Figure 19:
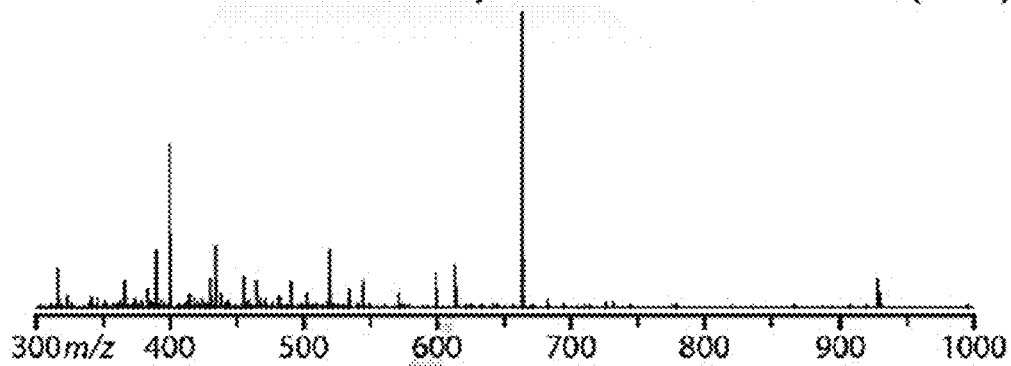
Figure 19:
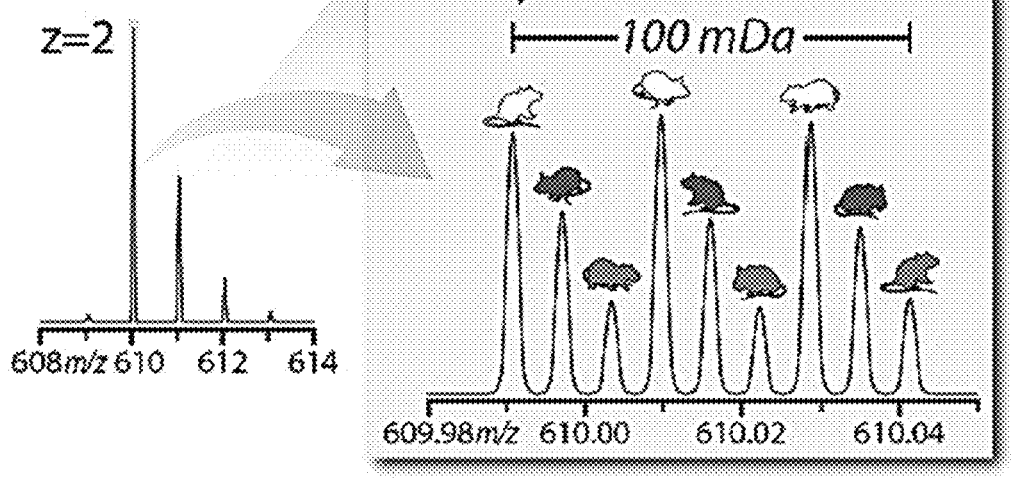

Isotopologue mass differences can be coded by use of just $^{13}C$, $^{15}N$, $^{18}O$. FIG. 18 shows different isotopologues that can be introduced into a chemical tag comprising up to 8 $^{13}C$ and $^{15}N$ atoms and up to 4 $^{18}O$ atoms (no $^2H$ atoms). The highlighted isotopologues in FIG. 18 show only the isotopologues using 0 to 8 $^{13}C$ atoms and 0 to 8 $^{15}N$ atoms (no $^{18}O$ atoms or $^2H$ atoms). In one embodiment of the present invention, synthetic tags ideally use only $^{13}C$ and $^{15}N$ as deuterium ($^2H$) can induce chromatographic peak shifts and are avoided by use of only $^{13}C$ and $^{15}N$. In this embodiment, $^{18}O$ are preferably not used because $^{18}O$ does not provide as large of a mass difference as $^{13}C$ and $^{15}N$ atoms. At 6 mDa spacing, one can produce a chemical reagent capable of offering 9-plexed quantification using just $^{13}C$ and $^{15}N$. In this way, the synthetic strategy is also streamlined as only two elements need to be varied FIG. 19 shows a theoretical simulation of what the highlighted isotopologues shown in FIG. 18 (heavy C and N atoms only) would produce if used to label a peptide (assumes two tags on the peptide). Using 480K resolution one could distinguish each of these tags and obtain 9-plex quantification data (highlighted mice).

Figure 20:
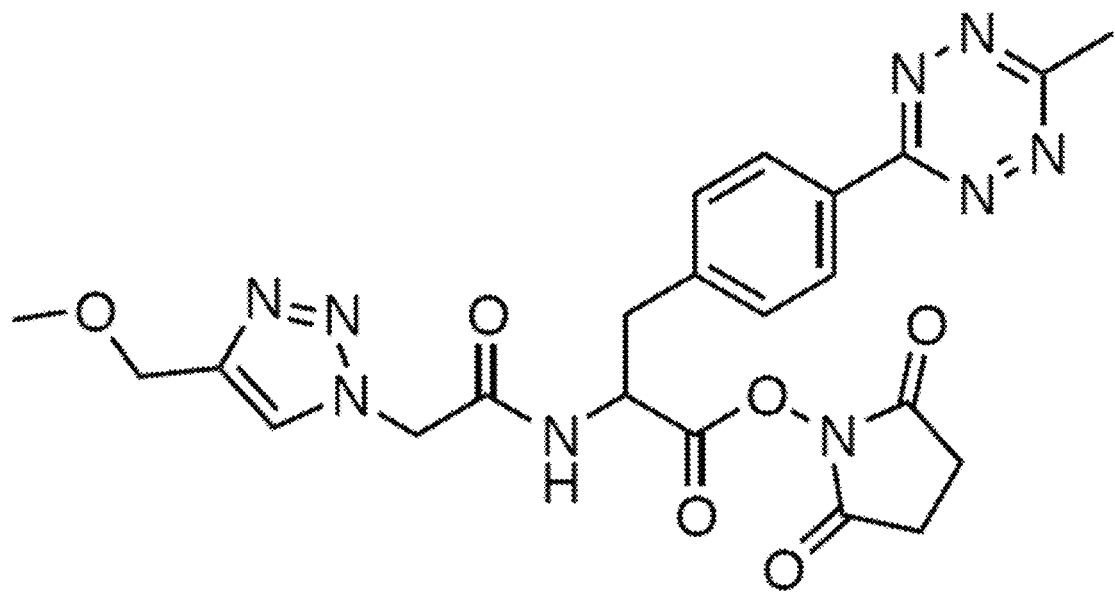
FIG. 20. A compound that could contain enough C, N and O atoms to provide the isotopologue combinations of FIG. 18.

FIG. 20 shows the structure of a possible compound that could contain enough C, N and O atoms to provide the isotopologue combinations of FIG. 18.

Figure 21:
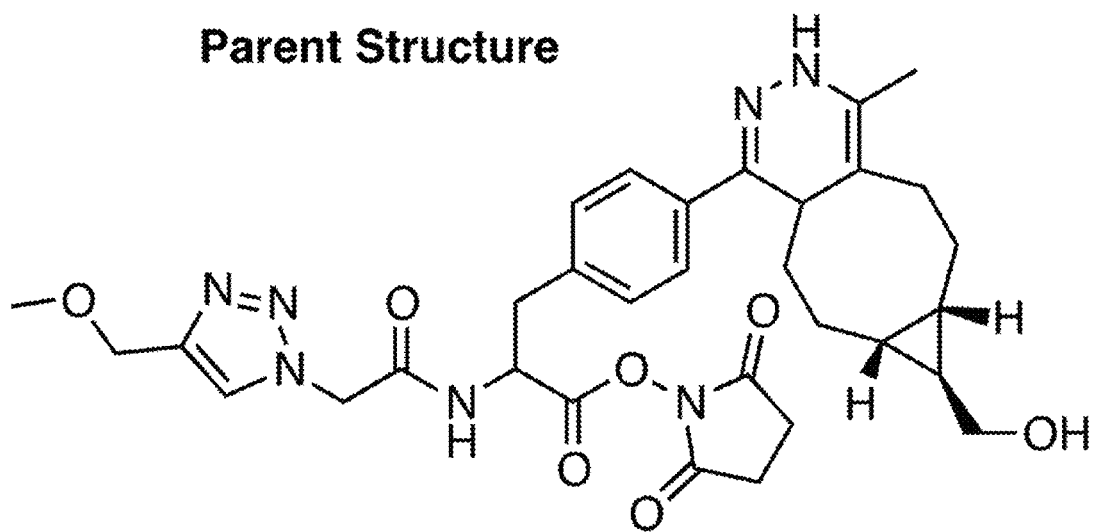
FIG. 21. Another compound that could be used as a NeuCode chemical tag.

An alternate chemical tag that similarly could be encoded to provide a wide number of isotopologues is shown in FIG. 21.

Additional Experimental Parameters

Sampling—

Development of higher order multiplexing will require increasing the number of $MS^1$ clusters of isotopologue labeled peptides. The number MS1 clusters increases the complexity of the spectra and will likely decrease duty cycle. Instrument control options for dynamic exclusion can be utilized to identify which peaks are from the same peptide species and then sample only the most abundant of these while excluding the others from $MS^2$ sampling. This will prevent sampling the same species with different forms. Analyzing truncated mass ranges to maximize identifications can also be utilized.

AGC Targets—

For each peptide precursor, the more ions analyzed during a quantitation scan, the more likely the NeuCode pairs will coalesce. This may be more of a problem for fractionated samples, where the total ion count is spread across fewer peptide precursors. Lowering the AGC target of the quantitation will decrease the likelihood of coalescence but will also result in lower signal, but also less noise. Thus, it is unlikely the signal to noise ratio, which dictates sensitivity, will change.

Fragmentation—

Current strategies employ ion trap CAD fragmentation and MS analysis, although the use of ion trap HCD and ETD are similarly possible. The duty cycle for these scan functions will be similar to CAD, but will likely give better fragmentation for the more highly charged peptide products from LysC digestion.

Resolution Testing—

Based on the above experiments, seven NeuCode SILAC pairs can be resolved with R=480K and nine can be resolved at R=960K. It is expected that greater than 80% of peptides labeled with either seven or nine NeuCode SILAC pairs, mixed in 1:1 ratios, have a complete series of resolvable pairs at FWOM.

Scan Rates—

The impact on the number of collected MS1 and MS2 spectra can be evaluated when an additional 480K or 960K resolving power quantitation scan is incorporated into the scan sequence. There is likely little impact from the additional quantitative scan because ion-trap MS2 spectra and the quantitative scan can be simultaneously collected.

Number of Peptide Identifications—

The number of peptide spectral identifications made for an NeuCode SILAC seven or eleven-plex experiment is similar to a SILAC triplex experiment. The number of identifications made will likely indirectly correlate with the number of MS1 clusters present. Thus, the experiments described above are most similar to SILAC triplex and should be compared with it as such.

Dynamic Range/Accuracy/Precision—

Mixing NeuCode SILAC pairs and SILAC pairs in 1:1, 1:2, 1:5, and 1:10 ratios demonstrate that the median values (accuracy) and standard deviation (precision) for NeuCode SILAC and SILAC are similar for each of these ratios.

Informatics Tools

Informatics tools translate the gathered spectra into highly multiplexed, $MS^1$-centric peptide quantification. This is illustrated using a duplex experiment employing two versions of lysine: "light" ($^{13}C_6^{15}N_2$, +8.0142 Da) and "heavy" ($D_8$, +8.0502 Da). First, database searching will match the low-resolution MS/MS spectra to peptides of "average" lysine composition for the given experiment (i.e., fixed modification on lysine equal to the average mass difference between all different lysine versions employed; in this case, +8.0322 Da). This list of peptide-spectrum matches will then direct an algorithm that iterates through every high-resolution MS1 scan within a certain retention time window of all PSMs identifying a unique peptide sequence. In each MS1 scan, the identification-producing peak will be isolated. Since its identity as either "light" or "heavy" remains unknown at this point, its partner peak will be searched for using the appropriate mass difference, calculated using sequence and charge state information, on both the low and high sides of the identification peak. If a peak is found whose mass falls within the tolerance (0.002 Da) and whose intensity is above the noise level for the identification peak, it is considered a partner peak and a pair is formed. If no such peak is found, a noise peak will be substituted as the partner to the identification peak to provide a pair for ratio estimation. Once pairs have been extracted from all MS1 scans within the appropriate range to assemble "light" and "heavy" profiles, these profiles will be translated so that "light" and "heavy" peak apexes align. This relocation corrects for chromatographic shifts in retention induced by certain isotopically-labeled versions of amino acids, most notably those containing deuterium, that impede accurate ratio estimation. For aligned profiles, pairs whose intensity falls below 1/e of the profile maximum will be discarded and the median ratio of the remaining pairs reported. Peptides will be required to have a minimum of 3 ratio-providing pairs to be eligible for quantification.

Example 4

Synthesis of Neutron-Encoded Chemical Reagents for Up to 45-Plex Proteomic Comparison To achieve maximum multiplexing capability (i.e., ultra-plexing) and to ensure compatibility with biological tissue and fluid analysis, a set of neutron-encoded reagents are synthesized that permit an unprecedented 45-plex analysis. These reagents employ the well-studied NHS ester reactive groups and place the tags on peptide free amines. Varying the $^{15}N$ and $^{13}C$ content of a peptide precursor affords 9 variants each spaced ~6 mDa apart. Ultra-plexing will be achieved by coupling the 9 isotopologues with +0, +4, +8, +12, and +16 Da isotopes of $^{13}C/^{18}O$—also on the tag. In this ultra-plexed mode one will observe 5 isotopic cluster peaks in the $MS^1$ spectrum. High resolution analysis will reveal 9 distinct isotopic peaks under each of these 5 clusters.

Experimental Design:

Two +8 Da heavy lysine amino acids, one with six $^{13}C$ atoms and two $^{15}N$ atoms and the other with eight $^2H$. These two isotopologues differ in mass by 36 mDa and, according to calculations, are easily distinguished at the commercially available resolution of current Orbitrap systems (480K). Two yeast cultures were grown in lysine dropout media containing either of these lysine isotopes. We then digested proteins from each culture; mixed them together and analyzed the peptides by high resolution mass spectrometry using an Orbitrap MS system.

Selection of Lysine.

Which amino acids and their various isotopologues were considered to determine the maximum number of plexing NeuCode SILAC could afford. Typical SILAC experiments utilize either Lysine, alone, or in combination with Arginine. Endo LysC is rapidly becoming a preferred protease for proteomics and is often used in place of trypsin. LysC produces only a slightly larger peptide, on average, than trypsin (11 vs. 13 residues, yeast). Besides this LysC is often preferred as it maintains proteolytic activity at very high amounts of denaturing agents such as urea (up to 8M). Because of the strong performance of LysC, isotopologues of Lys were selected for synthesis. The rationale is straightforward—LysC is often a preferred enzyme for shotgun proteomics and its use would allow isotopologues of only Lys—which simplifies the experiments. That is, the custom synthesis efforts can be focuses on only one amino acid—Lys—and still achieve excellent proteomic depth and performance by testing with the enzyme LysC, which will insure that each produced peptide contains a neutron-encoded Lys residue.

FIG. 14 presents a plot of the masses of all theoretical isotopologues of the amino acid lysine at offset masses of +4, +8, and +12 Da. Each has 18, 39, and 35 unique isotopologues spanning 26.8, 38.5, and 35.6 mDa, respectively. Current instrumentation does not have adequate resolution to distinguish each of these isotopologues, so a 92-plex SILAC capacity is not currently feasible with current commercial instrumentation. With current commercial technology, however, isotopologues spaced ~10-20 mDa apart can be resolved. FIG. 8 illustrates that ~40% of peptides are quantifiable with 10 mDa spacing at 480K resolving power (current commercial Orbitrap maximum resolution). At 20 mDa nearly 90% are quantifiable at this resolving power. 960K resolving power would quantify ~90% of observed peptides at 10 mDa spacing. Using ~10-12 mDa spacing, 3, 5, and 4 isotopologues were selected from the +4, +8, and +12 Da offset mass groups. When combined, these residues offer up to 12-plex SILAC that are compatible with current FT-MS instrumentation.

NeuCode SILAC

Neutron-encoded isotopic versions of Lysine and Arginine are generated that permit up to 11-plex SILAC quantification. These highly multi-plexed SILAC reagents, however, provide less spectral complexity than traditional 3-plex SILAC. Various isotopologues of each amino acid—each differing by 6 mDa—are incorporated to create a set of 5-plex and 6-plex Arg/Lys amino acids that when combined yield 11 channels for quantification. These amino acids deliver an increased level of multiplexing and performance compared to SILAC.

NeuCode ULTRA

To achieve maximum multiplexing capability (i.e., ultra-plexing) and to ensure compatibility with biological tissue and fluid analysis, a set of neutron-encoded reagents are synthesized that permit an unprecedented 45-plex analysis. These reagents employ the well-studied NHS ester reactive groups and place the tags on peptide free amines. Varying the $^{15}N$ and $^{13}C$ content of a peptide precursor affords 9 variants each spaced ~6 mDa apart. Ultra-plexing is achieved by coupling the 9 isotopologues with +0, +4, +8, +12, and +16 Da isotopes of $^{13}C/^{18}O$—also on the tag. In this ultra-plexed mode one will observe 5 isotopic cluster peaks in the $MS^1$ spectrum. High resolution analysis reveals 9 distinct isotopic peaks under each of these 5 clusters.

Quantitative Proteomics with Neutron Encoding—O Mass Neutron Encoded

Neutron encoding can be incorporated into 1) amino acids and 2) novel reagent tags to create a MS1-based quantification method that is superior to both conventional SILAC and isobaric tagging in many ways. Two +8 Da heavy lysine amino acids, one with six $^{13}C$'s and two $^{15}N$'s and another with eight deuteriums ($^2H$). Two yeast cultures was grown in lysine dropout media containing either of these lysine isotopes. Proteins were digested from each culture, mixed together, and analyzed by high resolution mass spectrometry using an orbitrap MS system.

The resolution required to separate peptides labeled with these lysines increases with increasing peptide mass. The achievable resolution with an Orbitrap analyzer falls off a function of the square root of the m/z value. Thus, it was not immediately obvious that current state-of-the-art MS instrument was capable of discerning the neutron-induced subtle mass differences at the high m/z values and multiple charge states of peptide precursors. It should be noted that the TMT work described above requires resolution of very small tags ~100 m/z and in only the +1 charge state. For neutron encoded mass tagging to work, this difference must be able to be resolved at much higher mass and a high charge states. With each increased charge state, the m/z spacing is reduced by a factor of two thus, requiring higher resolution to separate them.

FIG. 2 demonstrates results for a selected lysine labeled pair of peptides at varying resolution settings. It should be noted that at the typical operating resolution of the orbitrap MS system (30,000), the two NeuCode labeled peptides are indistinguishable and appear as one species. When analyzed at 240,000 resolving power, however, the pair is baseline resolved and the relative abundance of each analyte can be determined. Operation of the system at its highest resolution—480,000—produced baseline resolution of nearly every peptide species detected in the complex mixture.

SILAC Amino Acids for NeuCode

Using this approach, neutron tags can be incorporated into amino acids which are introduced into a cell culture: A similar method is done in SILAC but with isotopes that differ by 3-6 Da so that the m/z peaks are spaced out during mass analysis. There is a major limitation with the current large spacing SILAC. This limitation is that only two or three plexes can be done because the mass spectra get too complicated with all of the doublet or triplet partners. NeuCode technology allows it so that the different channels overlap at normal resolving power and so the spectral complication problem goes away.

Figure 3:
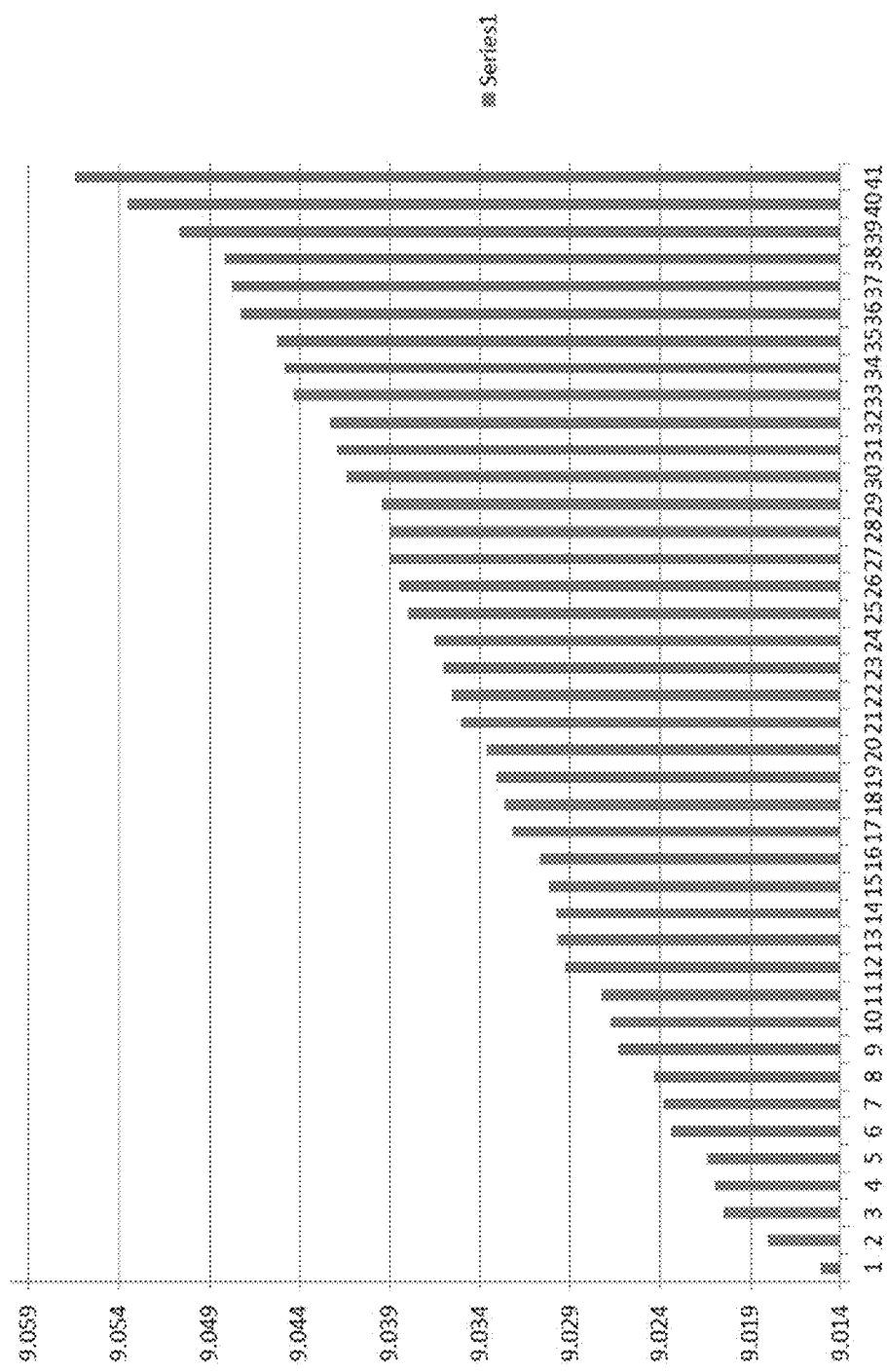
FIG. 3. A plot showing 41 different isotopologues generated by incorporating nine heavy isotopes into different positions the amino acid Lysine (selected from $^{15}N$, $^{13}C$, $^{2}H$, and $^{18}O$). The isotopologues have a mass range spanning only 41.4 mDa. The X-axis represents each isotopologue number and the y-axis is the mass difference in Da from normal Lys residues.

Nine heavy isotopes can be incorporated into different positions in the amino acid Lysine (different $^{15}N$, $^{13}C$, $^2H$, and $^{15}O$ atoms). By doing this, 41 different isotopologues are constructed that have masses spanning only 41.4 mDa. FIG. 3 is a plot showing their mass differences. The X-axis represents each isotopologue number and the y-axis is the mass difference in Da from normal Lys residues. One can select as many of these isotopologues to synthesize and incorporate into cell culture as the mass spectrometer resolving power will allow. It is envisioned that current technology will allow at least a 4-6 plex system and a doubling of resolution could then double that number. While Lys is exemplified in this experiment, one can do this for any of the amino acids.

Chemical Reagents for NeuCode

This tagging system may be used with novel tagging reagents and are not limited to SILAC related methods. This would allow for analysis of tissues and other body fluids that are not compatible with tissue culture. NHS ester technology is a widely used chemistry to link tags onto peptides for proteomic analysis including both commercial isobaric tagging methods (iTRAQ and TMT). FIGS. 20 and 21 show potential tags compatible with neutron encoding that are simple to synthesize that also uses the NHS ester linkage chemistry. Unlike isobaric tags, however, the present tagging system would not require specialized designs that incorporate reporter groups, linkers and charge sites. Instead the tags of the present invention are designed to remain bound to the peptide and to provide a quantitative measure only when examined under high resolution conditions.

Advantages of NeuCode

This method has considerable advantages over SILAC and isobaric tagging, the two most popular methods for proteome quantification today:

1. SILAC—SILAC introduces heavy amino acids, usually having a mass difference of 3 to 6 Da, into cell culture so that during analysis peptide pairs appear as doublets separated by approximately 3 to 8 Da. NeuCode can be used in amino acids for SILAC, but would (1) offer the ability for greater sampling depth compared to traditional SILAC; and (2) allow for much higher multiplexing (i.e., comparison of 4-6 samples vs. 2-3).

2. Isobaric tagging—Isobaric tagging offers multiplexing but has two significant drawbacks: (1) it suffers from interference from overlapping tagged analytes which lowers dynamic range and quantitative accuracy; and (2) it requires the collection of an MS/MS event to achieve quantification. NeuCode is an MS1 based method so interference is no longer an issue, and there no longer a need for obtaining an MS/MS scan. NeuCode, however, still has the ability to offer multiplexing just as in isobaric tagging.

Example 5

Demonstration of NeuCode with an Amino Acid Other than Lysine

Figure 22:
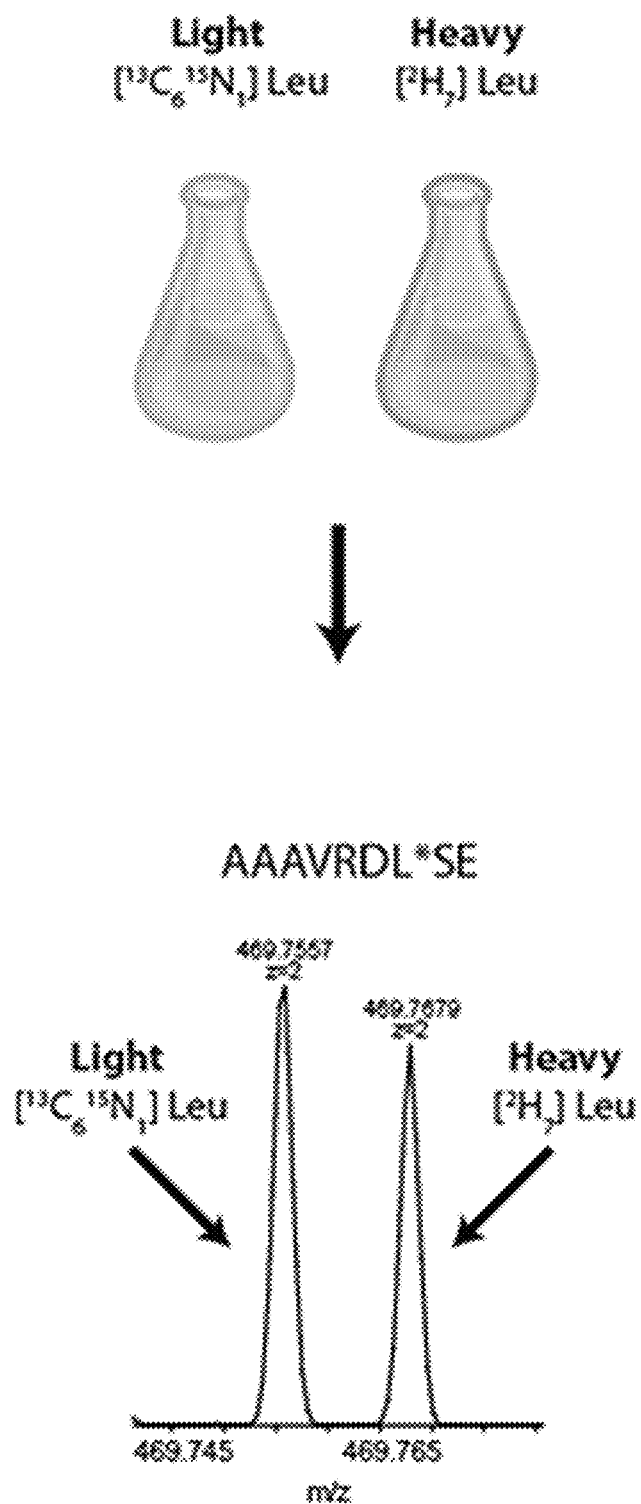
FIG. 22. Illustration of NeuCode strategy using two versions of isotopically labeled Lue which differ in mass by 27 mDa. One isotopologue has six $^{13}C$ atoms and one $^{15}N$ atom, and the second isotopologue contains seven $^2H$ atoms. Two yeast cultures were grown in leucine dropout media, each containing one of these leucine isotopologues. Proteins from each culture were digested, mixed together, and a resulting peptide (AAAVRDL*SE) analyzed by high resolution mass spectrometry using an Orbitrap MS system. Relative protein abundance measurements were made by comparing peak heights between isotopologue species.

Data has also been collected using NeuCode with the amino acid Leucine. Two versions of isotopically labeled Lue—one isotopologue having six $^{13}C$ atoms and one $^{15}N$ atom, and a second isotopologue having seven $^2H$ atoms. These differ in mass by 27 mDa. As illustrated in FIG. 22, two yeast cultures were grown in leucine dropout media each containing one of these leucine isotopologues. Proteins from each culture were digested, mixed together, and the resulting peptides analyzed by high resolution mass spectrometry using an Orbitrap MS system. The resulting peptides bearing a leucine residue were resolved at high resolution. Relative protein abundance measurements were made by comparing peak heights between isotopologue species just as with the Lys labeled examples described above.

Example 6

Chemical Reagents for NeuCode

Amine reactive isotopologue tags can be used to incorporate the NeuCode labeling strategy onto analytes other than peptides. This type of chemical approach foregoes the requirement to introduce the label during cell culture and, thus, is compatible with all sample types. For example, urea carbamylates the primary amines of peptides when exposed to heat. Peptides were carbamylated with urea isotopologues that were labeled with either $^{13}C$ or $^{15}N_2$. The primary amines of the peptide were carbamylated with either a single $^{13}C$ or $^{15}N$ for each carbamyl group added, thereby producing peptides that differ by 6.3 mDa per carbamylation site.

Figure 23:
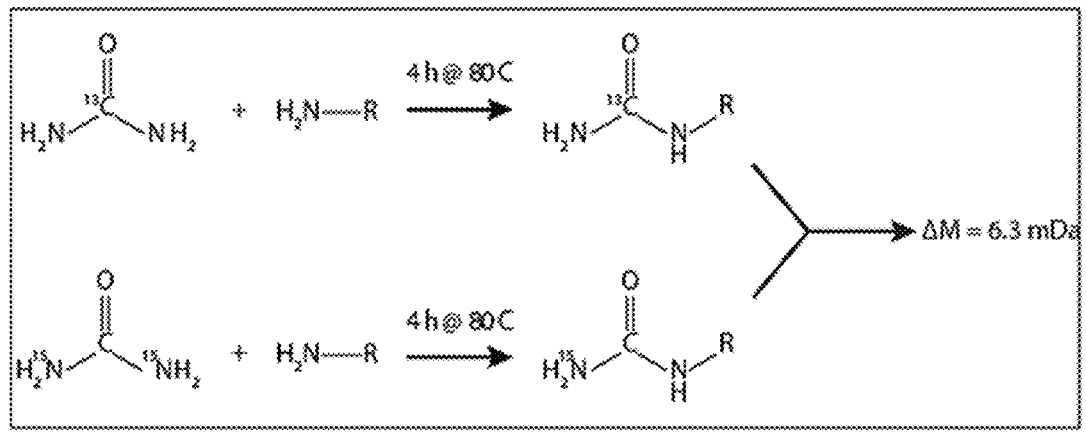
FIG. 23. Illustration of carbamylation labeling of primary amines on peptides.
Figure 23:
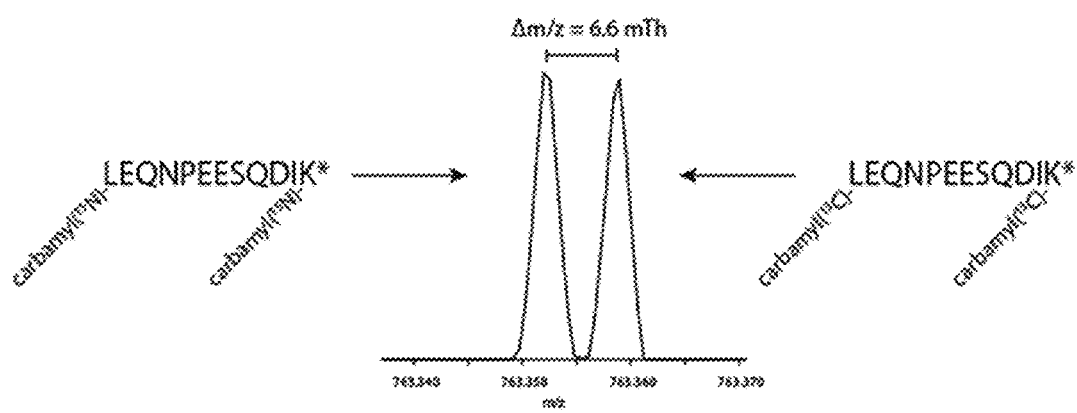

FIG. 23 shows the peptide LEQNPEESQDIK carbamylated using each of these isotopologues of urea. Both the peptide n-terminus and the primary amine on the lysine side chain were carbamylated producing peptides that are 12.6 mDa apart. These labeled peptides were resolved using 480K resolution which allows relative abundance measurements between samples labeled with these NeuCode isotopologues.

Example 7

Elements and Compositions Useful for Neutron Encoding

Not all elements are suited for neutron encoding. FIG. 24 shows a table showing common elements having stable heavy isotopes that can be incorporated into molecules. The third column provides the nominal mass of each isotope while the third column provides the exact masses. The differences between the exact mass and nominal mass arises in large part due to varying energies of neutron binding for each element. The fourth column provides the abundance ratios of the isotopes. Table 1 below presents a list of the most desirable elements for this method. The elements are grouped by the number of additional neutrons encoded when one isotope is swapped for the other, e.g., $^{12}C$ for $^{13}C$ (1 added neutron), and the mass defect that it introduces, 3.3 mDa for the latter case. Group A are desirable elements that add one neutron and a positive mass defect. Group B adds two neutrons and comes with a positive mass defect. Group C adds one neutron but introduces as negative mass defect while Group D adds two neutrons and introduces a negative mass defect. Using this grouping system, several possible neutron encoded tagging isotopologue compositions were calculated that could be embedded within a tagging system for neutron encoding. These calculations considered the use of up to 36 atoms from Group A, 8 atoms from Group B, 12 from Group C, and up to 16 atoms from Group D. All the possible combinations of these elements were examined when up to 36 additional neutrons are added, i.e., the addition of 36 neutrons by use of elements from the various groups in Table 1.

TABLE 1

List of isotope pairs that are useful for Neutron Encoding. Isotopes are arranged into one of four groups based on the number of added neutrons and whether the introduced mass defect is positive or negative.

| | Group A 1 neutron, +defect |
|---|---|
| $^{12}C/^{13}C$ | 3.3 mDa |
| $^{10}B/^{11}B$ | 3.6 mDa |
| $^{1}H/^{2}H$ | 6.3 mDa |
| | Group B 2 neutrons, +defect |
| $^{16}O/^{18}O$ | 4.2 mDa |
| | Group C 1 neutron, −defect |
| $^{14}N/^{15}N$ | −3.0 mDa |
| | Group D 2 neutrons, −defect |
| $^{28}Si/^{30}Si$ | −3.2 mDa |
| $^{32}S/^{34}S$ | −4.2 mDa |
| $^{35}Cl/^{37}Cl$ | −3.0 mDa |
| $^{79}Br/^{81}Br$ | −2.0 mDa |

The summary of these calculations are shown in Table 2, which reports the number of permutations that are possible for a tag with 1 heavy atom (1 neutron) up to 36 extra neutrons. For example, if 4 additional neutrons are included, there are 14 combinations of Group A, B, C, and D elements that sum to 4 additional neutrons. Variation of these elements among the respective groups yields numerous isotopologues that span a mass range of up to 37 mDa. Table 3 shows the various compositions that achieve the addition of 4 additional neutron using elements from the four groups and the maximum mass defect that is achieved (this is calculated using the element within each group that has the largest mass defect). Here it is seen that the isotopologue formula that achieves the larges positive mass defect draws all four neutrons from elements in Group A. The isotopologue with the largest negative mass defect draws all four neutrons from Group C. This process allows one to create isotopologues for neutron encoding with high flexibility for tag size and elemental composition while maximizing the mass range and isotopologue spacing.

TABLE 2

Summary of how many combinations of A, B, C, and D groups that can comprise isotopologues given a specified number of added neutrons (left column). As more neutrons are added more combinations are possible (central column). The column on the right presents the maximum mass range of these combinations.

| Added Neutrons | Permutations | Range (mDa) |
|---|---|---|
| 1 | 2 | 9.2 |
| 2 | 5 | 18.5 |
| 3 | 8 | 27.7 |
| 4 | 14 | 37.0 |
| 5 | 20 | 46.2 |
| 6 | 30 | 55.5 |
| 7 | 40 | 64.7 |
| 8 | 55 | 73.9 |
| 9 | 70 | 83.2 |
| 10 | 91 | 92.4 |
| 11 | 112 | 101.7 |
| 12 | 140 | 110.9 |
| 13 | 167 | 118.4 |
| 14 | 202 | 127.7 |
| 15 | 235 | 135.2 |
| 16 | 277 | 144.4 |
| 17 | 316 | 151.9 |
| 18 | 364 | 161.2 |
| 19 | 408 | 168.7 |
| 20 | 461 | 177.9 |
| 21 | 509 | 185.5 |
| 22 | 566 | 194.7 |
| 23 | 617 | 202.2 |
| 24 | 677 | 211.5 |
| 25 | 730 | 219.0 |
| 26 | 792 | 228.2 |
| 27 | 846 | 235.7 |
| 28 | 909 | 245.0 |
| 29 | 963 | 252.5 |
| 30 | 1026 | 261.7 |
| 31 | 1080 | 269.2 |
| 32 | 1143 | 278.5 |
| 33 | 1197 | 286.0 |
| 34 | 1259 | 295.2 |
| 35 | 1312 | 302.8 |
| 36 | 1372 | 312.0 |

TABLE 3

Table describing the 14 permutations of A, B, C, and D groups that are possible when 4 additional neutrons are encoded. The column on the right displays the maximum mass offset that is coded by each of these permutations. Overall a 37 mDa mass difference can be achieved.
Additional Neutrons: 4

| Comp. | Max diff. |
|---|---|
| $A_4B_0C_0D_0$ | 25.1 mDa |
| $A_2B_1C_0D_0$ | 16.8 mDa |
| $A_3B_0C_1D_0$ | 15.9 mDa |
| $A_0B_2C_0D_0$ | 8.5 mDa |
| $A_2B_0C_0D_1$ | 8.4 mDa |
| $A_1B_0C_3D_0$ | 7.6 mDa |
| $A_2B_0C_2D_0$ | 6.6 mDa |
| $A_0B_1C_0D_1$ | 0.0 mDa |
| $A_1B_0C_1D_1$ | −0.9 mDa |
| $A_0B_1C_2D_0$ | −1.7 mDa |
| $A_0B_0C_0D_2$ | −2.6 mDa |
| $A_0B_0C_0D_2$ | −8.4 mDa |
| $A_0B_0C_2D_1$ | −10.1 mDa |
| $A_0B_0C_4D_0$ | −11.9 mDa |

Example 8

Mathematical Expression of Chemical Isotopologues

Elements which are isotopically labeled with stable heavy isotopes in a compound in order to generate chemical isotopologues include, but are not limited to, C, H, N, O, S, Br, Cl and Si. Thus, in one embodiment, the different possible isotopologues for a compound is defined by the following equation:

$$^{12}C_{A-i}\,^{13}C_i\,^{1}H_{B-j}\,^{2}H_j\,^{14}N_{C-n}\,^{15}N_n\,^{16}O_{D-o}\,^{18}O_o\,^{32}S_{E-p}\,^{34}S_p\,^{79}Br_{F-i}\,^{81}Br_i\,^{35}Cl_{G-m}\,^{37}Cl_m\,^{28}Si_{H-q}\,^{30}Si_q \quad (1)$$

where:
A is the total number of carbon (C) atoms in the coded element formula;
B is the total number of hydrogen (H) atoms in the coded element formula;
C is the total number of nitrogen (N) atoms in the coded element formula;
D is the total number of oxygen (O) atoms in the coded element formula;
E is the total number of sulfur (S) atoms in the coded element formula;
F is the total number of carbon (bromine) atoms in the coded element formula;
G is the total number of chlorine (Cl) atoms in the coded element formula;
H is the total number of silicon (Si) atoms in the coded element formula; and
i, j, n, o, p, l, m, q are integers that represent the number of heavy isotopes for each respective element and are ≥0.

The number of heavy isotopes for each element will be equal to or less than the total number of atoms for that element in the coded eleme'nt formula. The number of light isotopes for each element will be the total number of atoms in the coded element formula minus the number of heavy isotopes for that element. For example, the total number of carbon atoms will be A, the total number of $^{13}C$ will be I, and the number of $^{12}C$ atoms will therefore be A-i.

The number of neutrons added by the isotopic labeling (X) is described by the following equation:

$$X = i + j + n + 2(o) + 2(p) + 2(l) + 2(m) + 2(q). \quad (2)$$

The addition of each $^{13}C$, $^{2}H$ and $^{15}N$ results in one neutron being added while the addition of each $^{18}O$, $^{34}S$, $^{81}Br$, $^{37}Cl$ and $^{30}Si$ results in two neutrons being added.

As an example, lysine has the chemical formula: $C_6H_{14}N_2O_2$. However, because some of the atoms in lysine are not compatible with neutron encoding (e.g., H atoms that are exchangeable with solvents), the coded element formula contains five fewer H atoms and one less O atom than the chemical formula. For lysine, the coded element formula: $C_6H_9N_2O_1$ provides the number of atoms that are compatible with isotopic labeling with stable heavy isotopes to form isotopologues for mass spectrometry analysis. Using the coded element formula for lysine, equation (1) is modified into the following equation:

$$^{12}C_{6-i}{}^{13}C_i{}^1H_{9-j}{}^2H_j{}^{14}N_{2-n}{}^{15}N_n{}^{16}O_{1-o}{}^{18}O_o \qquad (3)$$

where, $i \le 6$; $j \le 9$; $n \le 2$; $o \le 1$ and i, j, n, and o are 0.
Equation (2) is similarly modified for lysine to be:

$$X = i + j + n + 2(o). \qquad (4)$$

FIG. 9 illustrates all possible +2 neutron isotopologues of lysine (X=2) and equation (3) can be used to describe each of these entries. For example, the entry from the first row, "$^{13}C_0{}^2H_0{}^{15}N_2{}^{18}O_0$" incorporates only two heavy atoms, both of which are $^{15}N$. In this scenario, X=2 and n=2 so that i, j, and o=0. If we enter these numbers into equation (3) we generate the following chemical formula:

$$^{12}C_6{}^{13}C_0{}^1H_9{}^2H_0{}^{14}N_0{}^{15}N_2{}^{16}O_2{}^{18}O_0.$$

Using the code element formula for lysine and equation (1), all possible isotopologues of lysine can be determined.

Example 9

Utilization of Isotopically Labeled Amino Acids

Analytes are synthesized or reacted with isotopic tagging reagents in order to form isotopically labeled analytes. To determine the relative abundance of an analyte in a plurality of samples, a different isotopic tagging reagent is provided to the analyte in each sample, where the different isotopic tagging reagents are isotopologues.

In one embodiment, the isotopic tagging reagent is an isotopically labeled amino acid. The isotopically labeled amino acid is reacted with the analyte so that the isotopically labeled amino covalently binds to the analyte. Alternatively, when the analyte is a peptide, the peptide is synthesized so that the isotopically labeled amino acid is incorporated into the backbone of the peptide itself.

FIG. 25 provides the structures for twenty common amino acids which can be used as isotopic tagging reagents. The second column in FIG. 25 (labeled as "Composition") provides the chemical formula for each compound, and the third column provides the coded element formula. Using the coded element formula for each compound, equation (1) described above is modified to give an equation for each compound that describes all possible isotopologues for that compound.

Table 4a provides the modified equations for each amino acid describing the different possible isotopologues for each amino acid. The maximum number for each heavy isotope for each modified equation is provided in the third column. For example, lysine is provided as item 12 in Table 4a and in FIG. 25, with the modified equation for lysine presented in Table 4a being the same equation (3) presented above:

$$^{12}C_{6-i}{}^{13}C_i{}^1H_{9-j}{}^2H_j{}^{14}N_{2-n}{}^{15}N_n{}^{16}O_{1-o}{}^{18}O_o. \qquad (3)$$

The lysine isotopologues are provided to the analyte in each sample and the isotopologues are detected during mass spectrometry based on the small differences in their molecular masses. Relative quantification of the analyte in each sample is then determined by comparing the relative amounts of the detected isotopologues. If one of the samples comprises a lysine standard (i.e., a lysine isotopologue present in a known amount), then absolute quantification of the analyte in each sample is achieved.

TABLE 4a

| | Coded element Formula | Modified Equations | Range Maximums |
|---|---|---|---|
| | \multicolumn{3}{l}{For all following equations: $i \ge 0, j \ge 0, l \ge 0, m \ge 0, n \ge 0, o \ge 0, p \ge 0$, and $q \ge 0$.} | |
| 1 | H4C3NO | $^{12}C_{3-i}{}^{13}C_i{}^1H_{4-j}{}^2H_j{}^{14}N_{1-n}{}^{15}N_n{}^{16}O_{1-o}{}^{18}O_o$ | $i \le 3, j \le 4, n \le 1, o \le 1$ |
| 2 | H7C6N4O | $^{12}C_{6-i}{}^{13}C_i{}^1H_{7-j}{}^2H_j{}^{14}N_{4-n}{}^{15}N_n{}^{16}O_{1-o}{}^{18}O_o$ | $i \le 6, j \le 7, n \le 4, o \le 1$ |
| 3 | H3C4N2O2 | $^{12}C_{4-i}{}^{13}C_i{}^1H_{3-j}{}^2H_j{}^{14}N_{2-n}{}^{15}N_n{}^{16}O_{2-o}{}^{18}O_o$ | $i \le 4, j \le 3, n \le 2, o \le 2$ |
| 4 | H3C4NO2 | $^{12}C_{4-i}{}^{13}C_i{}^1H_{3-j}{}^2H_j{}^{14}N_{1-n}{}^{15}N_n{}^{16}O_{2-o}{}^{18}O_o$ | $i \le 4, j \le 3, n \le 1, o \le 2$ |
| 5 | H3C3NOS | $^{12}C_{3-i}{}^{13}C_i{}^1H_{3-j}{}^2H_j{}^{14}N_{1-n}{}^{15}N_n{}^{16}O_{1-o}{}^{18}O_o{}^{32}S_{1-p}{}^{34}S_p$ | $i \le 3, j \le 3, n \le 1, o \le 1, p \le 1$ |
| 6 | H5C5NO2 | $^{12}C_{5-i}{}^{13}C_i{}^1H_{5-j}{}^2H_j{}^{14}N_{1-n}{}^{15}N_n{}^{16}O_{2-o}{}^{18}O_o$ | $i \le 5, j \le 5, n \le 1, o \le 2$ |
| 7 | H5C5N2O2 | $^{12}C_{5-i}{}^{13}C_i{}^1H_{5-j}{}^2H_j{}^{14}N_{2-n}{}^{15}N_n{}^{16}O_{2-o}{}^{18}O_o$ | $i \le 5, j \le 5, n \le 2, o \le 2$ |
| 8 | H2C2NO | $^{12}C_{2-i}{}^{13}C_i{}^1H_{2-j}{}^2H_j{}^{14}N_{1-n}{}^{15}N_n{}^{16}O_{1-o}{}^{18}O_o$ | $i \le 2, j \le 2, n \le 1, o \le 1$ |
| 9 | H5C6N3O | $^{12}C_{6-i}{}^{13}C_i{}^1H_{5-j}{}^2H_j{}^{14}N_{3-n}{}^{15}N_n{}^{16}O_{1-o}{}^{18}O_o$ | $i \le 6, j \le 5, n \le 3, o \le 1$ |
| 10 | H10C6NO | $^{12}C_{6-i}{}^{13}C_i{}^1H_{10-j}{}^2H_j{}^{14}N_{1-n}{}^{15}N_n{}^{16}O_{1-o}{}^{18}O_o$ | $i \le 6, j \le 10, n \le 1, o \le 1$ |
| 11 | H10C6NO | $^{12}C_{6-i}{}^{13}C_i{}^1H_{10-j}{}^2H_j{}^{14}N_{1-n}{}^{15}N_n{}^{16}O_{1-o}{}^{18}O_o$ | $i \le 6, j \le 10, n \le 1, o \le 1$ |
| 12 | H9C6N2O | $^{12}C_{6-i}{}^{13}C_i{}^1H_{9-j}{}^2H_j{}^{14}N_{2-n}{}^{15}N_n{}^{16}O_{1-o}{}^{18}O_o$ | $i \le 6, j \le 9, n \le 2, o \le 1$ |
| 13 | H8C5NOS | $^{12}C_{5-i}{}^{13}C_i{}^1H_{8-j}{}^2H_j{}^{14}N_{1-n}{}^{15}N_n{}^{16}O_{1-o}{}^{18}O_o{}^{32}S_{1-p}{}^{34}S_p$ | $i \le 5, j \le 8, n \le 1, o \le 1, p \le 1$ |
| 14 | H8C9NO | $^{12}C_{9-i}{}^{13}C_i{}^1H_{8-j}{}^2H_j{}^{14}N_{1-n}{}^{15}N_n{}^{16}O_{1-o}{}^{18}O_o$ | $i \le 9, j \le 8, n \le 1, o \le 1$ |
| 15 | H7C5NO | $^{12}C_{5-i}{}^{13}C_i{}^1H_{7-j}{}^2H_j{}^{14}N_{1-n}{}^{15}N_n{}^{16}O_{1-o}{}^{18}O_o$ | $i \le 5, j \le 7, n \le 1, o \le 1$ |
| 16 | H3C3NO | $^{12}C_{3-i}{}^{13}C_i{}^1H_{3-j}{}^2H_j{}^{14}N_{1-n}{}^{15}N_n{}^{16}O_{1-o}{}^{18}O_o$ | $i \le 3, j \le 3, n \le 1, o \le 1$ |
| 17 | H5C4NO | $^{12}C_{4-i}{}^{13}C_i{}^1H_{5-j}{}^2H_j{}^{14}N_{1-n}{}^{15}N_n{}^{16}O_{1-o}{}^{18}O_o$ | $i \le 4, j \le 5, n \le 1, o \le 1$ |
| 18 | H8C11N2O | $^{12}C_{11-i}{}^{13}C_i{}^1H_{8-j}{}^2H_j{}^{14}N_{2-n}{}^{15}N_n{}^{16}O_{1-o}{}^{18}O_o$ | $i \le 11, j \le 8, n \le 2, o \le 1$ |
| 19 | H7C9NO | $^{12}C_{9-i}{}^{13}C_i{}^1H_{7-j}{}^2H_j{}^{14}N_{1-n}{}^{15}N_n{}^{16}O_{1-o}{}^{18}O_o$ | $i \le 9, j \le 7, n \le 1, o \le 1$ |
| 20 | H8C5NO | $^{12}C_{5-i}{}^{13}C_i{}^1H_{8-j}{}^2H_j{}^{14}N_{1-n}{}^{15}N_n{}^{16}O_{1-o}{}^{18}O_o$ | $i \le 5, j \le 8, n \le 1, o \le 1$ |

Table 4b provided as an appendix is a part of the specification provided herein that is also hereby incorporated by reference. Table 4b provides possible coded element combinations that result in isotopologues of twenty amino acids that are useful in embodiments of the invention.

Example 10

Utilization of Isotopic Peptide Labels

In other embodiments, the isotopic tagging reagent is a compound other than an amino acid. The isotopic tagging reagent is any compound able to covalently bind to the analyte or that is able to be incorporated into the analyte during synthesis of the analyte, particularly when the analyte is a peptide.

Figure 26:
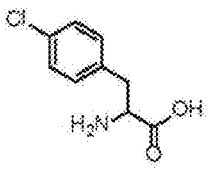
FIG. 26. Structures, chemical formulas, and coded element formulas for peptide labels which can be used as isotopic tagging reagents which are reacted with a peptide, or attached to the peptide during synthesis of the peptide.
Figure 26:
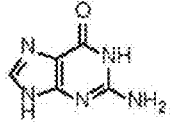
Figure 26:
Figure 26:
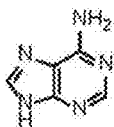
Figure 26:
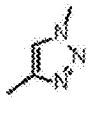
Figure 26:
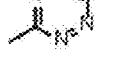
Figure 26:
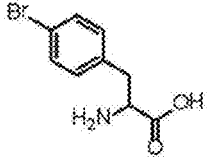
Figure 26:
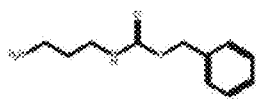
Figure 26:
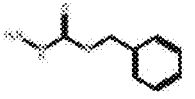
Figure 26:
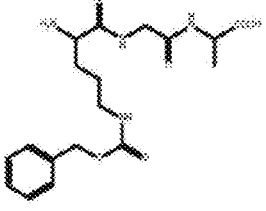
Figure 26:
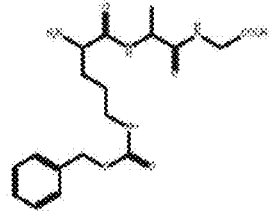

FIG. 26 provides the structures for twenty-eight peptide labels that can be isotopically labeled and reacted with a peptide, or attached to the peptide during synthesis of the peptide. The second column in FIG. 26 provides the chemical formula for each compound, and the third column provides the coded element formula. Using the coded element formula for each compound, equation (1) can be modified to give an equation for each compound that describes all possible isotopologues for that compound.

Figure 27:
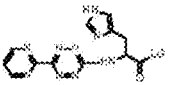
FIG. 27. Structures, chemical formulas, and coded element formulas for additional peptide labels which can be used as isotopic tagging reagents.
Figure 27:
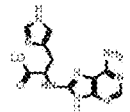
Figure 27:
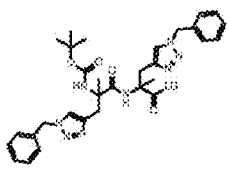
Figure 27:
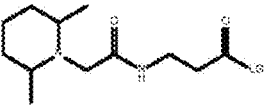
Figure 27:
Figure 27:
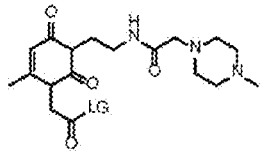

FIG. 27 provides the structures for thirteen additional peptide labels that can be isotopically labeled and reacted with a peptide. Each of these peptide labels contain a leaving group (designated as "LG" in the structure) which leaves the peptide label when the peptide label is reacted with the peptide analyte. Accordingly, the leaving group is not part of the isotopically labeled peptide. The leaving group is any functional group that allows the peptide label to react with a functional group of a peptide, such as an amine reactive group or carboxyl reactive group. The second column in FIG. 27 provides the chemical formula for each compound (not including any leaving groups (LG)), and the third column provides the coded element formula. Using the coded element formula for each compound, equation (1) described above can be modified to give an equation for each compound that describes all possible isotopologues for that compound. The numbering of the compounds in FIG. 27 begins with number 29 in order to continue where the numbering of FIG. 26 ended.

Table 5 provides the modified equations for the peptide labels of FIGS. 26 and 27, where the modified equations describe the different possible isotopologues for each peptide label. The maximum number for each heavy isotope for each modified equation is provided in the third column. For example, compound 1 of FIG. 26 is provided as item 1 in Table 5, with the modified equation for this compound being:

$$^{12}C_{9-i}{}^{13}C_i{}^1H_{7-j}{}^2H_j{}^{35}Cl_{1-m}{}^{37}Cl_m{}^{14}N_{1-n}{}^{15}N_n{}^{16}O_{1-o}{}^{18}O_o. \quad (4)$$

Similarly, compound 29 of FIG. 27 is provided as item 29 in Table 5 having a modified equation of:

$$^{12}C_{14-i}{}^{13}C_i{}^1H_{12-j}{}^2H_j{}^{14}N_{8-n}{}^{15}N_n{}^{16}O_{1-o}{}^{18}O_o. \quad (5)$$

The possible isotopologues of these compounds fall within their respective given modified equations.

The isotopologues for a particular protein label are provided to the analyte in each sample and the isotopologues are detected during mass spectrometry based on the small differences in their molecular masses. Relative quantification of the analyte in each sample is then determined by comparing the relative amounts of the detected isotopologues. Absolute quantification is by incorporating a standard (i.e., a specific isotopologue present in a known amount) in one of the samples.

TABLE 5

For all following equations: $i \geq 0, j \geq 0, l \geq 0, m \geq 0, n \geq 0, o \geq 0, p \geq 0$, and $q \geq 0$.

| | Coded element Formula | Modified Equations | Range Maximums |
|---|---|---|---|
| 1 | H7C9NOCl | $^{12}C_{9-i}{}^{13}C_i{}^1H_{7-j}{}^2H_j{}^{35}Cl_{1-m}{}^{37}Cl_m{}^{14}N_{1-n}{}^{15}N_n{}^{16}O_{1-o}{}^{18}O_o$ | $i \leq 9, j \leq 7, m \leq 1, n \leq 1, o \leq 1$ |
| 2 | HC5N5O | $^{12}C_{5-i}{}^{13}C_i{}^1H_{1-j}{}^2H_j{}^{14}N_{5-n}{}^{15}N_n{}^{16}O_{1-o}{}^{18}O_o$ | $i \leq 5, j \leq 1, n \leq 5, o \leq 1$ |
| 3 | H6C5N2 | $^{12}C_{5-i}{}^{13}C_i{}^1H_{6-j}{}^2H_j{}^{14}N_{2-n}{}^{15}N_n$ | $i \leq 5, j \leq 6, n \leq 2$ |
| 4 | H2C3N5 | $^{12}C_{3-i}{}^{13}C_i{}^1H_{2-j}{}^2H_j{}^{14}N_{5-n}{}^{15}N_n$ | $i \leq 3, j \leq 2, n \leq 5$ |
| 5 | H7C4N3 | $^{12}C_{4-i}{}^{13}C_i{}^1H_{7-j}{}^2H_j{}^{14}N_{3-n}{}^{15}N_n$ | $i \leq 4, j \leq 7, n \leq 3$ |
| 6 | H6C4N4 | $^{12}C_{4-i}{}^{13}C_i{}^1H_{6-j}{}^2H_j{}^{14}N_{4-n}{}^{15}N_n$ | $i \leq 4, j \leq 6, n \leq 4$ |
| 7 | H7C9NOBr | $^{12}C_{9-i}{}^{13}C_i{}^1H_{7-j}{}^2H_j{}^{79}Br_{1-l}{}^{81}Br_l{}^{14}N_{1-n}{}^{15}N_n{}^{16}O_{1-o}{}^{18}O_o$ | $i \leq 9, j \leq 7, l \leq 1, n \leq 1, o \leq 1$ |
| 8 | H2C4N3O | $^{12}C_{4-i}{}^{13}C_i{}^1H_{2-j}{}^2H_j{}^{14}N_{3-n}{}^{15}N_n{}^{16}O_{1-o}{}^{18}O_o$ | $i \leq 4, j \leq 2, n \leq 3, o \leq 1$ |
| 9 | H2C4N2O2 | $^{12}C_{4-i}{}^{13}C_i{}^1H_{2-j}{}^2H_j{}^{14}N_{2-n}{}^{15}N_n{}^{16}O_{2-o}{}^{18}O_o$ | $i \leq 4, j \leq 2, n \leq 2, o \leq 2$ |
| 10 | H4C5N2O2 | $^{12}C_{5-i}{}^{13}C_i{}^1H_{4-j}{}^2H_j{}^{14}N_{2-n}{}^{15}N_n{}^{16}O_{2-o}{}^{18}O_o$ | $i \leq 5, j \leq 4, n \leq 2, o \leq 2$ |
| 11 | H14C14N3O4 | $^{12}C_{14-i}{}^{13}C_i{}^1H_{14-j}{}^2H_j{}^{14}N_{3-n}{}^{15}N_n{}^{16}O_{4-o}{}^{18}O_o$ | $i \leq 14, j \leq 14, n \leq 3, o \leq 4$ |
| 12 | H11C9NO | $^{12}C_{9-i}{}^{13}C_i{}^1H_{11-j}{}^2H_j{}^{14}N_{1-n}{}^{15}N_n{}^{16}O_{1-o}{}^{18}O_o$ | $i \leq 9, j \leq 11, n \leq 1, o \leq 1$ |
| 13 | H10C10NO2 | $^{12}C_{10-i}{}^{13}C_i{}^1H_{10-j}{}^2H_j{}^{14}N_{1-n}{}^{15}N_n{}^{16}O_{2-o}{}^{18}O_o$ | $i \leq 10, j \leq 10, n \leq 1, o \leq 2$ |
| 14 | H9C10N3O3 | $^{12}C_{10-i}{}^{13}C_i{}^1H_{9-j}{}^2H_j{}^{14}N_{3-n}{}^{15}N_n{}^{16}O_{3-o}{}^{18}O_o$ | $i \leq 10, j \leq 9, n \leq 3, o \leq 3$ |
| 15 | H7C7NO | $^{12}C_{7-i}{}^{13}C_i{}^1H_{7-j}{}^2H_j{}^{14}N_{1-n}{}^{15}N_n{}^{16}O_{1-o}{}^{18}O_o$ | $i \leq 7, j \leq 7, n \leq 1, o \leq 1$ |
| 16 | H12C11NOS | $^{12}C_{11-i}{}^{13}C_i{}^1H_{12-j}{}^2H_j{}^{14}N_{1-n}{}^{15}N_n{}^{16}O_{1-o}{}^{18}O_o{}^{32}S_{1-p}{}^{34}S_p$ | $i \leq 11, j \leq 12, n \leq 1, o \leq 1, p \leq 1$ |
| 17 | H17C12NO | $^{12}C_{12-i}{}^{13}C_i{}^1H_{17-j}{}^2H_j{}^{14}N_{1-n}{}^{15}N_n{}^{16}O_{1-o}{}^{18}O_o$ | $i \leq 12, j \leq 17, n \leq 1, o \leq 1$ |
| 18 | H9C9N2O | $^{12}C_{9-i}{}^{13}C_i{}^1H_{9-j}{}^2H_j{}^{14}N_{2-n}{}^{15}N_n{}^{16}O_{1-o}{}^{18}O_o$ | $i \leq 9, j \leq 9, n \leq 2, o \leq 1$ |
| 19 | H14C14N3O4 | $^{12}C_{14-i}{}^{13}C_i{}^1H_{14-j}{}^2H_j{}^{14}N_{3-n}{}^{15}N_n{}^{16}O_{4-o}{}^{18}O_o$ | $i \leq 14, j \leq 14, n \leq 3, o \leq 4$ |
| 20 | H14C14N3O4 | $^{12}C_{14-i}{}^{13}C_i{}^1H_{14-j}{}^2H_j{}^{14}N_{3-n}{}^{15}N_n{}^{16}O_{4-o}{}^{18}O_o$ | $i \leq 14, j \leq 14, n \leq 3, o \leq 4$ |
| 21 | H13C12N2O3 | $^{12}C_{12-i}{}^{13}C_i{}^1H_{13-j}{}^2H_j{}^{14}N_{2-n}{}^{15}N_n{}^{16}O_{3-o}{}^{18}O_o$ | $i \leq 12, j \leq 13, n \leq 2, o \leq 3$ |
| 22 | H23C16N2O4 | $^{12}C_{16-i}{}^{13}C_i{}^1H_{23-j}{}^2H_j{}^{14}N_{2-n}{}^{15}N_n{}^{16}O_{4-o}{}^{18}O_o$ | $i \leq 16, j \leq 23, n \leq 2, o \leq 4$ |
| 23 | H15C12N2O3 | $^{12}C_{12-i}{}^{13}C_i{}^1H_{15-j}{}^2H_j{}^{14}N_{2-n}{}^{15}N_n{}^{16}O_{3-o}{}^{18}O_o$ | $i \leq 12, j \leq 15, n \leq 2, o \leq 3$ |
| 24 | H19C14N2O4 | $^{12}C_{14-i}{}^{13}C_i{}^1H_{19-j}{}^2H_j{}^{14}N_{2-n}{}^{15}N_n{}^{16}O_{4-o}{}^{18}O_o$ | $i \leq 14, j \leq 19, n \leq 2, o \leq 4$ |
| 25 | H13C11N2O2 | $^{12}C_{11-i}{}^{13}C_i{}^1H_{13-j}{}^2H_j{}^{14}N_{2-n}{}^{15}N_n{}^{16}O_{2-o}{}^{18}O_o$ | $i \leq 11, j \leq 13, n \leq 2, o \leq 2$ |
| 26 | H7C8N2O2 | $^{12}C_{8-i}{}^{13}C_i{}^1H_{7-j}{}^2H_j{}^{14}N_{2-n}{}^{15}N_n{}^{16}O_{2-o}{}^{18}O_o$ | $i \leq 8, j \leq 7, n \leq 2, o \leq 2$ |
| 27 | H21C18N4O5 | $^{12}C_{18-i}{}^{13}C_i{}^1H_{21-j}{}^2H_j{}^{14}N_{4-n}{}^{15}N_n{}^{16}O_{5-o}{}^{18}O_o$ | $i \leq 18, j \leq 21, n \leq 4, o \leq 5$ |
| 28 | H21C18N4O5 | $^{12}C_{18-i}{}^{13}C_i{}^1H_{21-j}{}^2H_j{}^{14}N_{4-n}{}^{15}N_n{}^{16}O_{5-o}{}^{18}O_o$ | $i \leq 18, j \leq 21, n \leq 4, o \leq 5$ |
| 29 | H12C14N8O | $^{12}C_{14-i}{}^{13}C_i{}^1H_{12-j}{}^2H_j{}^{14}N_{8-n}{}^{15}N_n{}^{16}O_{1-o}{}^{18}O_o$ | $i \leq 14, j \leq 12, n \leq 8, o \leq 1$ |
| 30 | H27C27N8O4 | $^{12}C_{27-i}{}^{13}C_i{}^1H_{27-j}{}^2H_j{}^{14}N_{8-n}{}^{15}N_n{}^{16}O_{4-o}{}^{18}O_o$ | $i \leq 27, j \leq 27, n \leq 8, o \leq 4$ |
| 31 | H10C17N6O | $^{12}C_{17-i}{}^{13}C_i{}^1H_{10-j}{}^2H_j{}^{14}N_{6-n}{}^{15}N_n{}^{16}O_{1-o}{}^{18}O_o$ | $i \leq 17, j \leq 10, n \leq 6, o \leq 1$ |
| 32 | H10C9N6O | $^{12}C_{9-i}{}^{13}C_i{}^1H_{10-j}{}^2H_j{}^{14}N_{6-n}{}^{15}N_n{}^{16}O_{1-o}{}^{18}O_o$ | $i \leq 9, j \leq 10, n \leq 6, o \leq 1$ |
| 33 | H31C30N12O4 | $^{12}C_{30-i}{}^{13}C_i{}^1H_{31-j}{}^2H_j{}^{14}N_{12-n}{}^{15}N_n{}^{16}O_{4-o}{}^{18}O_o$ | $i \leq 30, j \leq 31, n \leq 12, o \leq 4$ |
| 34 | H35C31N8O6 | $^{12}C_{31-i}{}^{13}C_i{}^1H_{35-j}{}^2H_j{}^{14}N_{8-n}{}^{15}N_n{}^{16}O_{6-o}{}^{18}O_o$ | $i \leq 31, j \leq 35, n \leq 8, o \leq 6$ |
| 35 | H12C15N8O | $^{12}C_{15-i}{}^{13}C_i{}^1H_{12-j}{}^2H_j{}^{14}N_{8-n}{}^{15}N_n{}^{16}O_{1-o}{}^{18}O_o$ | $i \leq 15, j \leq 12, n \leq 8, o \leq 1$ |
| 36 | H8C12N9O | $^{12}C_{12-i}{}^{13}C_i{}^1H_{8-j}{}^2H_j{}^{14}N_{9-n}{}^{15}N_n{}^{16}O_{1-o}{}^{18}O_o$ | $i \leq 12, j \leq 8, n \leq 9, o \leq 1$ |
| 37 | H6C11N8O | $^{12}C_{11-i}{}^{13}C_i{}^1H_{6-j}{}^2H_j{}^{14}N_{8-n}{}^{15}N_n{}^{16}O_{1-o}{}^{18}O_o$ | $i \leq 11, j \leq 6, n \leq 8, o \leq 1$ |
| 38 | H35C31N8O4 | $^{12}C_{31-i}{}^{13}C_i{}^1H_{35-j}{}^2H_j{}^{14}N_{8-n}{}^{15}N_n{}^{16}O_{4-o}{}^{18}O_o$ | $i \leq 31, j \leq 35, n \leq 8, o \leq 4$ |
| 39 | H20C12N2O2 | $^{12}C_{12-i}{}^{13}C_i{}^1H_{20-j}{}^2H_j{}^{14}N_{2-n}{}^{15}N_n{}^{16}O_{2-o}{}^{18}O_o$ | $i \leq 12, j \leq 20, n \leq 2, o \leq 2$ |

TABLE 5-continued

For all following equations: $i \geq 0, j \geq 0, l \geq 0, m \geq 0, n \geq 0, o \geq 0, p \geq 0,$ and $q \geq 0$.

| | Coded element Formula | Modified Equations | Range Maximums |
|---|---|---|---|
| 40 | H13C7N2O | $^{12}C_{7-i}{}^{13}C_i{}^1H_{13-j}{}^2H_j{}^{14}N_{2-n}{}^{15}N_n{}^{16}O_{1-o}{}^{18}O_o$ | $i \leq 7, j \leq 13, n \leq 2, o \leq 1$ |
| 41 | H25C18N3O3 | $^{12}C_{18-i}{}^{13}C_i{}^1H_{25-j}{}^2H_j{}^{14}N_{3-n}{}^{15}N_n{}^{16}O_{3-o}{}^{18}O_o$ | $i \leq 18, j \leq 25, n \leq 3, o \leq 3$ |

Example 11

Utilization of Isotopic Small Molecule Labels

In other embodiments, the analyte is a small molecule other than a peptide. In this instance, the isotopic tagging reagent is any compound able to covalently bind to the small molecule analyte or that is able to be incorporated into the analyte during synthesis of the analyte.

Figure 28:
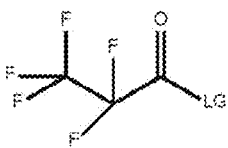
FIG. 28. Structures, chemical formulas, and coded element formulas for small molecule labels which can be used as isotopic tagging reagents.
Figure 28:
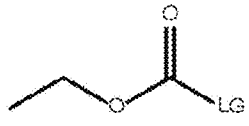
Figure 28:
Figure 28:
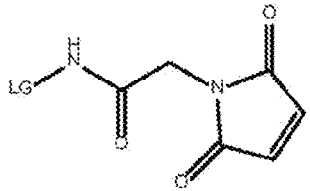
Figure 28:
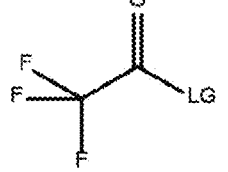
Figure 28:
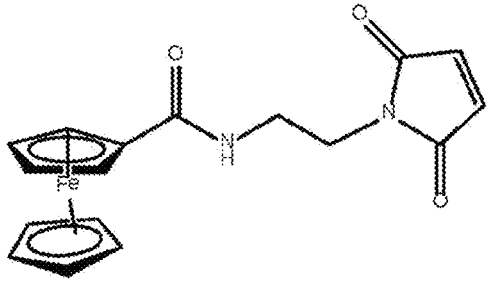
Figure 28:
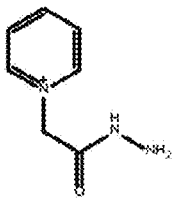
Figure 28:
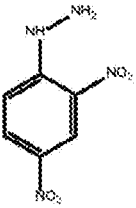
Figure 28:
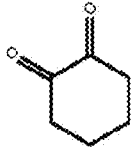
Figure 28:
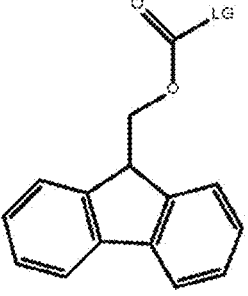
Figure 28:
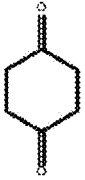
Figure 28:
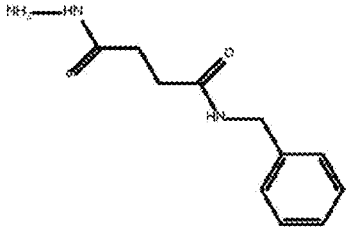
Figure 28:
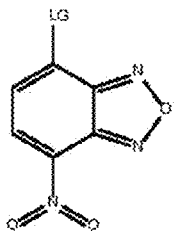
Figure 28:
Figure 28:
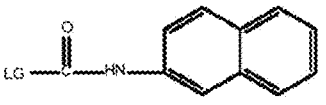
Figure 28:
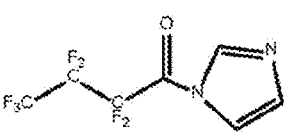

FIG. 28 provides the structures for forty-two small molecule labels that can be isotopically labeled and attached to a small molecule. These small molecule labels contain one or more atoms or a leaving group (designated as "LG" in the structure) which leave the small molecule label when the label is reacted with the analyte. Accordingly, these atoms or leaving group are not part of the isotopically labeled analyte. The leaving group is any functional group that allows the peptide label to react with a functional group of a peptide, such as an amine reactive group or carboxyl reactive group. The second column in FIG. 28 provides the chemical formula for each compound (not including any leaving groups (LG)), and the third column provides the coded element formula. Using the coded element formula for each compound, equation (1) described above can be modified to give an equation for each compound that describes all possible isotopologues for that compound.

Table 6a provides the modified equations for the small molecule labels of FIG. 28, where the modified equations describe the different possible isotopologues for each label. The maximum number for each heavy isotope for each modified equation is provided in the third column. For example, compound 2 of FIG. 28, which contains a leaving group which does not form part of the isotopically labeled analyte, is provided as item 2 in Table 6a, with the modified equation for this compound being:

$$^{12}C_{3-i}{}^{13}C_i{}^1H_{9-j}{}^2H_j{}^{28}Si_{1-q}{}^{30}Si_q. \qquad (6)$$

The possible isotopologues of this compound falls within their respective given modified equations.

The isotopologues for a particular small molecule label are provided to the analyte in each sample and the isotopologues are detected during mass spectrometry based on the small differences in their molecular masses. Relative quantification of the analyte in each sample is then determined by comparing the relative amounts of the detected isotopologues. Absolute quantification is by incorporating a standard (i.e., a specific isotopologue present in a known amount) in one of the samples.

TABLE 6a

For all following equations: $i \geq 0, j \geq 0, l \geq 0, m \geq 0, n \geq 0, o \geq 0, p \geq 0,$ and $q \geq 0$.

| | Coded element Formula | Modified Equations | Range Maximums |
|---|---|---|---|
| 1 | H14C9N | $^{12}C_{9-i}{}^{13}C_i{}^1H_{14-j}{}^2H_j{}^{14}N_{1-n}{}^{15}N_n$ | $i \leq 9, j \leq 14, n \leq 1$ |
| 2 | H9C3Si | $^{12}C_{3-i}{}^{13}C_i{}^1H_{9-j}{}^2H_j{}^{28}Si_{1-q}{}^{30}Si_q$ | $i \leq 3, j \leq 9, q \leq 1$ |
| 3 | H7C11NS | $^{12}C_{11-i}{}^{13}C_i{}^1H_{7-j}{}^2H_j{}^{14}N_{1-n}{}^{15}N_n{}^{32}S_{1-p}{}^{34}S_p$ | $i \leq 11, j \leq 7, n \leq 1, p \leq 1$ |
| 4 | H16C12N6O2S | $^{12}C_{12-i}{}^{13}C_i{}^1H_{16-j}{}^2H_j{}^{14}N_{6-n}{}^{15}N_n{}^{16}O_{2-o}{}^{18}O_o{}^{32}S_{1-p}{}^{34}S_p$ | $i \leq 12, j \leq 16, n \leq 6, o \leq 1, p \leq 1$ |
| 5 | H15C6Si | $^{12}C_{6-i}{}^{13}C_i{}^1H_{15-j}{}^2H_j{}^{28}Si_{1-q}{}^{30}Si_q$ | $i \leq 6, j \leq 15, q \leq 1$ |
| 6 | H3C2O2 | $^{12}C_{2-i}{}^{13}C_i{}^1H_{3-j}{}^2H_j{}^{16}O_{2-o}{}^{18}O_o$ | $i \leq 2, j \leq 3, o \leq 2$ |
| 7 | C3O | $^{12}C_{3-i}{}^{13}C_i{}^{16}O_{1-o}{}^{18}O_o$ | $i \leq 3, o \leq 1$ |
| 8 | H5C4O2 | $^{12}C_{4-i}{}^{13}C_i{}^1H_{5-j}{}^2H_j{}^{16}O_{2-o}{}^{18}O_o$ | $i \leq 4, j \leq 5, o \leq 2$ |
| 9 | H2CN2 | $^{12}C_{1-i}{}^{13}C_i{}^1H_{2-j}{}^2H_j{}^{14}N_{2-n}{}^{15}N_n$ | $i \leq 1, j \leq 2, n \leq 2$ |
| 10 | H4C6N2O2 | $^{12}C_{6-i}{}^{13}C_i{}^1H_{4-j}{}^2H_j{}^{14}N_{2-n}{}^{15}N_n{}^{16}O_{2-o}{}^{18}O_o$ | $i \leq 6, j \leq 4, n \leq 2, o \leq 2$ |
| 11 | C2O | $^{12}C_{2-i}{}^{13}C_i{}^{16}O_{1-o}{}^{18}O_o$ | $i \leq 2, o \leq 1$ |
| 12 | H6C7N2O3 | $^{12}C_{7-i}{}^{13}C_i{}^1H_{6-j}{}^2H_j{}^{14}N_{2-n}{}^{15}N_n{}^{16}O_{3-o}{}^{18}O_o$ | $i \leq 7, j \leq 6, n \leq 2, o \leq 3$ |
| 13 | H7C7N3O | $^{12}C_{7-i}{}^{13}C_i{}^1H_{7-j}{}^2H_j{}^{14}N_{3-n}{}^{15}N_n{}^{16}O_{1-o}{}^{18}O_o$ | $i \leq 7, j \leq 7, n \leq 3, o \leq 1$ |
| 14 | H3C6N4O4 | $^{12}C_{6-i}{}^{13}C_i{}^1H_{3-j}{}^2H_j{}^{14}N_{4-n}{}^{15}N_n{}^{16}O_{4-o}{}^{18}O_o$ | $i \leq 6, j \leq 3, n \leq 4, o \leq 4$ |
| 15 | HC6O2 | $^{12}C_{6-i}{}^{13}C_i{}^1H_{1-j}{}^2H_j{}^{16}O_{2-o}{}^{18}O_o$ | $i \leq 6, j \leq 1, o \leq 2$ |
| 16 | H11C15O2 | $^{12}C_{15-i}{}^{13}C_i{}^1H_{11-j}{}^2H_j{}^{16}O_{2-o}{}^{18}O_o$ | $i \leq 15, j \leq 11, o \leq 2$ |
| 17 | H8C6O2 | $^{12}C_{6-i}{}^{13}C_i{}^1H_{8-j}{}^2H_j{}^{16}O_{2-o}{}^{18}O_o$ | $i \leq 6, j \leq 8, o \leq 2$ |
| 18 | H12C12N3O2S | $^{12}C_{12-i}{}^{13}C_i{}^1H_{12-j}{}^2H_j{}^{14}N_{3-n}{}^{15}N_n{}^{16}O_{2-o}{}^{18}O_o{}^{32}S_{1-p}{}^{34}S_p$ | $i \leq 12, j \leq 12, n \leq 3, o \leq 2, p \leq 1$ |
| 19 | H23C18N2O | $^{12}C_{18-i}{}^{13}C_i{}^1H_{23-j}{}^2H_j{}^{14}N_{2-n}{}^{15}N_n{}^{16}O_{1-o}{}^{18}O_o$ | $i \leq 18, j \leq 23, n \leq 2, o \leq 1$ |
| 20 | H4C5N3 | $^{12}C_{5-i}{}^{13}C_i{}^1H_{4-j}{}^2H_j{}^{14}N_{3-n}{}^{15}N_n$ | $i \leq 5, j \leq 4, n \leq 3$ |
| 21 | H8C6O2 | $^{12}C_{6-i}{}^{13}C_i{}^1H_{8-j}{}^2H_j{}^{16}O_{2-o}{}^{18}O_o$ | $i \leq 6, j \leq 8, o \leq 2$ |
| 22 | H7C6N3 | $^{12}C_{6-i}{}^{13}C_i{}^1H_{7-j}{}^2H_j{}^{14}N_{3-n}{}^{15}N_n$ | $i \leq 6, j \leq 7, n \leq 3$ |
| 23 | H11C6N2O | $^{12}C_{6-i}{}^{13}C_i{}^1H_{11-j}{}^2H_j{}^{14}N_{2-n}{}^{15}N_n{}^{16}O_{1-o}{}^{18}O_o$ | $i \leq 6, j \leq 11, n \leq 2, o \leq 1$ |
| 24 | H11C11N3O | $^{12}C_{11-i}{}^{13}C_i{}^1H_{11-j}{}^2H_j{}^{14}N_{3-n}{}^{15}N_n{}^{16}O_{1-o}{}^{18}O_o$ | $i \leq 11, j \leq 11, n \leq 3, o \leq 1$ |
| 25 | H2C6N3O3 | $^{12}C_{6-i}{}^{13}C_i{}^1H_{2-j}{}^2H_j{}^{14}N_{3-n}{}^{15}N_n{}^{16}O_{3-o}{}^{18}O_o$ | $i \leq 6, j \leq 2, n \leq 3, o \leq 3$ |
| 26 | H10C9N2S | $^{12}C_{9-i}{}^{13}C_i{}^1H_{10-j}{}^2H_j{}^{14}N_{2-n}{}^{15}N_n{}^{32}S_{1-p}{}^{34}S_p$ | $i \leq 9, j \leq 10, n \leq 2, p \leq 1$ |
| 27 | H7C11NO | $^{12}C_{11-i}{}^{13}C_i{}^1H_{7-j}{}^2H_j{}^{14}N_{1-n}{}^{15}N_n{}^{16}O_{1-o}{}^{18}O_o$ | $i \leq 11, j \leq 7, n \leq 1, o \leq 1$ |
| 28 | C4O | $^{12}C_{4-i}{}^{13}C_i{}^{16}O_{1-o}{}^{18}O_o$ | $i \leq 4, o \leq 1$ |
| 29 | H4C7N2O2S | $^{12}C_{7-i}{}^{13}C_i{}^1H_{4-j}{}^2H_j{}^{14}N_{2-n}{}^{15}N_n{}^{16}O_{2-o}{}^{18}O_o{}^{32}S_{1-p}{}^{34}S_p$ | $i \leq 7, j \leq 4, n \leq 2, o \leq 2, p \leq 1$ |
| 30 | H4C7NO4 | $^{12}C_{7-i}{}^{13}C_i{}^1H_{4-j}{}^2H_j{}^{14}N_{1-n}{}^{15}N_n{}^{16}O_{4-o}{}^{18}O_o$ | $i \leq 7, j \leq 4, n \leq 1, o \leq 4$ |

TABLE 6a-continued

For all following equations: $i \geq 0, j \geq 0, l \geq 0, m \geq 0, n \geq 0, o \geq 0, p \geq 0,$ and $q \geq 0$.

| | Coded element Formula | Modified Equations | Range Maximums |
|---|---|---|---|
| 31 | H14C8NO3 | $^{12}C_{8-i}{}^{13}C_i{}^1H_{14-j}{}^2H_j{}^{14}N_{1-n}{}^{15}N_n{}^{16}O_{3-o}{}^{18}O_o$ | $i \leq 8, j \leq 14, n \leq 1, o \leq 3$ |
| 32 | H14C14NO4 | $^{12}C_{14-i}{}^{13}C_i{}^1H_{14-j}{}^2H_j{}^{14}N_{1-n}{}^{15}N_n{}^{16}O_{4-o}{}^{18}O_o$ | $i \leq 14, j \leq 14, n \leq 1, o \leq 4$ |
| 33 | H12C9N2 | $^{12}C_{9-i}{}^{13}C_i{}^1H_{12-j}{}^2H_j{}^{14}N_{2-n}{}^{15}N_n$ | $i \leq 9, j \leq 12, n \leq 2$ |
| 34 | H12C12N3O2S | $^{12}C_{12-i}{}^{13}C_i{}^1H_{12-j}{}^2H_j{}^{14}N_{3-n}{}^{15}N_n{}^{16}O_{2-o}{}^{18}O_o{}^{32}S_{1-p}{}^{34}S_p$ | $i \leq 12, j \leq 12, n \leq 3, o \leq 2, p \leq 1$ |
| 35 | H12C12NO2S | $^{12}C_{12-i}{}^{13}C_i{}^1H_{12-j}{}^2H_j{}^{14}N_{1-n}{}^{15}N_n{}^{16}O_{2-o}{}^{18}O_o{}^{32}S_{1-p}{}^{34}S_p$ | $i \leq 12, j \leq 12, n \leq 1, o \leq 2, p \leq 1$ |
| 36 | H4C6NO2 | $^{12}C_{6-i}{}^{13}C_i{}^1H_{4-j}{}^2H_j{}^{14}N_{1-n}{}^{15}N_n{}^{16}O_{2-o}{}^{18}O_o$ | $i \leq 6, j \leq 4, n \leq 1, o \leq 2$ |
| 37 | H4C6N4O | $^{12}C_{6-i}{}^{13}C_i{}^1H_{4-j}{}^2H_j{}^{14}N_{4-n}{}^{15}N_n{}^{16}O_{1-o}{}^{18}O_o$ | $i \leq 6, j \leq 4, n \leq 4, o \leq 1$ |
| 38 | H15C20N2O | $^{12}C_{20-i}{}^{13}C_i{}^1H_{15-j}{}^2H_j{}^{14}N_{2-n}{}^{15}N_n{}^{16}O_{1-o}{}^{18}O_o$ | $i \leq 20, j \leq 15, n \leq 2, o \leq 1$ |
| 39 | H12C6N2 | $^{12}C_{6-i}{}^{13}C_i{}^1H_{12-j}{}^2H_j{}^{14}N_{2-n}{}^{15}N_n$ | $i \leq 6, j \leq 12, n \leq 2$ |
| 40 | H13C5NO | $^{12}C_{5-i}{}^{13}C_i{}^1H_{13-j}{}^2H_j{}^{14}N_{1-n}{}^{15}N_n{}^{16}O_{1-o}{}^{18}O_o$ | $i \leq 5, j \leq 13, n \leq 1, o \leq 1$ |
| 41 | H4C6NO2 | $^{12}C_{6-i}{}^{13}C_i{}^1H_{4-j}{}^2H_j{}^{14}N_{1-n}{}^{15}N_n{}^{16}O_{2-o}{}^{18}O_o$ | $i \leq 6, j \leq 4, n \leq 1, o \leq 2$ |
| 42 | H18C8N | $^{12}C_{8-i}{}^{13}C_i{}^1H_{18-j}{}^2H_j{}^{14}N_{1-n}{}^{15}N_n$ | $i \leq 8, j \leq 18, n \leq 1$ |

Table 6b provided as an appendix is a part of the specification provided herein that is also hereby incorporated by reference. Table 6b provides possible coded element combinations that result in isotopologues of forty-two small molecule labels useful in embodiments of the invention.

REFERENCES

1. A. Ducret, I. Van Oostveen, J. K. Eng, J. R. Yates, and R. Aebersold, High throughput protein characterization by automated reverse-phase chromatography electrospray tandem mass spectrometry. Protein Science, 1998. 7(3): p. 706-719.
2. A. J. Link, J. Eng, D. M. Schieltz, E. Carmack, G. J. Mize, D. R. Morris, B. M. Garvik, and J. R. Yates, Direct analysis of protein complexes using mass spectrometry. Nature Biotechnology, 1999. 17(7): p. 676-682.
3. H. B. Liu, R. G. Sadygov, and J. R. Yates, A model for random sampling and estimation of relative protein abundance in shotgun proteomics. Analytical Chemistry, 2004. 76(14): p. 4193-4201.
4. C. C. Wu, M. J. MacCoss, K. E. Howell, and J. R. Yates, A method for the comprehensive proteomic analysis of membrane proteins. Nature Biotechnology, 2003. 21(5): p. 532-538.
5. D. L. Tabb, L. Vega-Montoto, P. A. Rudnick, A. M. Variyath, A. J. L. Ham, D. M. Bunk, L. E. Kilpatrick, D. D. Billheimer, R. K. Blackman, H. L. Cardasis, S. A. Carr, K. R. Clauser, J. D. Jaffe, K. A. Kowalski, T. A. Neubert, F. E. Regnier, B. Schilling, T. J. Tegeler, M. Wang, P. Wang, J. R. Whiteaker, L. J. Zithmerman, S. J. Fisher, B. W. Gibson, C. R. Kinsinger, M. Mesri, H. Rodriguez, S. E. Stein, P. Tempst, A. G. Paulovich, D. C. Liebler, and C. Spiegelman, Repeatability and Reproducibility in Proteomic Identifications by Liquid Chromatography-Tandem Mass Spectrometry. Journal of Proteome Research, 2010. 9(2): p. 761-776.
6. J. V. Olsen, M. Vermeulen, A. Santamaria, C. Kumar, M. L. Miller, L. J. Jensen, F. Gnad, J. Cox, T. S. Jensen, E. A. Nigg, S. Brunak, and M. Mann, Quantitative Phosphoproteomics Reveals Widespread Full Phosphorylation Site Occupancy During Mitosis. Science Signaling, 2010. 3(104).
7. A. Moritz, Y. Li, A. L. Guo, J. Villen, Y. Wang, J. MacNeill, J. Kornhauser, K. Sprott, J. Zhou, A. Possemato, J. M. Ren, P. Hornbeck, L. C. Cantley, S. P. Gygi, J. Rush, and M. J. Comb, Akt-RSK-S6 Kinase Signaling Networks Activated by Oncogenic Receptor Tyrosine Kinases. Science Signaling, 2010. 3(136).
8. F. S. Oppermann, F. Gnad, J. V. Olsen, R. Hornberger, Z. Greff, G. Keri, M. Mann, and H. Daub, Large-scale Proteomics Analysis of the Human Kinome. Molecular & Cellular Proteomics, 2009. 8(7): p. 1751-1764.
9. J. R. Wisniewski, A. Zougman, N. Nagaraj, and M. Mann, Universal sample preparation method for proteome analysis. Nature Methods, 2009. 6(5): p. 359-U60.
10. G. Manning, D. B. Whyte, R. Martinez, T. Hunter, and S. Sudarsanam, The protein kinase complement of the human genome. Science, 2002. 298(5600): p. 1912-+,
11. M. Ashburner, C. A. Ball, J. A. Blake, D. Botstein, H. Butler, J. M. Cherry, A. P. Davis, K. Dolinski, S. S. Dwight, J. T. Eppig, M. A. Harris, D. P. Hill, L. Issel-Tarver, A. Kasarskis, S. Lewis, J. C. Matese, J. E. Richardson, M. Ringwald, G. M. Rubin, G. Sherlock, and C. Gene Ontology, Gene Ontology: tool for the unification of biology. Nature Genetics, 2000. 25(1): p. 25-29.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Lengthy table referenced here

US09366678-20160614-T00001

Please refer to the end of the specification for access instructions.

Lengthy table referenced here

US09366678-20160614-T00002

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US09366678B2). An electronic copy of the table will also be available from the USPTO upon request and payment of the fee set forth in 37 CFR 1.19(b)(3).

We claim:

1. A method for determining the abundances of an analyte in a plurality of samples, said method comprising the steps of:
   (a) providing a plurality of cell cultures including at least a first cell culture and a second cell culture;
   (b) providing a different isotopically labeled amino acid to each of said cell cultures, wherein each isotopically labeled amino acid comprises at least two stable heavy isotopes substituted for light isotopes in the normal amino acid, wherein both of the at least two heavy isotopes are, independently from one another, selected from the group consisting of $^{15}N$, $^{13}C$, $^{18}O$, and $^{34}S$, wherein said isotopically labeled amino acids of each of said cell cultures are isotopologues of the same amino acid, and wherein each isotopically labeled amino acid independently is characterized by a mass difference of 12 Da or less relative to a corresponding unlabeled amino acid;
   (c) growing cells of each of said cell cultures, thereby introducing a different isotopic label into proteins generated by each cell culture;
   (d) generating a sample for each of said cell cultures, wherein each sample is characterized by a different isotopically labeled analyte, said samples including at least a first sample for said first cell culture having a first isotopically labeled analyte and a second sample for said second cell culture having a second isotopically labeled analyte, wherein said isotopically labeled analytes of each sample are isotopologues; and wherein the difference of the molecular masses of said first isotopically labeled analyte and said second isotopically labeled analyte is less than or equal to 300 mDa;
   (e) analyzing said isotopically labeled analytes for each sample using a mass spectrometry analysis technique providing a resolving power equal to or greater than 240,000, thereby generating an independent and distinguishable mass spectrometry signal for the isotopically labeled analytes of each sample; and
   (f) comparing said mass spectrometry signals for the isotopically labeled analytes of each sample, thereby determining the abundances of the analyte in said plurality of samples.

2. The method of claim 1, wherein said step of analyzing said isotopically labeled analytes for each sample is carried out using a single stage mass spectrometry technique.

3. The method of claim 1, wherein said step of analyzing said isotopically labeled analytes for each sample using said mass spectrometry analysis technique comprises:
   generating ions from each of said isotopically labeled analytes for each sample;
   fragmenting said ions so as to generate product ions having a different isotopic label for each sample; and
   detecting said product ions for each sample.

4. The method of claim 3, wherein said product ions are peptide fragment ions having said isotopic label.

5. The method of claim 3, wherein said product ions are detected without further mass selection or fragmentation of said product ions.

6. The method of claim 1, wherein said step of providing said different isotopically labeled amino acid to each of said cell cultures comprises providing a growth medium to each of said cell cultures comprising the isotopically labeled amino acids.

7. The method of claim 1, wherein said introducing a different isotopic label into proteins generated by each cell culture is achieved via metabolic incorporation of the isotopically labeled amino acids into cells of said cell cultures.

8. The method of claim 1, wherein said step of generating a sample for each of said cell cultures comprises lysing said cells of each of said cell cultures; extracting proteins of each of said cell cultures and digesting proteins of each of said cell cultures.

9. The method of claim 1, wherein said step of analyzing said isotopically labeled analytes for each sample comprises resolving said difference of the molecular masses of said isotopically labeled analytes.

10. The method of claim 1, wherein said difference of the molecular masses of said first isotopically labeled analyte and said second isotopically labeled analyte is less than or equal to 100 mDa.

11. The method of claim 1, wherein said difference of the molecular masses of said first isotopically labeled analyte and said second isotopically labeled analyte is selected over the range of 100 mDa to 1 mDa.

12. The method of claim 1, wherein each of said isotopically labeled analytes have a molecular mass within 50 mDa to 1 mDa of another of said isotopically labeled analyte.

13. The method of claim 1, wherein said isotopically labeled amino acids have a number of stable heavy isotopes selected from the group consisting of 2, 3, 4, 5, 6, 7, 8, 9, 10, 11, 12, 13, 14, 15, 16, 17, 18, 19, and 20.

14. The method of claim 1, wherein said isotopically labeled amino acids are selected from the group consisting of:
   an amino acid having at least two $^{13}C$ isotopes;
   an amino acid having at least one $^{13}C$ isotope and at least one $^{15}N$ isotope;
   an amino acid having at least one $^{13}C$ isotope and at least one $^{18}O$ isotope;
   an amino acid having at least one $^{13}C$ isotope and a $^{34}S$ isotope;
   an amino acid having at least two $^{15}N$ isotopes;
   an amino acid having at least one $^{15}N$ isotope and at least one $^{18}O$ isotope;
   an amino acid having at least one $^{15}N$ isotope and at least one $^{34}S$ isotope;
   an amino acid having at least two $^{18}O$ isotopes;
   an amino acid having at least one $^{18}O$ isotope and at least one $^{34}S$ isotope;
   an amino acid having at least one $^{13}C$ isotope, at least one $^{15}N$ isotope and at least one $^{2}H$ isotope;

an amino acid having at least one $^{13}C$ isotope, at least one $^{15}N$ isotope and at least one $^{18}O$ isotope;

an amino acid having at least one $^{13}C$ isotope, at least one $^{15}N$ isotope and at least one $^{34}S$ isotope; and an amino acid having at least one $^{18}O$ isotope, at least one $^{15}N$ isotope and at least one $^{34}S$ isotope.

15. The method of claim 1, wherein said isotopically labeled amino acids are selected from the group consisting of:

an amino acid having 1, 2, 3, or 4 $^{15}N$ isotopes;

an amino acid having 1, 2, 3, 4, 5, 6, 7, 8, 9, 10 or 11 $^{13}C$ isotopes;

an amino acid having 1 or 2 $^{18}O$ isotopes; and an amino acid having one $^{34}S$ isotope.

16. The method of claim 1, wherein said isotopically labeled amino acids are isotopologues of a naturally occurring amino acid.

17. The method of claim 1, wherein said isotopically labeled amino acids of each sample have an isotopic composition for its coded element formula selected from the group consisting of:

$^{12}C_{3-i}{}^{13}C_i{}^{1}H_{4-j}{}^{2}H_j{}^{14}N_{1-n}{}^{15}N_n{}^{16}O_{1-o}{}^{18}O_o$, wherein $i \leq 3$, $j \leq 4$, $n \leq 1$, $o \leq 1$;

$^{12}C_{6-i}{}^{13}C_i{}^{1}H_{7-j}{}^{2}H_j{}^{14}N_{4-n}{}^{15}N_n{}^{16}O_{1-o}{}^{18}O_o$, wherein $i \leq 6$, $j \leq 7$, $n \leq 4$, $o \leq 1$;

$^{12}C_{4-i}{}^{13}C_i{}^{1}H_{3-j}{}^{2}H_j{}^{14}N_{2-n}{}^{15}N_n{}^{16}O_{2-o}{}^{18}O_o$, wherein $i \leq 4$, $j \leq 3$, $n \leq 2$, $o \leq 2$;

$^{12}C_{4-i}{}^{13}C_i{}^{1}H_{3-j}{}^{2}H_j{}^{14}N_{1-n}{}^{15}N_n{}^{16}O_{2-o}{}^{18}O_o$, wherein $i \leq 4$, $j \leq 3$, $n \leq 1$, $o \leq 2$;

$^{12}C_{3-i}{}^{13}C_i{}^{1}H_{3-j}{}^{2}H_j{}^{14}N_{1-n}{}^{15}N_n{}^{16}O_{1-o}{}^{18}O_o{}^{32}S_{1-p}{}^{34}S_p$, wherein $i \leq 3$, $j \leq 3$, $n \leq 1$, $o \leq 1$, $p \leq 1$;

$^{12}C_{5-i}{}^{13}C_i{}^{1}H_{5-j}{}^{2}H_j{}^{14}N_{1-n}{}^{15}N_n{}^{16}O_{2-o}{}^{18}O_o$, wherein $i \leq 5$, $j \leq 5$, $n \leq 1$, $o \leq 2$;

$^{12}C_{5-i}{}^{13}C_i{}^{1}H_{5-j}{}^{2}H_j{}^{14}N_{2-n}{}^{15}N_n{}^{16}O_{2-o}{}^{18}O_o$, wherein $i \leq 5$, $j \leq 5$, $n \leq 2$, $o \leq 2$;

$^{12}C_{2-i}{}^{13}C_i{}^{1}H_{2-j}{}^{2}H_j{}^{14}N_{1-n}{}^{15}N_n{}^{16}O_{1-o}{}^{18}O_o$, wherein $i \leq 2$, $j \leq 2$, $n \leq 1$, $o \leq 1$;

$^{12}C_{6-i}{}^{13}C_i{}^{1}H_{5-j}{}^{2}H_j{}^{14}N_{3-n}{}^{15}N_n{}^{16}O_{1-o}{}^{18}O_o$, wherein $i \leq 6$, $j \leq 5$, $n \leq 3$, $o \leq 1$;

$^{12}C_{6-i}{}^{13}C_i{}^{1}H_{10-j}{}^{2}H_j{}^{14}N_{1-n}{}^{15}N_n{}^{16}O_{1-o}{}^{18}O_o$, wherein $i \leq 6$, $j \leq 1$, $0 \leq n \leq 1$, $o \leq 1$;

$^{12}C_{6-i}{}^{13}C_i{}^{1}H_{10-j}{}^{2}H_j{}^{14}N_{1-n}{}^{15}N_n{}^{16}O_{1-o}{}^{18}O_o$, wherein $i \leq 6$, $j \leq 10$, $n \leq 1$, $o \leq 1$;

$^{12}C_{6-i}{}^{13}C_i{}^{1}H_{9-j}{}^{2}H_j{}^{14}N_{2-n}{}^{15}N_n{}^{16}O_{1-o}{}^{18}O_o$, wherein $i \leq 6$, $j \leq 9$, $n \leq 2$, $o \leq 1$;

$^{12}C_{5-i}{}^{13}C_i{}^{1}H_{8-j}{}^{2}H_j{}^{14}N_{1-n}{}^{15}N_n{}^{16}O_{1-o}{}^{18}O_o{}^{32}S_{1-p}{}^{34}S_p$, wherein $i \leq 5$, $j \leq 8$, $n \leq 1$, $o \leq 1$, $p \leq 1$;

$^{12}C_{9-i}{}^{13}C_i{}^{1}H_{8-j}{}^{2}H_j{}^{14}N_{1-n}{}^{15}N_n{}^{16}O_{1-o}{}^{18}O_o$, wherein $i \leq 9$, $j \leq 8$, $n \leq 1$, $o \leq 1$;

$^{12}C_{5-i}{}^{13}C_i{}^{1}H_{7-j}{}^{2}H_j{}^{14}N_{1-n}{}^{15}N_n{}^{16}O_{1-o}{}^{18}O_o$, wherein $i \leq 5$, $j \leq 7$, $n \leq 1$, $o \leq 1$;

$^{12}C_{3-i}{}^{13}C_i{}^{1}H_{3-j}{}^{2}H_j{}^{14}N_{1-n}{}^{15}N_n{}^{16}O_{1-o}{}^{18}O_o$, wherein $i \leq 3$, $j \leq 3$, $n \leq 1$, $o \leq 1$;

$^{12}C_{4-i}{}^{13}C_i{}^{1}H_{5-j}{}^{2}H_j{}^{14}N_{1-n}{}^{15}N_n{}^{16}O_{1-o}{}^{18}O_o$, wherein $i \leq 4$, $j \leq 5$, $n \leq 1$, $o \leq 1$;

$^{12}C_{11-i}{}^{13}C_i{}^{1}H_{8-j}{}^{2}H_j{}^{14}N_{2-n}{}^{15}N_n{}^{16}O_{1-o}{}^{18}O_o$, wherein $i \leq 11$, $j \leq 8$, $n \leq 2$, $o \leq 1$;

$^{12}C_{9-i}{}^{13}C_i{}^{1}H_{7-j}{}^{2}H_j{}^{14}N_{1-n}{}^{15}N_n{}^{16}O_{1-o}{}^{18}O_o$, wherein $i \leq 9$, $j \leq 7$, $n \leq 1$, $o \leq 1$; and $^{12}C_{5-i}{}^{13}C_i{}^{1}H_{8-j}{}^{2}H_j{}^{14}N_{1-n}{}^{15}N_n{}^{16}O_{1-o}{}^{18}O_o$, wherein $i \leq 5$, $j \leq 8$, $n \leq 1$, $o \leq 1$;

wherein each of i, j, n, o and p are independently an integer or 0.

18. The method of claim 1, wherein said isotopically labeled amino acids have the formula:

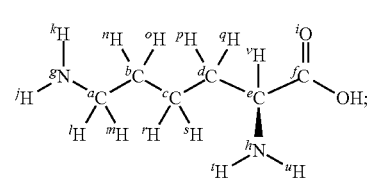

(FX1)

wherein, $^gN$ and $^hN$ are both $^{15}N$; or one of $^gN$ and $^hN$ is $^{15}N$, and one of $^aC$, $^bC$, $^cC$, $^dC$, $^eC$ and $^fC$ is $^{13}C$; or $^iO$ is $^{18}O$; or two of $^aC$, $^bC$, $^cC$, $^dC$, $^eC$ and $^fC$ are $^{13}C$.

19. The method of claim 1, wherein said isotopically labeled amino acids have the formula:

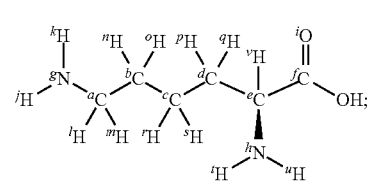

(FX1)

wherein, $^gN$ and $^hN$ are both $^{15}N$, and $^iO$ is $^{18}O$; or $^gN$ and $^hN$ are both $^{15}N$, and two of $^aC$, $^bC$, $^cC$, $^dC$, $^eC$ and $^fC$ are $^{13}C$; or $^gN$ and $^hN$ are both $^{15}N$, one of $^aC$, $^bC$, $^cC$, $^dC$, $^eC$ and $^fC$ is $^{13}C$, and one of $^jH$, $^kH$, $^lH$, $^mH$, $^nH$, $^oH$, $^pH$, $^qH$, $^rH$, $^sH$, $^tH$, $^uH$ and $^vH$ is $^2H$; or one of $^gN$ and $^hN$ is $^{15}N$, one of $^aC$, $^bC$, $^cC$, $^dC$, $^eC$ and $^fC$ is $^{13}C$, and $^iO$ is $^{18}O$; or $^gN$ and $^hN$ are both $^{15}N$, and two of $^jH$, $^kH$, $^lH$, $^mH$, $^nH$ $^oH$, $^pH$, $^qH$, $^rH$, $^sH$, $^tH$, $^uH$ and $^vH$ are $^2H$; or one of $^gN$ and $^hN$ is $^{15}N$, and three of $^aC$, $^bC$, $^cC$, $^dC$, $^eC$ and $^fC$ are $^{13}C$; or one of $^gN$ and $^hN$ is $^{15}N$, one of $^jH$, $^kH$, $^lH$, $^mH$, $^nH$, $^oH$, $^pH$, $^qH$, $^rH$, $^sH$, $^tH$, $^uH$ and $^vH$ is $^2H$, and $^iO$ is $^{18}O$; or one of $^gN$ and $^hN$ is $^{15}N$, two of $^aC$, $^bC$, $^cC$, $^dC$, $^eC$ and $^fC$ are $^{13}C$, and one of $^jH$, $^kH$, $^lH$, $^mH$, $^nH$, $^oH$, $^pH$, $^qH$, $^rH$, $^sH$, $^tH$, $^uH$ and $^vH$ is $^2H$; or two of $^aC$, $^bC$, $^cC$, $^dC$, $^eC$ and $^fC$ are $^{13}C$, and $^iO$ is $^{18}O$; or one of $^gN$ and $^hN$ is $^{15}N$, one of $^aC$, $^bC$, $^cC$, $^dC$, $^eC$ and $^fC$ is $^{13}C$, and two of $^jH$, $^kH$, $^lH$, $^mH$, $^nH$, $^oH$, $^pH$, $^qH$, $^rH$, $^sH$, $^tH$, $^uH$ and $^vH$ are $^2H$; or four of $^aC$, $^bC$, $^cC$, $^dC$, $^eC$ and $^fC$ are $^{13}C$; or one of $^aC$, $^bC$, $^cC$, $^dC$, $^eC$ and $^fC$ is $^{13}C$, one of $^jH$, $^kH$, $^lH$, $^mH$, $^nH$, $^oH$, $^pH$, $^qH$, $^rH$, $^sH$, $^tH$, $^uH$ and $^vH$ is $^2H$, and $^iO$ is $^{18}O$; or three of $^aC$, $^bC$, $^cC$, $^dC$, $^eC$ and $^fC$ are $^{13}C$, and one of $^jH$, $^kH$, $^lH$, $^mH$, $^nH$, $^oH$, $^pH$, $^qH$, $^rH$, $^sH$, $^tH$, $^uH$ and $^vH$ is $^2H$; or two of $^aC$, $^bC$, $^cC$, $^dC$, $^eC$ and $^fC$ are $^{13}C$, and two of $^jH$, $^kH$, $^lH$, $^mH$, $^nH$, $^oH$, $^pH$, $^qH$, $^rH$, $^sH$, $^tH$, $^uH$ and $^vH$ are $^2H$.

20. The method of claim 1, wherein said isotopically labeled amino acids have the formula:

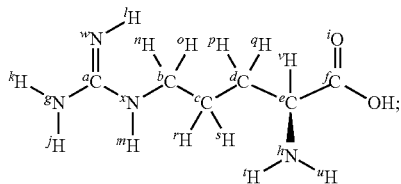

(FX2)

wherein,
two of $^gN$, $^hN$, $^wN$ and $^xN$ are $^{15}N$; or
one of $^gN$, $^hN$, $^wN$ and $^xN$ is $^{15}N$, and one of $^aC$, $^bC$, $^cC$, $^dC$, $^eC$ and $^fC$ is $^{13}C$; or
$^iO$ is $^{18}O$; or
two of $^aC$, $^bC$, $^cC$, $^dC$, $^eC$ and $^fC$ are $^{13}C$.

21. The method of claim 1, wherein said isotopically labeled amino acids have the formula:

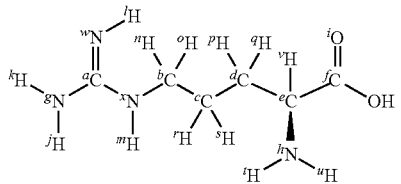

(FX2)

wherein,
four of $^gN$, $^hN$, $^wN$ and $^xN$ are $^{15}N$; or
three of $^gN$, $^hN$, $^wN$ and $^xN$ are $^{15}N$, and one of $^aC$, $^bC$, $^cC$, $^dC$, $^eC$ and $^fC$ is $^{13}C$; or
three of $^gN$, $^hN$, $^wN$ and $^xN$ are $^{15}N$, and one of $^jH$, $^kH$, $^lH$, $^mH$, $^nH$, $^oH$, $^pH$, $^qH$, $^rH$, $^sH$, $^tH$, $^uH$ and $^vH$ is $^2H$; or
two of $^gN$, $^hN$, $^wN$ and $^xN$ are $^{15}N$, and $^iO$ is $^{18}O$; or
two of $^gN$, $^hN$, $^wN$ and $^xN$ are $^{15}N$, and two of $^aC$, $^bC$, $^cC$, $^dC$, $^eC$ and $^fC$ are $^{13}C$; or
two of $^gN$, $^hN$, $^wN$ and $^xN$ are $^{15}N$, one of $^aC$, $^bC$, $^cC$, $^dC$, $^eC$ and $^fC$ is $^{13}C$, and one of $^jH$, $^kH$, $^lH$, $^mH$, $^nH$, $^oH$, $^pH$, $^qH$, $^rH$, $^sH$, $^tH$, $^uH$ and $^vH$ is $^2H$; or
one of $^gN$, $^hN$, $^wN$ and $^xN$ is $^{15}N$, one of $^aC$, $^bC$, $^cC$, $^dC$, $^eC$ and $^fC$ is $^{13}C$, and $^iO$ is $^{18}O$; or
two of $^gN$, $^hN$, $^wN$ and $^xN$ are $^{15}N$, and two of $^jH$, $^kH$, $^lH$, $^mH$, $^nH$, $^oH$, $^pH$, $^qH$, $^rH$, $^sH$, $^tH$, $^uH$ and $^vH$ are $^2H$; or
one of $^gN$, $^hN$, $^wN$ and $^xN$ is $^{15}N$, and three of $^aC$, $^bC$, $^cC$, $^dC$, $^eC$ and $^fC$ are $^{13}C$; or
one of $^gN$, $^hN$, $^wN$ and $^xN$ is $^{15}N$, one of $^jH$, $^kH$, $^lH$, $^mH$, $^nH$, $^oH$, $^pH$, $^qH$, $^rH$, $^sH$, $^tH$, $^uH$ and $^vH$ is $^2H$, and $^iO$ is $^{18}O$; or
one of $^gN$, $^hN$, $^wN$ and $^xN$ is $^{15}N$, two of $^aC$, $^bC$, $^cC$, $^dC$, $^eC$ and $^fC$ are $^{13}C$, and one of $^jH$, $^kH$, $^lH$, $^mH$, $^nH$, $^oH$, $^pH$, $^qH$, $^rH$, $^sH$, $^tH$, $^uH$ and $^vH$ is $^2H$; or
two of $^aC$, $^bC$, $^cC$, $^dC$, $^eC$ and $^fC$ are $^{13}C$, and $^iO$ is $^{18}O$; or
one of $^gN$, $^hN$, $^wN$ and $^xN$ is $^{15}N$, one of $^aC$, $^bC$, $^cC$, $^dC$, $^eC$ and $^fC$ is $^{13}C$, and two of $^jH$, $^kH$, $^lH$, $^mH$, $^nH$, $^oH$, $^pH$, $^qH$, $^rH$, $^sH$, $^tH$, $^uH$ and $^vH$ are $^2H$; or
four of $^aC$, $^bC$, $^cC$, $^dC$, $^eC$ and $^fC$ are $^{13}C$; or
one of $^aC$, $^bC$, $^cC$, $^dC$, $^eC$ and $^fC$ is $^{13}C$, one of $^jH$, $^kH$, $^lH$, $^mH$, $^nH$, $^oH$, $^pH$, $^qH$, $^rH$, $^sH$, $^tH$, $^uH$ and $^vH$ is $^2H$, and $^iO$ is $^{18}O$; or
three of $^aC$, $^bC$, $^cC$, $^dC$, $^eC$ and $^fC$ are $^{13}C$, and one of $^jH$, $^kH$, $^lH$, $^mH$, $^nH$, $^oH$, $^pH$, $^qH$, $^rH$, $^sH$, $^tH$, $^uH$ and $^vH$ is $^2H$; or
two of $^aC$, $^bC$, $^cC$, $^dC$, $^eC$ and $^fC$ are $^{13}C$, and two of $^jH$, $^kH$, $^lH$, $^mH$, $^nH$, $^oH$, $^pH$, $^qH$, $^rH$, $^sH$, $^tH$, $^uH$ and $^vH$ are $^2H$.

22. The method of claim 1, wherein:
at least a portion of said isotopically labeled analytes comprises at least one $^{12}C$ isotope and at least one $^{15}N$ isotope; and at least a portion of said isotopically labeled analytes comprises at least one $^{13}C$ isotope and at least one $^{14}N$ isotope; or
at least a portion of said isotopically labeled analytes comprises at least one $^{12}C$ isotope and at least one $^2H$ isotope; and at least a portion of said isotopically labeled analytes comprises at least one $^{13}C$ isotope and at least one $^1H$ isotope; or
at least a portion of said isotopically labeled analytes comprises at least one $^{14}N$ isotope and at least one $^2H$ isotope; and at least a portion of said isotopically labeled analytes comprises at least one $^{15}N$ isotope and at least one $^1H$ isotope or
at least a portion of said isotopically labeled analytes comprises at least one $^{16}O$ isotope; and at least a portion of said isotopically labeled analytes comprises at least one $^{18}O$ isotope; or
at least a portion of said isotopically labeled analytes comprises at least two $^{13}C$, $^2H$ or $^{15}N$ isotopes and at least one $^{16}O$ isotope; and at least a portion of said isotopically labeled analytes comprises at least one $^{18}O$ isotope and at least at least two $^{12}C$, $^1H$ or $^{14}N$ isotopes; or
at least a portion of said isotopically labeled analytes comprises at least two $^{13}C$, $^2H$ or $^{15}N$ isotopes; and at least a portion of said isotopically labeled analytes comprises at least one $^{34}S$ isotope and at least at least two $^{12}C$, $^1H$ or $^{14}N$ isotopes.

23. The method of claim 1, wherein each of said isotopically labeled analytes are independently protein analytes or modified protein analytes having a different isotopic label or wherein each of said isotopically labeled analytes are independently peptide analytes or modified peptide analytes having a different isotopic label.

24. The method of claim 1, wherein the step of providing said plurality of cell cultures comprises providing 2 to 20 cell cultures; and wherein the step of generating a sample for each of said cell cultures comprises generating 2 to 20 samples.

25. The method of claim 1, wherein said introducing a different isotopic label into proteins generated by each cell culture is achieved via metabolic incorporation of the isotopically labeled amino acids into cells of said cell cultures.

* * * * *